United States Patent
Miyata et al.

(10) Patent No.: US 12,410,366 B2
(45) Date of Patent: *Sep. 9, 2025

(54) INFRARED-EMITTING COMPOUND, AND LUMINESCENT THIN FILM, LUMINESCENT PARTICLE, WAVELENGTH CONVERSION FILM AND INFRARED-EMITTING SURFACE LIGHT SOURCE CONTAINING SAME

(71) Applicant: Konica Minolta, Inc., Tokyo (JP)

(72) Inventors: Yasuo Miyata, Yokohama (JP); Noriko Ueda, Hachioji (JP); Hiroki Tatsumi, Toyohashi (JP); Ryo Nakabayashi, Hachioji (JP)

(73) Assignee: KONICA MINOLTA, INC., Tokyo (JP)

( * ) Notice: Subject to any disclaimer, the term of this patent is extended or adjusted under 35 U.S.C. 154(b) by 904 days.

This patent is subject to a terminal disclaimer.

(21) Appl. No.: 17/430,719

(22) PCT Filed: Feb. 21, 2020

(86) PCT No.: PCT/JP2020/007000
§ 371 (c)(1),
(2) Date: Aug. 12, 2021

(87) PCT Pub. No.: WO2020/171199
PCT Pub. Date: Aug. 27, 2020

(65) Prior Publication Data
US 2022/0135874 A1   May 5, 2022

(30) Foreign Application Priority Data
Feb. 22, 2019   (JP) .................. 2019-030899

(51) Int. Cl.
C09K 11/06 (2006.01)
C07C 211/54 (2006.01)
H10H 20/851 (2025.01)

(52) U.S. Cl.
CPC ............ C09K 11/06 (2013.01); C07C 211/54 (2013.01); H10H 20/8512 (2025.01); C09K 2211/107 (2013.01); C09K 2211/1081 (2013.01)

(58) Field of Classification Search
CPC .............. C09K 11/06; C09K 2211/107; C09K 2211/1081; C07C 211/54; H01L 33/502
See application file for complete search history.

(56) References Cited

U.S. PATENT DOCUMENTS

| | | | | |
|---|---|---|---|---|
| 11,774,653 B2 * | 10/2023 | Watanabe | ............ | H05B 33/12 |
| | | | | 345/156 |
| 11,944,007 B2 * | 3/2024 | Thompson | ............ | C09B 57/008 |
| 2013/0147345 A1 * | 6/2013 | Maeda | .................. | H10F 77/45 |
| | | | | 313/503 |
| 2017/0117444 A1 * | 4/2017 | Stoll | ...................... | H10K 50/86 |
| 2018/0234415 A1 * | 8/2018 | Fukuda | .................. | H04W 12/33 |
| 2020/0243774 A1 * | 7/2020 | Aotake | ................. | H10K 85/655 |
| 2021/0130617 A1 * | 5/2021 | Sawamura | .............. | G03F 7/031 |
| 2022/0059790 A1 * | 2/2022 | Watanabe | ............ | H10K 85/371 |
| 2022/0185974 A1 * | 6/2022 | Nakabayashi | ............. | C08J 5/18 |

FOREIGN PATENT DOCUMENTS

| | | | | | |
|---|---|---|---|---|---|
| CN | 102372670 A | * | 3/2012 | | |
| JP | 03288860 | * | 4/1990 | | |
| JP | 2008145480 A | * | 6/2008 | | |
| JP | 2009-263614 A | | 11/2009 | | |
| JP | 2018111672 A | * | 7/2018 | | |
| JP | 2018133334 A | * | 8/2018 | ............. | H01R 13/46 |
| JP | 2018-172398 | * | 9/2018 | | |
| KR | 2018107968 | * | 10/2018 | | |
| WO | WO-2018207776 A1 | * | 11/2018 | ............... | G09F 9/30 |
| WO | WO-2019031456 A1 | * | 2/2019 | ............... | C07F 5/02 |
| WO | WO-2020013089 A1 | * | 1/2020 | ......... | C09B 23/0066 |
| WO | WO-2020054627 A1 | * | 3/2020 | | |

OTHER PUBLICATIONS

S. Tsai et al., 170 Journal of Photochemistry & Photobiology, B: Biology, 197-207 (2017) (Year: 2017).*
L. Winfield et al., 96 Journal of Chemical Education, 89-92 (2018) (Year: 2018).*
J. Shan et al., 63 Journal of Photochemistry and Photobiology A, 139-147 (1992) (Year: 1992).*
S. Wang et al., 23 Chemistry of Materials, 4879-4798 (2011) (Year: 2011).*
IUPAC, Compendium of Chemical Terminology, Gold Book, pp. 60, 73, 364, and 1538 of 1622 (2014) (Year: 2014).*
S. Yagi et al., Squarylium dyes and related compounds in, Heterocyclic Polymethine Dyes: Synthesis, Properties and Applications, 133-181 (2008) (Year: 2018).*
F. Ye et al., 171 Dyes and Pigments (2019) (Year: 2019).*
B. Hu et al., 30 Synlett, 1111-1124 (2019) (Year: 2019).*
S. Mula et al., 73 Journal of Organic Chemistry, 2146-2154 (2008) (Year: 2008).*

(Continued)

*Primary Examiner* — Alexander R Pagano
(74) *Attorney, Agent, or Firm* — LUCAS & MERCANTI, LLP

(57) ABSTRACT

An infrared-emitting compound has a structure represented by the following Formula (1a). In Formula (1a), Ar and ring A each independently represent an aryl ring, a heteroaryl ring or a fused ring thereof. Q-Ar represents an infrared-emitting residue. $R_1$ represents a group in which a dihedral angle between Ar and ring A is 45 degree or more. And a thick line represents a single bond or a double bond.

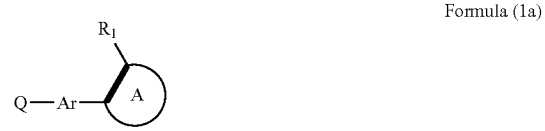

Formula (1a)

8 Claims, 2 Drawing Sheets

(56) References Cited

OTHER PUBLICATIONS

M. Mojzych et al., Synthesis of Cyanine Dyes in, Heterocyclic Polymethine Dyes: Synthesis, Properties and Applications, 1-9 (2008) (Year: 2008).*

CAS Abstract and Indexed Compounds, Y. Akao et al., JP 03288860 (1991) (Year: 1991).*

Office Action dated Sep. 19, 2023 for the corresponding Japanese Application No. 2021-502174, with English translation.

PCT, Written Opinion of ISA for the corresponding application No. PCT/JP2020/007000, dated May 26, 2020, with English translation.

PCT, International Search Report for the corresponding application No. PCT/JP2020/007000, dated May 26, 2020, with English translation.

T. Yamanaka, et al., "Near-infrared organic light-emitting diodes for biosensing with high operating stability," Applied Physics Express 10, Jun. 7, 2017, The Japan Society of Applied Physics.

S. Wang, et al., "N,N-Diarylanilinosquaraines and Their Application to Organic Photovoltaics," Chemistry of Materials, Oct. 18, 2011, pp. 4789-4798, vol. 23, American Chemical Society.

D. H. Kim, et al., "High-efficiency electroluminescence and amplified spontaneous emission from a thermally activated delayed fluorescent near-infrared emitter," Nature Photonics, 2018, Macmillan Publishers Limited.

* cited by examiner

INFRARED-EMITTING COMPOUND, AND LUMINESCENT THIN FILM, LUMINESCENT PARTICLE, WAVELENGTH CONVERSION FILM AND INFRARED-EMITTING SURFACE LIGHT SOURCE CONTAINING SAME

CROSS REFERENCE TO RELATED APPLICATION

This Application is a 371 of PCT/JP2020/007000 filed on Feb. 21, 2020, which claims priority of Japanese patent application no. 2019-030899 filed Feb. 22, 2019, the above applications are incorporated herein by reference.

TECHNICAL FIELD

The present invention relates to an infrared-emitting compound, and a luminescent thin film, luminescent particles, a wavelength conversion film, and an infrared-emitting surface light source containing the same compound. More particularly, the present invention relates to an infrared-emitting compound which enables long wavelength emission and high emission quantum yield.

BACKGROUND

In recent years, infrared-emitting materials have attracted considerable attention from the viewpoint of their use in infrared cameras, biometric imaging, biometric sensing, and infrared communication. For example, a pulse oximeter, which is one of biological sensing, uses infrared light to calculate oxygen saturation in blood (refer to Non-Patent Document 1). In addition, it has been studied as a sensitizer for organic solar cells (refer to Non-Patent Document 2). With the expansion of the application field of infrared light, the requirements are becoming stricter with respect to the performance required for infrared-emitting materials.

For example, although there are various emission wavelengths that are more suitable for use in biometric sensing, a material having a high luminance in a wavelength band that is easily transmitted through a living body, which is called a "window of living body" having a wavelength of 650 to 900 nm, is preferably used. When light is excited from the outside, an infrared-emitting compound having a high molar extinction coefficient, a longer emission wavelength, and a high emission quantum yield is required.

However, compounds that emit infrared light generally have a problem in that the nonradiative deactivation is apt to occur because the energy difference between the excited state and the ground state is small, and the luminescence quantum yield is low as compared with a fluorescent material that emits visible light. The longer the emission wavelength, the more pronounced the tendency to decrease the emission quantum yield. In Non-Patent Document 3, a decrease in external quantum efficiency caused by a low quantum yield of a fluorescent dye is also shown in organic electroluminescence (organic EL) using an infrared-emitting organic dye as the emission wavelength becomes longer. There are few reports on the longer wavelength of infrared light emission and the improvement of emission quantum yield. As an example of a fluorescent dye exhibiting infrared emission. Non-Patent Document 2 describes squarylium compounds R-1 to R-3 having the following structures.

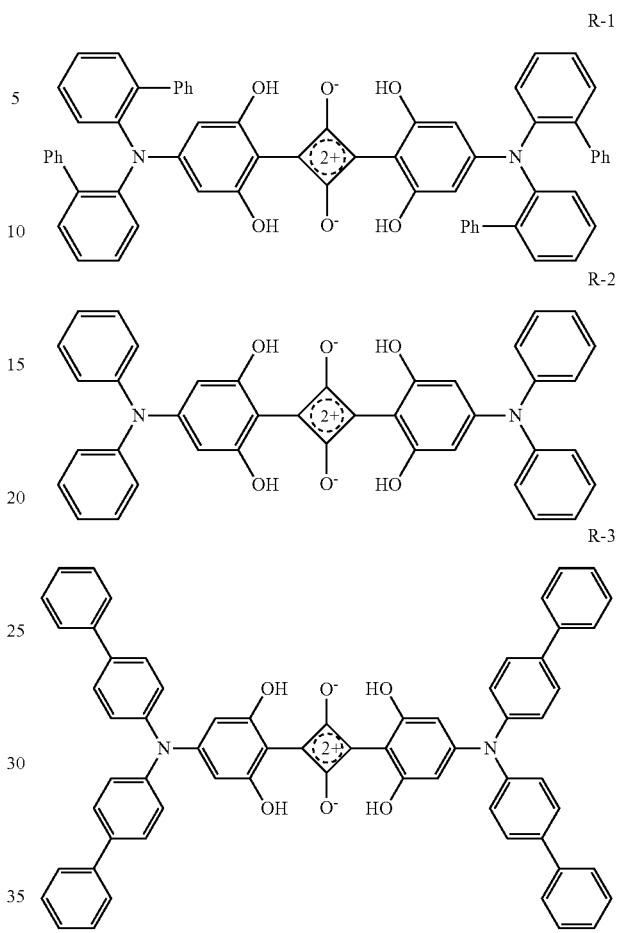

The maximum emission wavelength in the solution (toluene) of R-1 is 721 nm, and the emission quantum yield is 66%, whereas R-2 is extended to 750 nm, but the emission quantum yield is 29% which is less than half of R-1, and R-3 has the maximum emission wavelength of 786 nm, but the emission quantum yield is drastically reduced to 2% It is disclosed how it is difficult to achieve both long wavelength emission in the infrared region and high quantum yield.

Among near-infrared light of 650 to 900 nm called a biological window, it is known that the biological permeability of near-infrared light increases as it approaches 900 nm, and for application such as phototherapy and vein authentication, in particular, infrared-emitting compounds having a maximum emission long wavelength exceeding 750 un and capable of achieving both high emission quantum yield have been demanded.

PRIOR ART DOCUMENTS

Non-Patent Document

Non-Patent Document 1. T Yamanaka, et al., Applied Physics Express 10, 074101 (2017).

Non-Patent Document 2: S. Wang, et al., Chem. Mater, 2011, 23, 4789.

Non-Patent Document 3: D. H. Kim, et al., Nat. Photon, 2018, 12, 98, Supplementary Fig. S1b.

SUMMARY OF THE INVENTION

Problems to be Solved by the Invention

The present invention has been made in view of the above problems and status. An object of the present invention to provide an infrared-emitting compound capable of emitting light of a long wavelength and high emission quantum yield. Another object of the present invention is to provide a luminescent thin film, luminescent particles, a wavelength conversion film containing the same, and an infrared-emitting surface light source provided with the wavelength conversion film.

Means to Solve the Problems

In order to solve the above problem, the present inventor has found that the above problem is solved by introducing a specific substituent into an infrared-emitting compound in a process of examining a cause of the above problem, and has reached the present invention. In other words, the above problem according to the present invention is solved by the following means.

1. An infrared-emitting compound having a structure represented by the following Formula (1a).

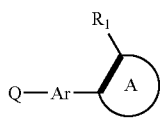

Formula (1a)

In Formula (1a), Ar and ring A each independently represent an aryl ring, a heteroaryl ring or a fused ring thereof. Q-Ar represents an infrared-emitting residue. $R_1$ represents a group in which a dihedral angle between Ar and ring A is 45 degree or more. A thick line represents a single bond or a double bond.

2. The infrared-emitting compound described in item 1, wherein the structure represented by Formula (1a) is a structure represented by the following Formula (1b) or Formula (1c).

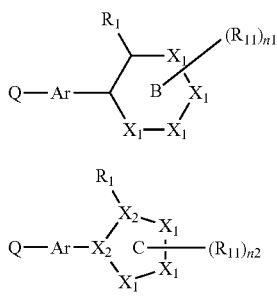

Formula (1b)

Formula (1c)

In Formula (1b) and Formula (1c), Ar represents an aryl ring, a heteroaryl ring or a fused ring thereof. Ring B represents an aromatic 6-numbered ring. Ring C represents an aromatic 5-membered ring. $X_1$ each independently represents an atom selected from a carbon atom, a nitrogen atom, an oxygen atom, and a sulfur atom. $X_2$ each independently represents an atom selected from a carbon atom and a mitogen atom. Q-Ar represents an infrared-emitting residue. $R_1$ represents a group in which a dihedral angle between Ar and ring B is 45 degree or more. $R_{11}$ represents a substituent, and $R_{11}$ may form a ring with an adjacent Rr, or a plurality of $R_{11}$s may form a ring. n1 represents an integer of 0 to 4; and n2 represents an integer of 0 to 3.

3. The infrared-emitting compound described in item 1, wherein the structure represented by Formula (1a) is a structure represented by the following Formula (1d) or Formula (1e).

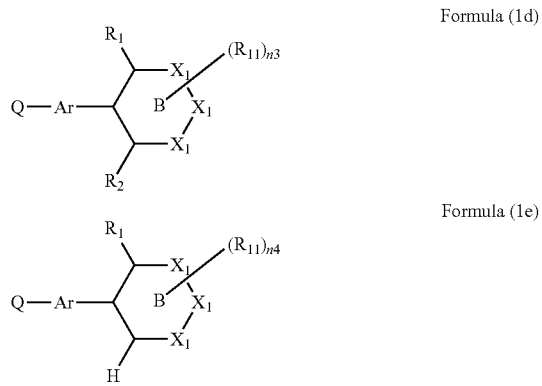

In Formula (1d) and Formula (1e). Ar represents an aryl ring, a heteroaryl ring or a fused ring thereof. Ring B represents an aromatic 6-membered ring. $X_1$ each independently represents an atom selected from a carbon atom, a nitrogen atom, an oxygen atom, and a sulfur atom. Q-Ar represents an infrared-emitting residue. $R_1$ represents a group in which a dihedral angle between Ar and ring B is 45 degree or more. $R_2$ and $R_{11}$ each independently represent a substituent. $R_{11}$ and an adjacent $R_1$ or $R_2$ may form a ring, or a plurality of $R_{11}$s may form a ring. n3 and n4 each independently represent an integer of 0 to 3.

4 The infrared-emitting compound described in any one of items 1 to 3, wherein $R_1$ each independently represents an alkyl group, an alkoxy group, an amino group, an aryl group, a heteroaryl group, a phenoxy group, an alkylthio group, a carbonyl group or a carboxy group.

5. The infrared-emitting compound described in item 2 or 3, wherein $R_{11}$ each independently represents an alkyl group, an alkoxy group, an amino group, an aryl group, a heteroaryl group, a phenoxy group, an alkylthio group, a carbonyl group or a carboxy group.

6. The infrared-emitting compound described in item 3, wherein $R_2$ each independently represents an alkyl group, an alkoxy group, an amino group, an aryl group, a heteroaryl group, a phenoxy group, an alkylthio group, a carbonyl group or a carboxy group.

7. The infrared-emitting compound described in any one of items 1 to 3, wherein the infrared-emitting residue represented by Q-Ar is a residue of a squarylium dye, a dye containing benzobisthiadiazole, a dye containing thiadiazoloquinoxaline, a pyrromethene dye or a cyanine dye.

8. The infrared-emitting compound described in item 1, wherein the compound having a structure represented by Formula (1a) is a compound having a structure represented by the following Formula (2a), (3a), (4a), (5a), (6a), (7a), or (8a).

Formula (2a)

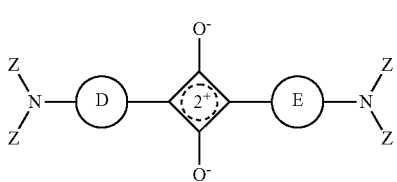

Formula (3a)

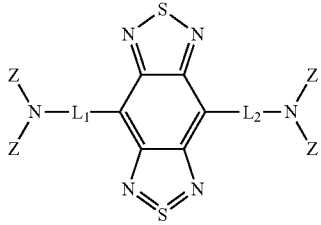

Formula (4a)

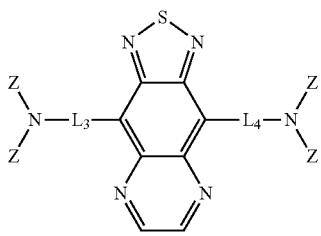

Formula (5a)

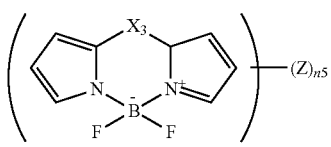

Formula (6a)

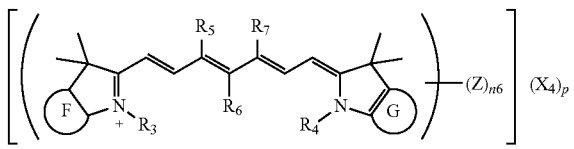

Formula (7a)

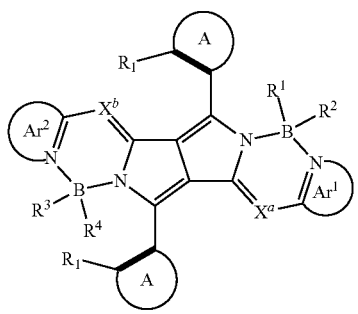

Formula (8a)

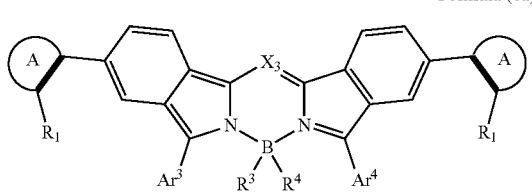

In Formula (2a) to Formula (8a), ring D and ring E each independently represent an aryl ring which may be substituted with a hydroxy group, an alkoxy group, an NHCORa group (Ra represents a hydrocarbon group), an NHSO$_2$Rb group (Rb represents a hydrocarbon group), or an NHPO (ORf)(ORg) group (Rf and Rg each independently represent a hydrocarbon group). Ring F and ring G each independently represent an aryl ring. $L_1$ to $L_4$ each independently represent an aryl ring, a heteroaryl ring or a single bond. $X_3$ represents a carbon atom or a nitrogen atom which may be substituted with an aryl group. $R_3$ and $R_4$ each independently represent an alkyl group which may be substituted with a sulfo group. $R_5$ and $R_7$ each independently represent a hydrogen atom or an alkyl group. $R_6$ represents a hydrogen atom or an aryl group, and $R_5$ and $R_7$ may be bonded to forma cycloalkene ring when $R_5$ or $R_7$ represents an alkyl group. When a portion represented by IND is a cationic portion, $X_4$ represents a counter anion, p represents a number required to neutralize a charge, and when a portion represented by IND is an anionic portion, $X_4$ represents a counter cation, p represents a number required to neutralize the charge, and when the charge at a portion represented by IND is neutralized in the molecule, p represents 0. $Ar^1$ and $Ar^2$ each represent an aryl group composed of a 6-membered ring or a heteroaroyl group composed of 5-membered ring or 6-membered ring, and these groups may contain two or more rings. $X^a$ and $X^b$ each independently represent a nitrogen atom or $CR^5$, and $R^5$ represents a hydrogen atom or an electron withdrawing group. $R^1$ to $R^4$ each independently represents a cyano group, a halogen atom, an alkyl group that may be substituted, an alkoxy group that may be substituted, an alkynyl group that may be substituted, an aryl group that may be substituted, or a heteroaryl group that may be substituted. $Ar^3$ and $Ar^4$ each represent an aryl group composed of a 6-membered ring or a heteroaryl group composed of 5-membered ring or 6-membered ring, and these groups may contain two or more rings. Ring A each independently represents an aryl ring, a heteroaryl ring or a fused ring thereof. $R_1$ represents a group having a dihedral angle of 45 degree or more with a pyrrole ring or a benzene ring to which ring A is bonded, respectively. A thick line represents a single bond or a double bond. Z represents a group of the following Formula (Z) or a substituent, and at least one of Z represents the group of Formula (Z). n5 represents an integer of 1 to 4. n6 represents an integer of 1 to 4.

Formula (Z)

*—Ar—A (R$_1$)

In Formula (Z), ring A represents an aryl ring, a heteroaryl ring or a fused ring thereof. An asterisk (*) represents a binding site with Ar in a luminescent residue of Formula (1a). Rr represents a group in which a dihedral angle between Ar and ring A is 45 degree or more. A thick line represents a single bond or a double bond.

9. The infrared-emitting compound described in item 1, wherein the structure represented by Formula (1a) is a squarylium compound having a structure represented by the following Formula (2b).

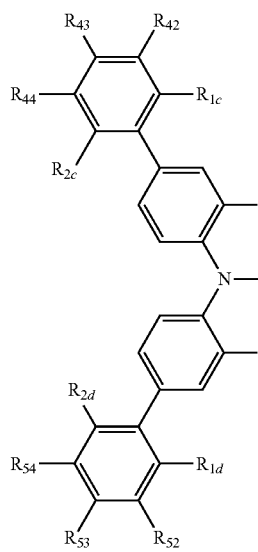
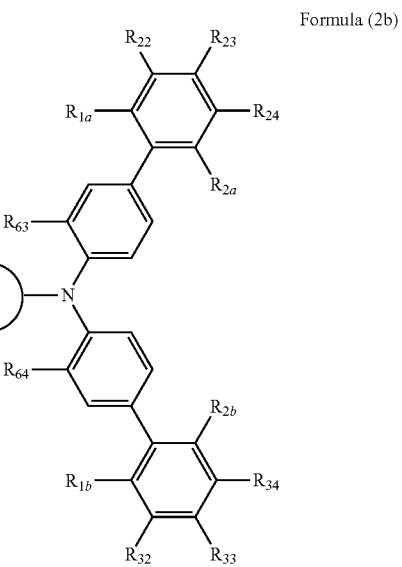

Formula (2b)

In Formula (2b), $R_{1a}$ to $R_{1d}$, $R_{2a}$ to $R_{2d}$, $R_{22}$ to $R_{24}$, $R_{32}$ to $R_{34}$, $R_{42}$ to $R_{44}$, $R_{52}$ to $R_{54}$, and $R_{63}$ to $R_{66}$, each independently represent a hydrogen atom, an alkyl group, an alkoxy group, a phenoxy group, an amino group, an aryl group, or a heteroaryl group, but at least one of the combinations of $R_{1a}$ and $R_{2a}$, $R_{1b}$ and $R_{2b}$, $R_{1c}$ and $R_{2c}$, and $R_{1d}$ and $R_{2d}$ does not both represent a hydrogen atom. $R_{1a}$ and $R_{22}$, $R_{2a}$ and $R_{24}$, $R_{1b}$ and $R_{32}$, $R_{2b}$ and $R_{34}$, $R_{1c}$ and $R_{42}$, $R_{2c}$ and $R_{44}$, $R_{1d}$ and $R_{52}$, and $R_{2d}$ and $R_{54}$ may be bonded to form a ring structure. Ring H and ring I each independently represent an aryl group which may be substituted with a hydroxy group, an alkoxy group, an NHCORa group (Ra represents a hydrocarbon group), an NHSO$_2$Rb group (Rb represents a hydrocarbon group), or an NHPO(ORf)(ORg) group (Rf and Rg each independently represent a hydrocarbon group).

10. The infrared-emitting compound described in item 9, wherein, in the squarylium compound having a structure represented by Formula (2b), $R_{1a}$ to $R_{1d}$ and $R_{2a}$ to $R_{2d}$ am the same and represent an alkyl group, an alkoxy group, a phenoxy group, an amino group, an aryl group or a heteroaryl group.

11. The infrared-emitting compound described in item 9 or 10, wherein, in the squarylium compound having a structure represented by Formula (2b), ring H and ring I are the same and represent an aryl group having a hydroxyl group, $R_{23}$, $R_{33}$, $R_{43}$ and $R_{53}$ are the same as $R_{1a}$ to $R_{1d}$ and $R_{2a}$ to $R_{2d}$, respectively, or represent a hydrogen atom, but at least one of the combinations of $R_{1a}$ and $R_{2a}$, $R_{1b}$ and $R_{2b}$, $R_{1c}$ and $R_{2c}$, and $R_{1d}$ and $R_{2d}$ does not both represent a hydrogen atom, and $R_{22}$, $R_{24}$, $R_{32}$, $R_{34}$, $R_{42}$, $R_{44}$, $R_{52}$ and $R_{54}$ represent a hydrogen atom.

12. The infrared-emitting compound described in item 9, wherein, in the squarylium compound having a structure represented by Formula (2b), ring H and ring I am the same and represent an aryl group having a hydroxy group; $R_{1a}$ is bonded to $R_{22}$, $R_{2a}$ is bonded to $R_{24}$, $R_{1b}$ is bonded to $R_{32}$, $R_{2b}$ is bonded to $R_{34}$, $R_{1c}$ is bonded to $R_{42}$, $R_{2c}$ is bonded to $R_{44}$, $R_{1d}$ is bonded to $R_{52}$, and $R_{2d}$ is bonded to $R_{54}$ respectively to form a 5-membered ring or a 6-membered ring with a carbon chain.

13. A luminescent thin film containing the infrared-emitting compound described in any one of items 1 to 12.
14. A luminescent particle containing the infrared-emitting compound described in any one of items 1 to 12.
15. A wavelength conversion film containing the infrared-emitting compound described in any one of items 1 to 12.
16. An infrared-emitting surface light source comprising the wavelength conversion film described in item 15.

Effects of the Invention

By the above-mentioned means of the present invention, it is possible to provide an infrared-emitting compound capable of emitting light of a long wavelength and a high luminescence quantum yield. In addition, it is possible to provide a luminescent thin film, luminescent particles, a wavelength conversion film containing the same, and an infrared-emitting surface light source provided with the wavelength conversion film. The expression mechanism or action mechanism of the effect of the present invention is not clarified, but is inferred as follows.

When the above-mentioned squarylium compound R-1 is made to emit light at longer wavelengths like R-2 and R-3, the emission quantum yield is extremely lowered. This is because the excited state in the emission in the infrared region has a small energy difference from the ground state, so that the influence of nonradiative deactivation due to expansion-contraction and vibration of molecular bonds becomes large. In the present invention, it has been found that by introducing a substituent having a specific aromatic ring capable of generating a dihedral angle in a stable structure of a molecule into an infrared emission site, the t conjugate system may be extended while suppressing molecular vibration, that is, high emission quantum yield and long wavelength emission may be compatible in the infrared region. By generating a dihedral angle in the stable structure of the molecular, it is presumed that the nonradiative deactivation is suppressed by suppressing the rotation and movement between Ar group of Formula (1a) and ring A. Further, a π-π conjugation system has been successfully extended by forming a σ-π conjugation between a group which produces a dihedral angle and a π-conjugation group (Ar group of Formula (1a)) which makes a dihedral angle. By introducing the present substituent into, for example, a squarylium compound, it is possible to provide an infrared-emitting compound capable of achieving both improvement in luminescence quantum yield and long-wavelength light emission.

Furthermore, it is possible to exhibit a high emission quantum yield because the concentration quenching in the film hardly occurs even when the luminescent thin film is formed due to the effect of the bulkiness of the substituent.

EMBODIMENTS TO CARRY OUT THE INVENTION

Figure 1:
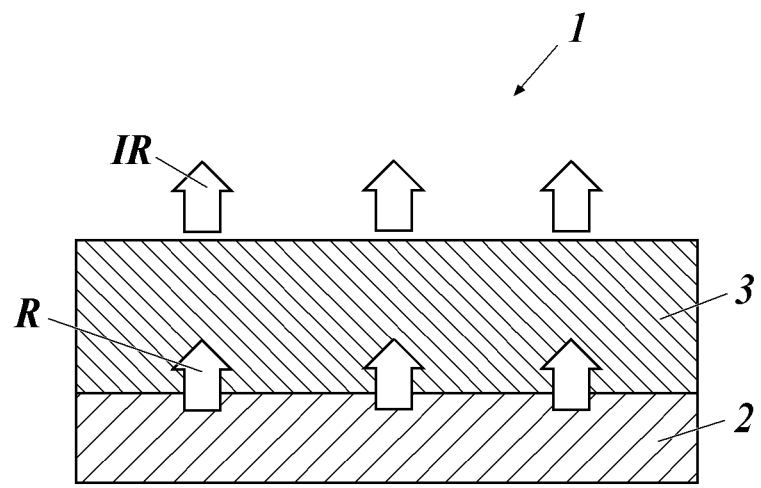
FIG. 1 is a schematic cross-sectional view showing an example of a configuration of an infrared-emitting surface light source comprising a wavelength conversion film of the present invention.

The infrared-emitting compound of the present invention is characterized in that it has a structure represented by the above Formula (1a). This feature is a technical feature common to or corresponding to each of the embodiments described below. As an embodiment of the present invention, from the viewpoint of expressing the effect of the present invention, it is preferable that the structure represented by the above Formula (1a) is a structure represented by the above Formula (1b) or Formula (1c). Further, it is preferable that the structure represented by Formula (1a) is a structure represented by Formula (1d) or Formula (1e).

In addition, it is preferred that $R_1$ represent an alkyl group, an alkoxy group, an amino group, an aryl group, a heteroaryl group, a phenoxy group, an alkylthio group, a carbonyl group or a carboxy group. Thus, a dihedral angle is generated between Ar and ring A in Formula (1a), Ar and ring B in Formula (1b), Ar and ring C in Formula (1c), Ar and ring B in Formula (1d), and Ar and ring B in Formula (1e), and an effect of molecular vibration suppression and a conjugation extension is obtained. In an embodiment of the present invention, it is preferable that $R_{11}$ independently represents an alkyl group, an alkoxy group, an amino group, an aryl group, a heteroaryl group, a phenoxy group, an alkylthio group, a carbonyl group or a carboxy group.

In addition, it is preferable that $R_2$ represents an alkyl group, an alkoxy group, an amino group, an aryl group, a heteroaryl group, a phenoxy group, an alkylthio group, a carbonyl group or a carboxy group, because the fixing of the dihedral angle between Ar and ring B in the above Formula (1d) may be further strengthened and the effect of enhancing the suppression of the molecular vibration may be obtained. Further, in the present invention, it is preferable that the infrared-emitting residue represented by Q-Ar of Formula (1a) is a residue of a squarylium dye, a dye containing benzobisthiadiazole, a dye containing thiadiazoloquinoxaline, a pyrromethene dye or a cyanine dye. It is preferable that the compound having a structure represented by Formula (1a) is a compound having a structure represented by the above Formula (2a), (3a), (4a), (5a), (6a), (7a) or (8a). Further, it is preferable that the compound having a structure represented by Formula (1a) is a squarylium compound having a structure represented by Formula (2b) described above.

Further, in the present invention, in the squarylium compound having a structure represented by Formula (2b), it is preferable that $R_{1a}$ to $R_{1d}$ and $R_2$, to $R_{2d}$ are the same and represent an alkyl group, an alkoxy group, a phenoxy group, an amino group, an aryl group or a heteroaryl group. In the squarylium compound having a structure represented by the Formula (2b), ring H and ring I am the same and represent an aryl group having a hydroxyl group, and $R_{23}$, $R_{33}$, $R_{43}$ and $R_{53}$ are the same as $R_{1a}$ to $R_{1d}$ and $R_{2a}$ to $R_{2d}$ or a hydrogen atom, respectively, but at least one of the combinations of $R_{1a}$ and $R_{2a}$, $R_{1b}$ and $R_{2b}$, $R_{1c}$ and $R_{2c}$, and $R_{1d}$ and $R_{2d}$ does not both represent a hydrogen atom, and $R_{22}$, $R_{24}$, $R_{32}$, $R_{34}$, $R_{42}$, $R_{44}$, $R_{52}$ and $R_{54}$ represent a hydrogen atom. Further, in the squarylium compound having a structure represented by the above Formula (2b), ring H and ring I preferably each independently represent an aryl ring which may be substituted with a hydroxy group, an alkoxy group, an NHCORa group (Ra represents a hydrocarbon group), an NHSO$_2$Rb group (Rb represents a hydrocarbon group) or an NHPO(ORf)(ORg) group (Rf and Rg each independently represents a hydrocarbon group). Preferably, ring H and ring I are the same and represent an aryl group having a hydroxyl group, and Rr, and Rn, $R_2$, and Ru, $R_{1b}$ and $R_{32}$, $R_{2b}$ and $R_{34}$, $R_{1c}$ and $R_{42}$, $R_{2c}$ and $R_{44}$, $R_{1d}$ and $R_{52}$, and $R_{2d}$ and $R_{54}$ may be bonded respectively to form a 5-membered ring or a 6-membered ring with a carbon chain. In addition, it is preferable to use a luminescent thin film, luminescent particles, or a wavelength conversion film containing the infrared-emitting compound of the present invention. Further, it is preferable that the infrared-emitting surface light source is provided with the wavelength conversion film.

Hereinafter, the present invention, its constituent elements, and configurations and embodiments for carrying out the present invention will be described in detail. In the present application, "to" is used in the meaning that the numerical values described before and after "to" are included as a lower limit value and an upper limit value. In the present invention, the infrared-emitting compound means a compound having an emission maximum wavelength of more than 700 nm.

<<Infrared-Emitting Compound>>

[Structure Represented by Formula (1a)]

The infrared-emitting compound of the present invention is characterized in that it has a structure represented by the following Formula (1a).

Formula (1a)

In Formula (1a), Ar and ring A each independently represents an aryl ring, a heteroaryl ring or a fused ring thereof. Q-Ar represents an infrared-emitting residue. $R_1$ represents a group in which a dihedral angle between Ar and ring A is 45 degree or more. A thick line represents a single bond or a double bond.

By introducing a group (also referred to as a substituent according to the present invention) having ring A substituted with $R_1$, which generates such a dihedral angle, into an infrared-emitting residue having Ar, it is possible to obtain an infrared-emitting compound of the present invention, which can expand a conjugate system while suppressing molecular vibration, and which can emit light of a long wavelength and a high emission quantum yield.

It is preferable that the infrared-emitting compound of the present invention has a plurality of substituents according to the present invention. The number of substituents according to the present invention may be, for example, 1 to 8 per molecule, and preferably, 1 to 4.

In the present invention, the dihedral angle formed by Ar and ring A is 45 degree or more, and more preferably 60 degree or more. The upper limit is 90 degree.

In Formula (1a). Ar and ring A represent an aryl ring, a heteroaryl ring or a fused ring thereof.

Specific examples of the aryl ring include a benzene ring, an indene ring, a naphthalene ring, an azulene ring a fluorene ring, a phenanthrene ring, an anthracene ring, an acenaphthylene ring, a biphenylene ring, a chrysene ring, a naphthalene ring, a pyrene ring, a penthalene ring, an aceanthrylene ring, a triphenylene ring, an as-indacene ring, a chrysene ring, an s-indacene ring, a preiadene ring, a phenalene ring, a fluoranthene ring, a perylene ring, an acephenanthrylene ring, a biphenyl ring, a terphenyl ring, and a tetraphenyl ring.

Examples of the heteroaryl ring include a pyridine ring, a pyrimidine ring, a furan ring, a pyrrole ring, an imidazoline ring, a benzoimidazoline ring, a pyrazole ring, a pyrazine ring, a triazole ring (for example, 1,2,4-triazole ring, 1,2,3-triazole ring, a pyrazolotriazole ring, an oxazole ring, a benzoxazole ring, a thiazole ring, an isoxazole ring, an isothiazole ring, a furazan ring, a thiophene ring, a quinoline ring, a benzofuran ring, a dibenzofuran ring, a benzothiophene ring, a dibenzothiophene ring, an indole ring, a carbazole ring, a carboline ring, a diazacarbazole ring (indicating one in which one of the carbon atoms constituting the carboline ring is replaced with a nitrogen atom), a quinoxaline ring, a pyridazine ring, a triazole ring, a quinazoline ring, a phthalazine ring, a 9,10-dihydroacryzine ring, a phenoxazine ring, a phenothiazine ring, and a dibenzosilole ring.

$R_1$ represents a group in which a dihedral angle between Ar and ring A is 45 degree or more. Specifically, $R_1$ is not particularly limited as long as it is a group having a dihedral angle of 45 degree or more by measuring the dihedral angle to be described later. Preferred groups are an alkyl group, an alkoxy group, an amino group, an aryl group, a heteroaryl group, a phenoxy group, an alkylthio group, a carbonyl group or a carboxy group. Examples of the alkyl group include a methyl group, an ethyl group, an n-propy l group, an isopropyl group, an n-butyl group, an s-butyl group, a t-butyl group, a 2-ethylbutyl group, an n-pentyl group, a neopentyl group, an n-hexyl group, a cyclohexyl group, a 2-ethylhexyl group, an n-heptyl group, an n-octyl group, a 2-butyloctyl group, a 2-hexyloctyl group, an n-nonyl group, an n-decyl group, a 2-hexyldecyl group, an n-undecyl group, an n-dodecyl group, a 2-octyldodecyl group, an n-tridecyl group, an n-tetradecyl group, a 2-decyltetradecyl group, an n-pentadecyl group, an n-hexadecyl group, an n-heptadecyl group, an n-octadecyl group, an n-nonadecil group, and an n-eicosyl group.

Examples of the alkoxy group include a methoxy group, an ethoxy group, an n-propyloxy group, an isopropyloxy group, an n-butyloxy group, an s-butyloxy group, a t-butyloxy group, a 2-ethylbutyloxy group, an n-pentyloxy group, a neopentyloxy group, an n-hexyloxy group, a cyclohexyloxy group, a 2-ethylhexyloxy group, an n-heptyloxy group, an n-octyloxy group, a 2-butyloctyloxy group, a 2-hexyloctyloxy group, an n-nonyloxy group, an n-decyloxy group, a 2-hexyldecyloxy group, an n-undecyloxy group, an n-dodecyloxy group, a 2-octyldodecyloxy group, an n-tridecyloxy group, an n-tetradecyloxy group, a 2-decyltetmdecyloxy group, an n-pentadecyloxy group, an n-hexadecyloxy group, an n-heptadecyloxy group, an n-octadecyloxy group, an n-nonadecyloxy group, and an n-eicosyloxy group.

Examples of the amino group include an amino group, an alkylamino group (e.g., an ethylamino group), a dialkylamino group (e.g., a dimethylamino group, a diethylamino group, a diisopropylamino group, a di-n-propylamino group, a di-n-butylamino group, a di-s-butylamino group, a di-2-ethylbutylamino group, a di-2-ethylhexylamino group, a didodecylamino group, a dicyclopentylamino group, and a dicyclohexylamino group), an arylamino group (e.g., a phenylamino group), and a diarylamino group (e.g., a diphenylamino group, a dinaphthylamino group).

Examples of the aryl group include a group obtained by removing 1 hydrogen atom from the above-described aryl ring. Examples of the heteroaryl group include a group obtained by removing 1 hydrogen atom from the above-described heteroaryl ring.

Examples of the alkylthio group include a methylthio group, an ethylthio group, a propylthio group, a pentylthio group, a hexylthio group, an octylthio group, and a dodecylthio group.

Examples of the carbonyl group include an acyl group (e.g., an acetyl group, an ethylcarbonyl group, an n-propylcarbonyl group, and a cyclohexylcarbonyl group). Examples of the carboxy group include an alkylcarboxy group (e.g., a methylcarboxy group and an ethylcarboxy group), an arylcarboxy group (e.g., a phenylcarboxy group).

Also, these groups may be further substituted by the above groups. Of these. Ar and ring A preferably represent an aryl ring, a heteroaryl ring or a fused ring thereof, and more preferably an aryl ring. It is preferred that $R_1$ represents a alkyl group, an alkoxy group, an amino group, an aryl group, a heteroaryl group, a phenoxy group, an alkylthio group, a carbonyl group or a carboxy group, and more preferably $R_1$ represents a alkyl group, an alkoxy group, or an amino group.

Q-Ar represents an infrared-emitting residue. As a preferred luminescent residue, it is preferable to be a group having a skeleton of a squarylium dye, a dye containing benzobisthiadiazole, a dye containing thiadiazoloquinoxaline, a pyrromethene dye or a cyanine dye, respectively. In other words, it is preferable that the compound having a structure represented by the above Formula (1a) is a squarylium dye, a dye containing benzobisthiadiazole, a dye containing thiadiazoloquinoxaline, a pyrromethene dye or a cyanine dye.

[Dihedral Angle]

In the present invention, the dihedral angle may be calculated as follows. In Formula (1a), $R_1$ represents a group in which a dihedral angle between Ar and ring A is 45 degree or more. The dihedral angle between Ar and ring A in the present invention refers to a dihedral angle calculated by structural optimization with molecular orbital calculation. Specifically, in the molecular orbital computation for performing structural optimization, it is derived using B3LYP as a functional and 6-31G* as a basis function. Gaussian09 (Revision C. 01, M. J. Frisch, et al., Gaussian, Inc., 2010) manufactured by Gaussian Corporation, U.S.A. may be used as the molecular orbital calculating software. The dihedral angle obtained by this computational method represents the stable structure in the real molecule.

Optimization calculation

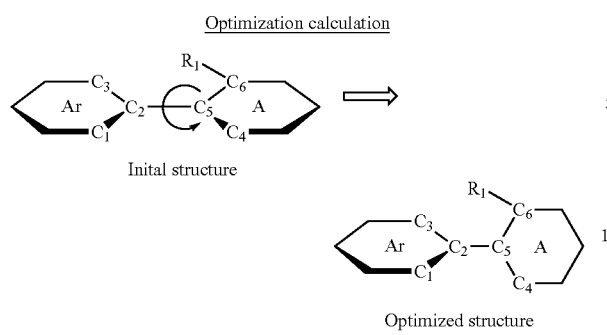

Initial structure

Optimized structure

For example, when Ar is a benzene ring and ring A is a benzene ring as described above, the dihedral angle of $C_1$-$C_2$-$C_5$-$C_4$, the dihedral angle of $C_1$-$C_2$-$C_5$-$C_6$, the dihedral angle of $C_3$-$C_2$-$C_5$-$C_4$, and the dihedral angle of $C_3$-$C_2$-$C_5$-$C_6$, are indicated by 0 to 90 degree. By using the compound having the average of the four dihedral angles of the initial structure of 0 degree, the structure optimization is performed, and the dihedral angle according to the present invention may be calculated by averaging $C_1$-$C_2$-$C_5$-$C_4$ dihedral angle. $C_1$-$C_2$-$C_5$-$C_6$ dihedral angle, $C_3$-$C_2$-$C_5$-$C_4$ dihedral angle, and $C_3$-$C_2$-$C_5$-$C_6$ dihedral angle of the resulting structure.

[Structure Represented by Formula (1b) or Formula (1c)]

The structure represented by the above Formula (1a) is preferably a structure represented by the following Formula (1b) or Formula (1c).

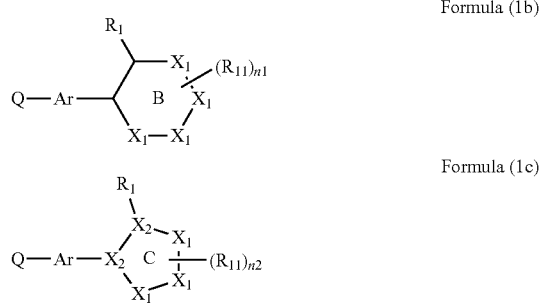

Formula (1b)

Formula (1c)

In Formula (1b) and Formula (1c), Ar represents an aryl ring, a heteroaryl ring or a fused ring thereof. Ring B represents an aromatic 6-membered ring. Ring C represents an aromatic 5-membered ring. $X_1$ each independently represents an atom selected from a carbon atom, a nitrogen atom, an oxygen atom, and a sulfur atom. $X_2$ each independently represents an atom selected from a carbon atom and a nitrogen atom. Q-Ar represents an infrared-emitting residue. $R_1$ represents a group in which a dihedral angle between Ar and ring B is 45 degree or more. $R_{11}$ represents a substituent, and $R_{11}$ may form a ring with an adjacent $R_1$, or a plurality of $R_{11}$s may form a ring. n1 represents an integer of 0 to 4; and n2 represents an integer of 0 to 3.

Ar, $R_1$ and Q-Ar are synonymous with Ar, $R_1$ and Q-Ar in Formula (1a), respectively. Ring B represents an aromatic 6-membered ring. Specifically, it represents a group of a 6-membered ring among an aryl ring and a heteroaryl ring, listed in Formula (1a). Ring C represents an aromatic 5-membered ring. Specifically, it represents a group of a 5-membered ring among heteroaryl rings mentioned in Formula (1a).

$X_1$ each independently represents an atom selected from a carbon atom, a nitrogen atom, an oxygen atom, and a sulfur atom. $X_2$ each independently represents an atom selected from a carbon atom and a nitrogen atom. $R_{11}$ represents a substituent, and $R_{11}$ may form a ring with an adjacent $R_1$, or a plurality of $R_{11}$s may form a ring. Examples of the substituent represented by $R_{11}$ include similar substituents represented by $R_1$, and the same ones are preferable. n1 represents an integer of 0 to 4. n2 represents an integer of 0 to 3.

[Formula (1d) and Formula (1e)]

The structure represented by the above Formula (1a) is preferably a structure represented by the following Formula (1d) or Formula (1e).

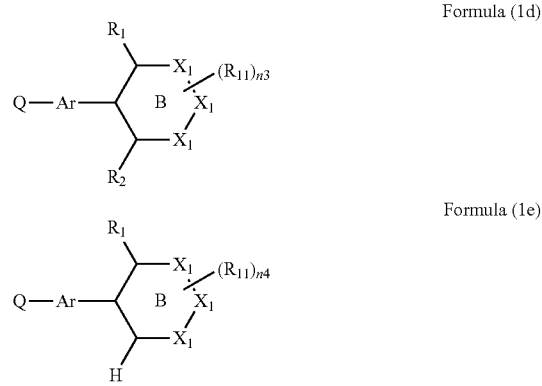

Formula (1d)

Formula (1e)

In Formula (1d) and Formula (1e), Ar represents an aryl ring, a heteroaryl ring or a fused ring thereof. Ring B represents an aromatic 6-membered ring. $X_1$ each independently represents an atom selected from a carbon atom, a nitrogen atom, an oxygen atom, and a sulfur atom. Q-Ar represents an infrared-emitting residue. $R_1$ represents a group in which a dihedral angle between Ar and ring B is 45 degree or more. $R_2$ and $R_{11}$ each independently represent a substituent, $R_{11}$ and an adjacent $R_1$ or $R_2$ may forma ring, or a plurality of $R_{11}$s may form a ring. n3 and n4 each independently represent an integer of 0 to 3.

Examples of the substituent represented by $R_2$ include similar substituents represented by $R_1$, and the same ones are preferable. Ar, ring B, $X_1$, Q-Ar, $R_1$ and $R_{11}$ are synonymous with Ar, ring B, $X_1$, Q-Ar, $R_1$ and $R_{11}$ described in Formula (1b) and Formula (1c). $R_2$ represents a substituent. As substituents, the substituents described in $R_{11}$ nay be applied, but it is preferred to represent an alkyl group, an alkoxy group, an amino group, an aryl group, a heteroaryl group, a phenoxy group, an alkylthio group, a carbonyl group or a carboxy group. n3 and n4 each respectively represent integer of 0 to 3.

[Compounds Represented by Formula (2a), (3a), (4a), (5a), (6a), (7a) and (8a)]

It is preferable that the compound having a structure represented by Formula (1a) is a compound having a structure represented by the following Formulas (2a), (3a), (4a), (5a), (6a), (7a) or (8a).

Formula (2a)
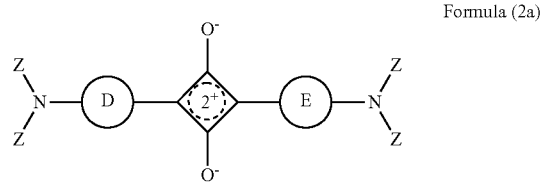

Formula (3a)
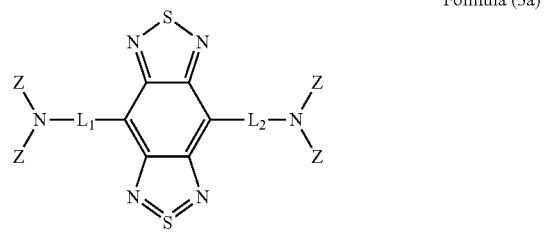

Formula (4a)
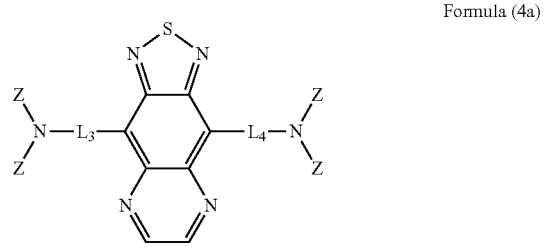

Formula (5a)
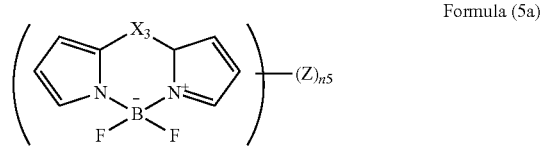

Formula (6a)
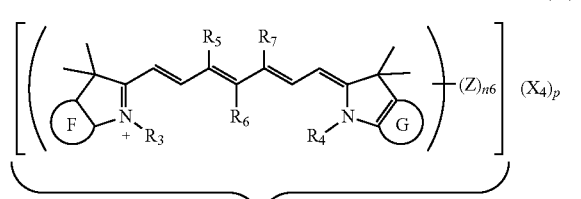

IND

Formula (7a)
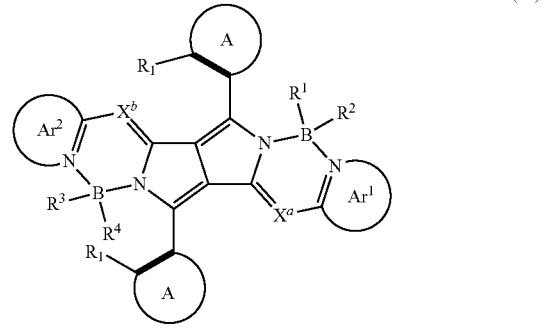

Formula (8a)
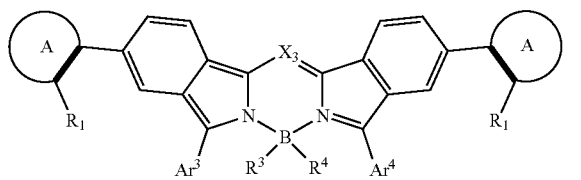

In Formula (2a) to Formula (8a), ring D and ring E each independently represent an aryl ring which may be substituted with a hydroxy group, an alkoxy group, an NHCORa group (Ra represents a hydrocarbon group), an $NHSO_2Rb$ group (Rb represents a hydrocarbon group), or an NHPO(ORf)(ORg) group (Rf and Rg each independently represent a hydrocarbon group). Ring F and ring G each independently represent an aryl ring. $L_1$ to $L_4$ each independently represent an aryl ring, a heteroaryl ring or a single bond. $X_3$ represents a carbon atom or a nitrogen atom which may be substituted with an aryl group. $R_3$ and $R_4$ each independently represent an alkyl group which may be substituted with a sulfo group. $R_5$ and $R_7$ each independently represent a hydrogen atom or an alkyl group. $R_6$ represents a hydrogen atom or an aryl group, and $R_5$ and $R_7$ may be bonded to form a cycloalkene ring when $R_5$ or $R_7$ represents an alkyl group. When a portion represented by IND is a cationic portion, $X_4$ represents a counter anion, p represents a number required to neutralize a charge, and when a portion represented by IND is an anionic portion, $X_4$ represents a counter cation, p represents a number required to neutralize the charge, and when the charge at a portion represented by IND is neutralized in the molecule, p represents 0. $Ar^1$ and $Ar^2$ each represent an aryl group composed of a 6-membered ring or a heteroaryl group composed of 5-membered ring or 6-membered ring, and these groups may contain two or more rings. $X^a$ and $X^b$ each independently represent a nitrogen atom or $CR^5$, and $R^5$ represents a hydrogen atom or an electron withdrawing group. $R^1$ to $R^4$ each independently represents a cyano group, a halogen atom, an alkyl group that may be substituted, an alkoxy group that may be substituted, an alkynyl group that may be substituted, an aryl group that may be substituted, or a heteroaryl group that may be substituted. $Ar^3$ and $Ar^4$ each represent an aryl group composed of a 6-membered ring or a heteroaryl group composed of 5-membered ring or 6-membered ring, and these groups may contain two or more rings. Ring A each independently represents an aryl ring, a heteroaryl ring or a fused ring thereof. $R_1$ represents a group having a dihedral angle of 45 degree or more with a pyrrole ring or a benzene ring to which ring A is bonded, respectively. A thick line represents a single bond or a double bond. Z represents a group of the following Formula (Z) or a substituent, and at least one of Z represents the group of Formula (Z). n5 represents an integer of 1 to 4. n6 represents an integer of 1 to 4.

Formula (Z)

In Formula (Z), ring A represents an aryl ring, a heteroaryl ring or a fused ring thereof. An asterisk (*) represents a binding site with Ar in a luminescent residue of Formula (1a). $R_1$ represents a group in which a dihedral angle between Ar and ring A is 45 degree or more. A thick line represents a single bond or a double bond.

Ring D and ring E each independently represents an aryl ring which may be substituted with a hydroxy group or an alkoxy group. Ring F and ring G each independently represents an aryl ring. $L_1$ to $L_4$ each independently represents an aryl ring, a heteroaryl ring or a single bond. The aryl ring represented by the above rings D to G and the aryl ring and heteroaryl ring represented by $L_1$ to $L_4$ may be an aryl ring or a heteroaryl ring described in Formula (1a). $X_3$ represents a carbon atom or a nitrogen atom which may be substituted with an aryl group. $R_3$ and $R_4$ each independently represent an alkyl group which may be substituted with a sulfo group. $R_5$ and $R_7$ each independently represents a hydrogen atom or an alkyl group. $R_6$ represents a hydrogen atom or an aryl group, and $R_5$ and $R_7$ may be bonded to $R_5$ or $R_7$ to form a cycloalkene ring when $R_5$ or $R_7$ represents an alkyl group. n5 represents an integer of 1 to 4. n6 represents an integer of 1 to 4.

In Formula (6a), when a portion represented by IND is a cation portion, $X_4$ represents a counter anion, p represents a number required to neutralize a charge, and when a portion represented by IND in the formula is an anion portion, $X_4$ represents a counter cation, p represents a number required to neutralize the charge, and when the charge of a portion represented by IND in the formula is neutralized in the molecule, p represents 0.

Examples of the counter cation include alkali metal ions (such as $Li^+$, $Na^+$, $K^+$, $Cs^+$), alkaline earth metal ions (such as $Mg^{2+}$, $Ca^{2+}$, $Ba^{2+}$, $Sr^{2+}$), transition metal ions (such as $Ag^+$, $Fe^{2+}$, $Co^{2+}$, $Ni^{2+}$, $Cu^{2+}$, $Zn^{2+}$), other metal ions (such as $Al^{3+}$), an ammonium ion, a triethylammonium ion, a tributylammonium ion, a pyridinium ion, a tetrabutylammonium ion, a guanidinium ion, a tetramethylguanidinium ion, and a diazabicycloundecenium ion.

Examples of the counter anion include halogen ions ($Cl^-$, $Br^-$, $I^-$), a p-toluenesulfonate ion, an ethyl sulfate ion, $SO_4^{2-}$, $SbF_6^-$, $PF_6^-$, $BF_4^-$, $B(C_6F_5)_4^-$, $ClO_4^-$, tris(halogenoalkylsulfonyl)methide anions (e.g., $(CF_3SO_2)_3C^-$), di(halogenoalkylsulfonyl)imide anions (e.g., $(CF_3SO_2)_2N^-$), and a tetracyanoborate anion.

Z represents a group of the above Formula (Z) or a substituent, and at least one of Z represents the group of Formula (Z). In Formula (Z), Ar, ring A, $R_r$ and a thick line are synonymous with Ar, ring A, Rr and a thick line of Formula (1a). An asterisk (*) represents a binding site with Ar in a luminescent residue of Formula (1a). In Formula (7a), when $R^5$ is an electron withdrawing group, there is no particular limitation on the electron withdrawing group, but a cyano group is preferable.

[Structure Represented by Formula (2b)]

It is preferable that the compound having a structure represented by the above Formula (1a) is a squarylium compound having a structure represented by the following Formula (2b).

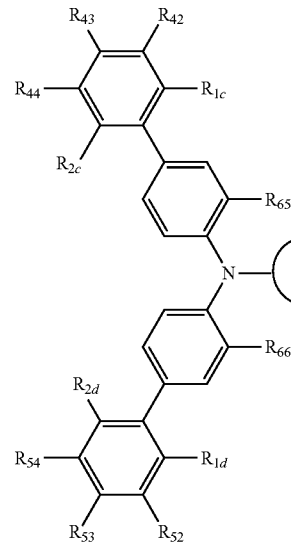
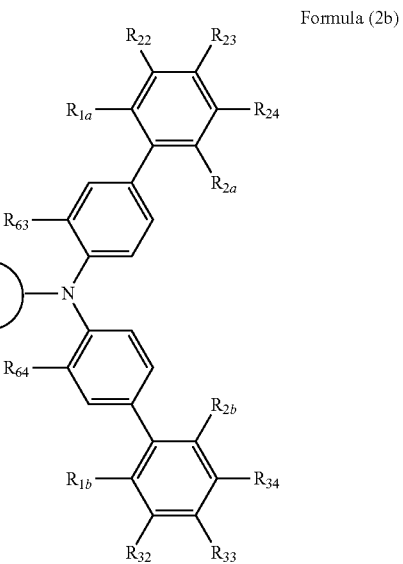

Formula (2b)

In Formula (2b), $R_{1a}$ to $R_{1d}$, $R_{2a}$ to $R_{2d}$, $R_{22}$ to $R_{24}$, $R_{22}$ to $R_{34}$, $R_{42}$ to $R_{44}$, $R_{52}$ to $R_{54}$, and $R_{63}$ to $R_{66}$ each independently represent a hydrogen atom, an alkyl group, an alkoxy group, a phenoxy group, an amino group, an aryl group, or a heteroaryl group. At least one of the combinations of $R_{1a}$ and $R_{2a}$, $R_{1b}$ and $R_{2b}$, $R_{1c}$ and $R_{2c}$, and $R_{1d}$ and $R_{2d}$ does not both represent a hydrogen atom. $R_{1a}$ and $R_{22}$, $R_{2a}$ and $R_{24}$, $R_{1b}$ and $R_{32}$, $R_{2b}$ and $R_{34}$, $R_{1c}$ and $R_{42}$, $R_{2c}$ and $R_{44}$, $R_{1d}$ and $R_{52}$, and $R_{2d}$ and $R_{54}$ may be bonded to form a ring structure. Ring H and ring I each independently represent an aryl group which may be substituted with a hydroxy group, an alkoxy group, an NHCORa group (Ra represents a hydrocarbon group), an $NHSO_2Rb$ group (Rb represents a hydrocarbon group), or an NHPO(ORf)(ORg) group (Rf and Rg each independently represent a hydrocarbon group).

In the squarylium compound having a structure represented by Formula (2b), it is preferable that $R_{1a}$ to $R_{1d}$ and $R_{2a}$ to $R_{2d}$ are the same and represent an alkyl group, an alkoxy group, a phenoxy group, an amino group, an aryl group or a heteroaryl group. Further, in the squarylium compound having a structure represented by Formula (2b), ring H and ring I are the same and represent an aryl group having a hydroxy I group, $R_{22}$ to $R_{24}$, $R_{32}$ to $R_{34}$, $R_{42}$ to $R_{44}$ and $R_{52}$ to $R_{54}$ are the same as $R_{1a}$ to $R_{1d}$ and $R_{2a}$ to $R_{2d}$ or a hydrogen atom. At least one of the combinations of $R_{1a}$ and $R_{2a}$, $R_{1b}$ and $R_{2b}$, $R_{1c}$ and $R_{2c}$, and $R_{1d}$ and $R_{2d}$ does not both represent a hydrogen atom, and $R_{22}$, $R_{24}$, $R_{32}$, $R_{34}$, $R_{42}$, $R_{44}$, $R_{52}$ and $R_{54}$ preferably represent a hydrogen atom. Further, it is preferable that rings H and ring I are the same and represent an aryl group having a hydroxyl group, $R_{1a}$ and $R_{22}$, $R_{2a}$ and $R_{24}$, $R_{1b}$ and $R_{32}$, $R_{2b}$ and $R_{34}$, $R_{1c}$ and $R_{42}$, $R_{2c}$ and $R_{44}$, $R_{1d}$ and $R_{52}$, and $R_{2d}$ and $R_{54}$ may be bonded respectively to form a 5-membered or a 6-membered ring structure with a carbon chain.

Examples of the infrared-emitting compound having the structures represented by Formulas (1a) to (8a) of the present invention will be described below, but the present invention is not limited thereto.

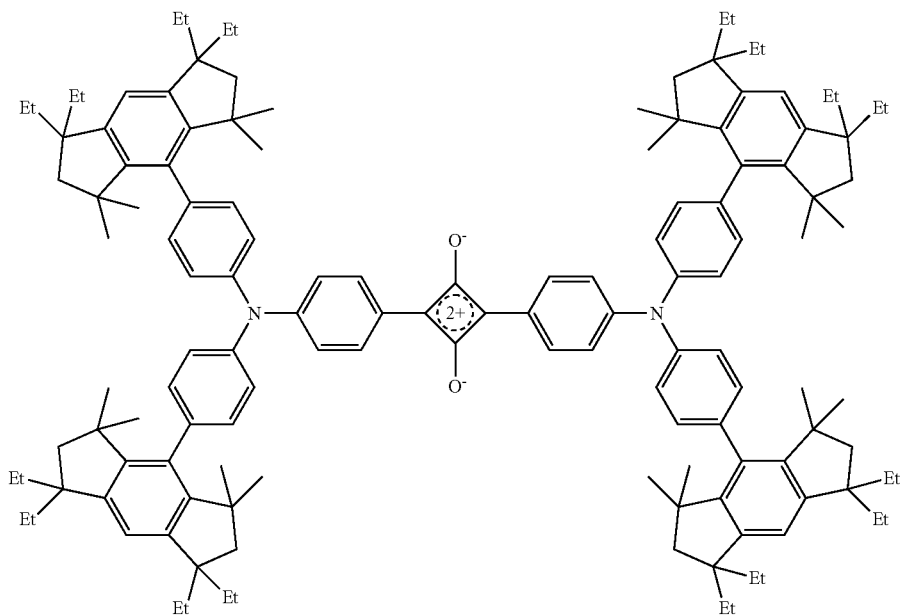
Da-1
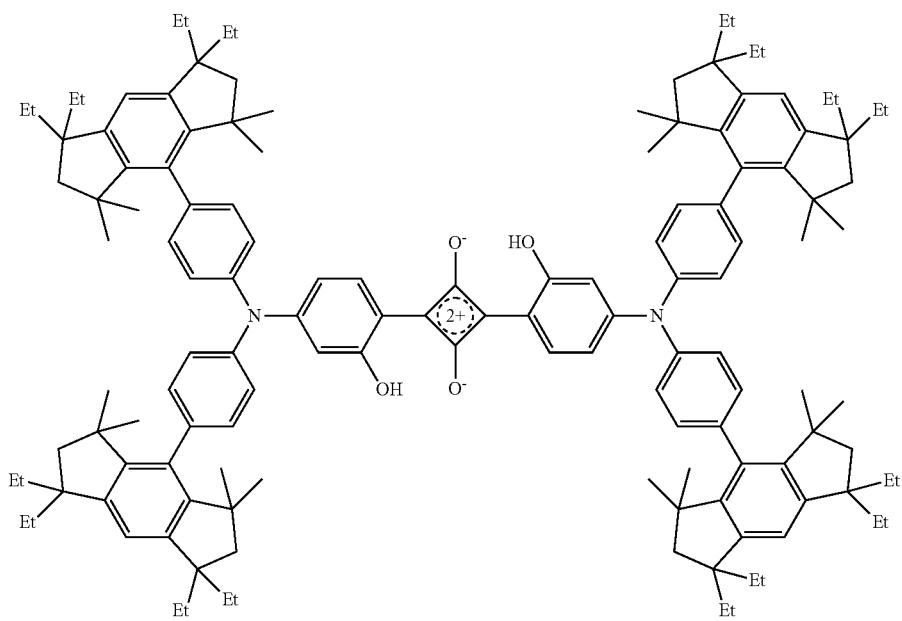
Da-2

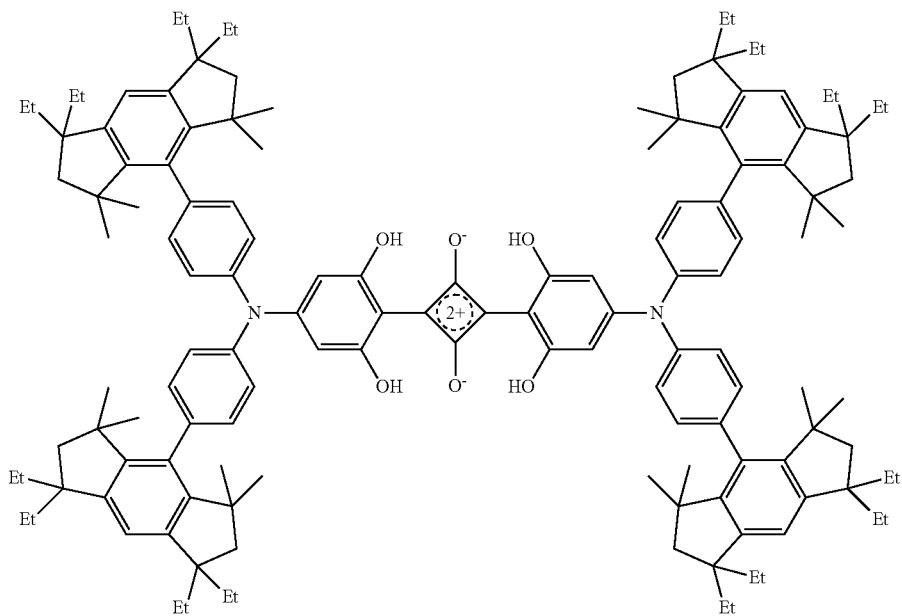
Da-3
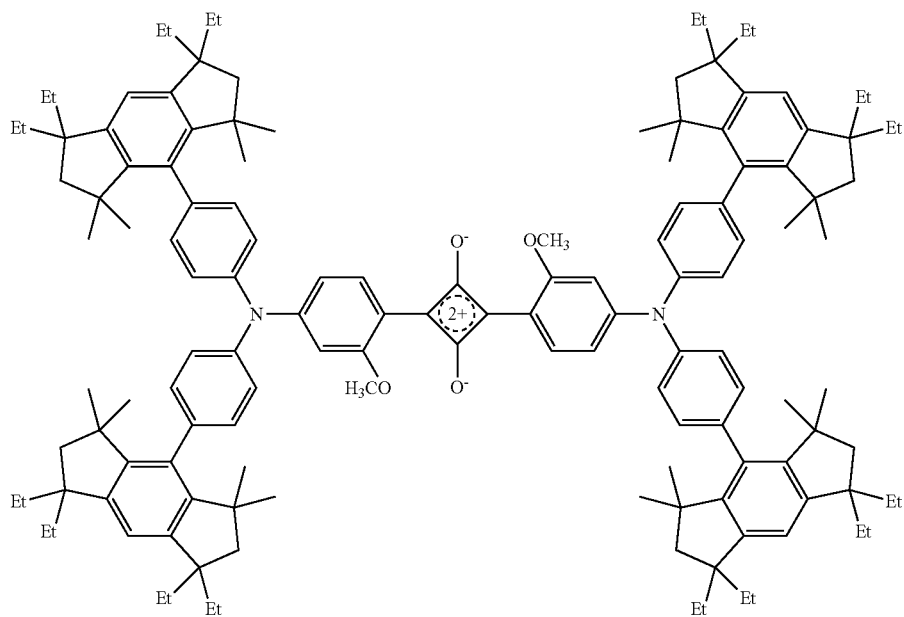
Da-4

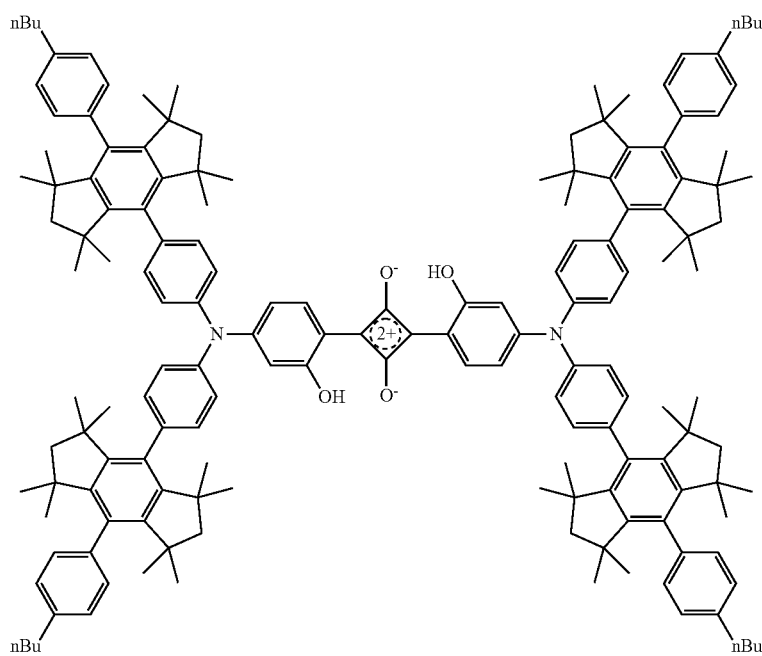
Da-5
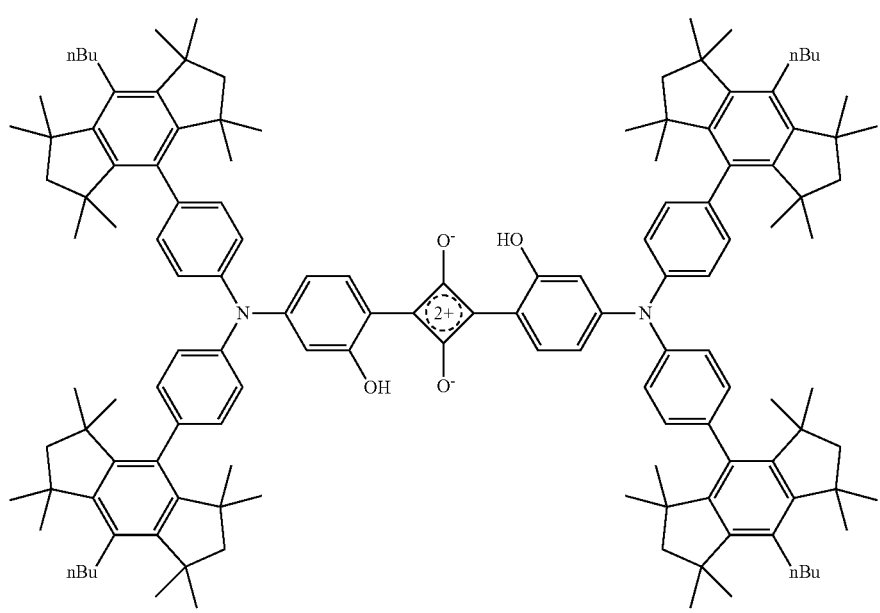
Da-6

-continued
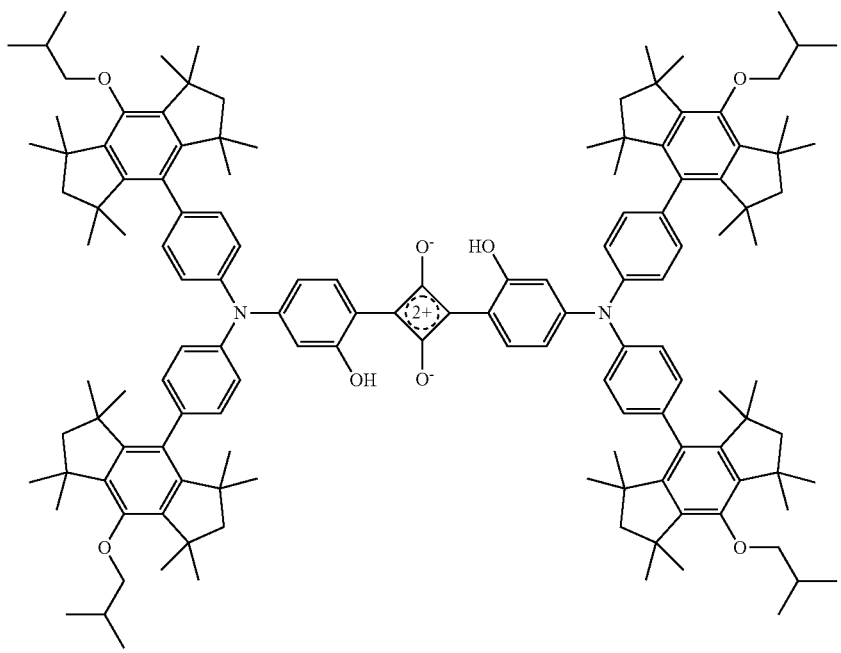
Da-7
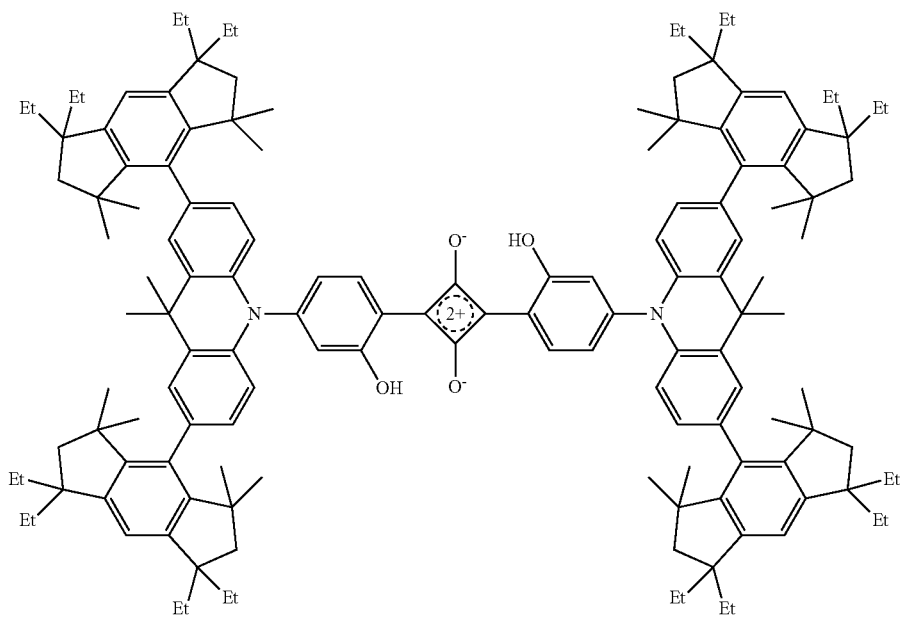
Da-8

Da-9
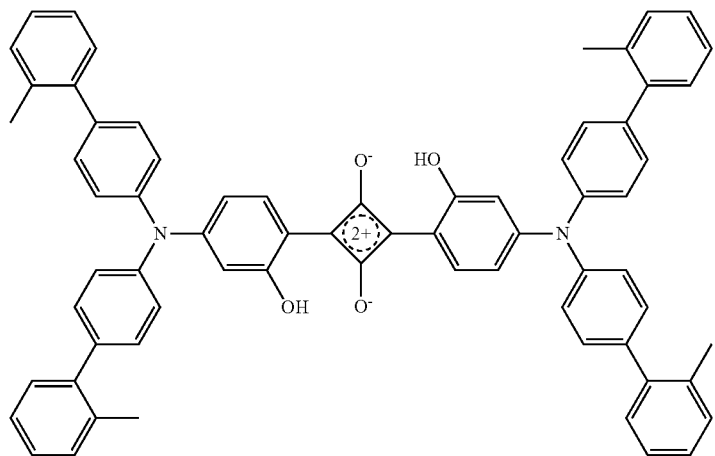
Da-10
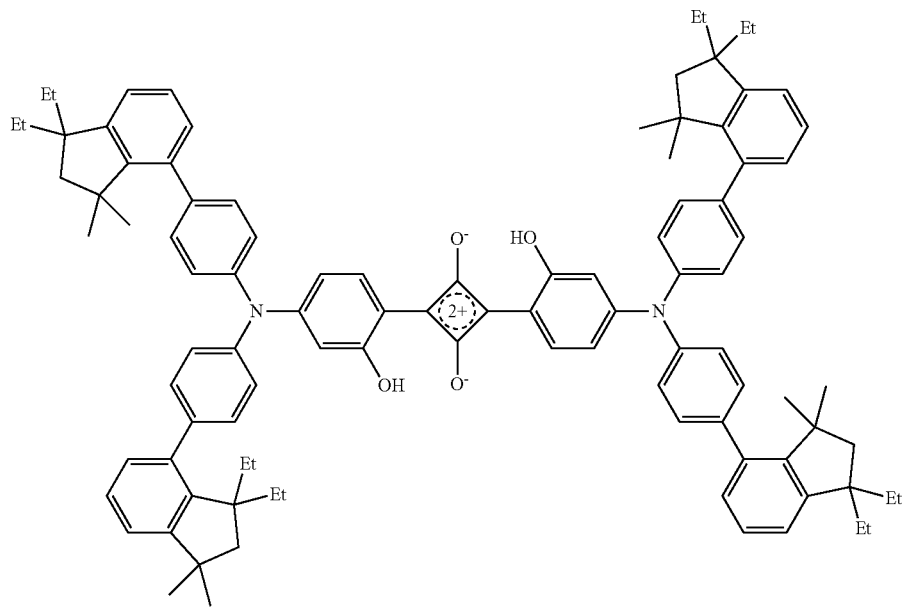
Da-11
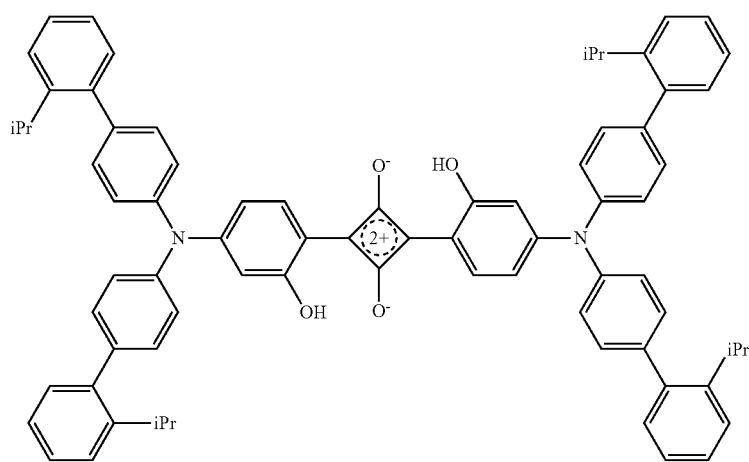

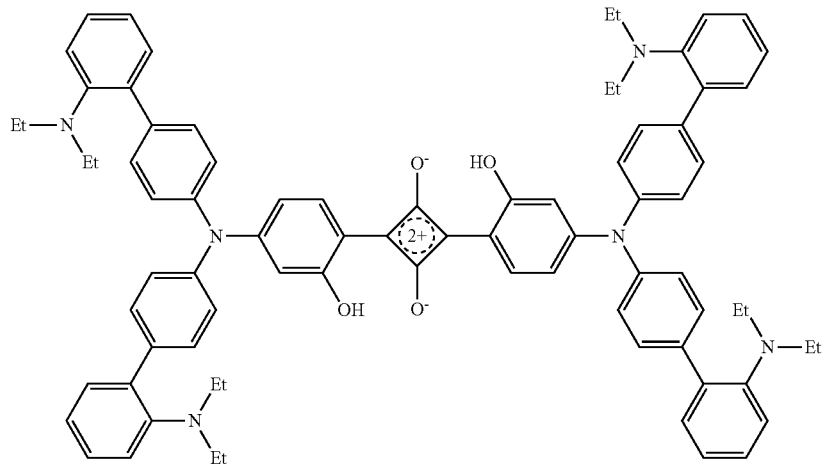
Da-12
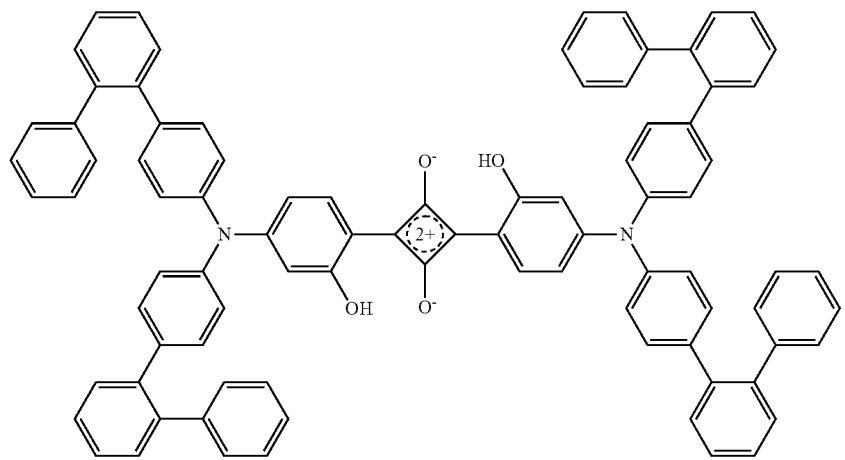
Da-13
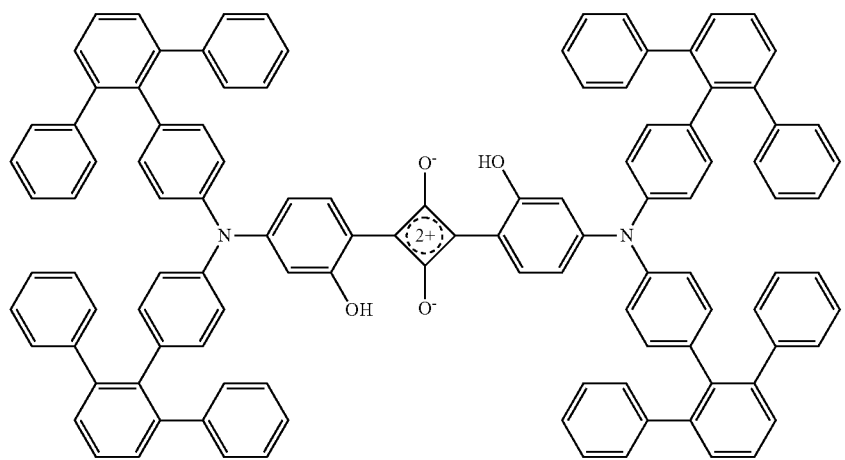
Da-14

-continued
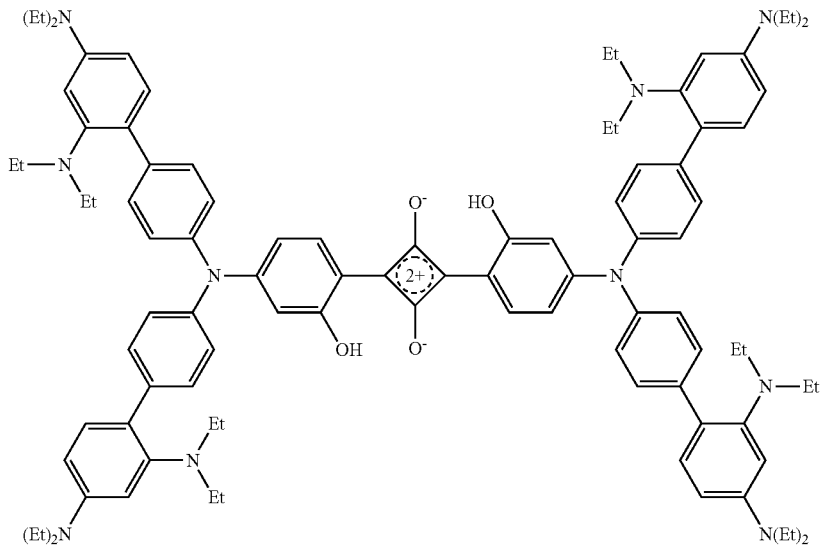
Da-15
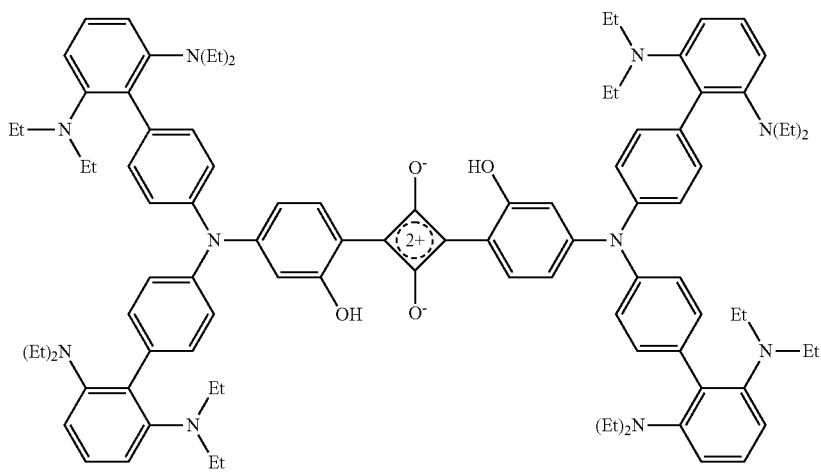
Da-16
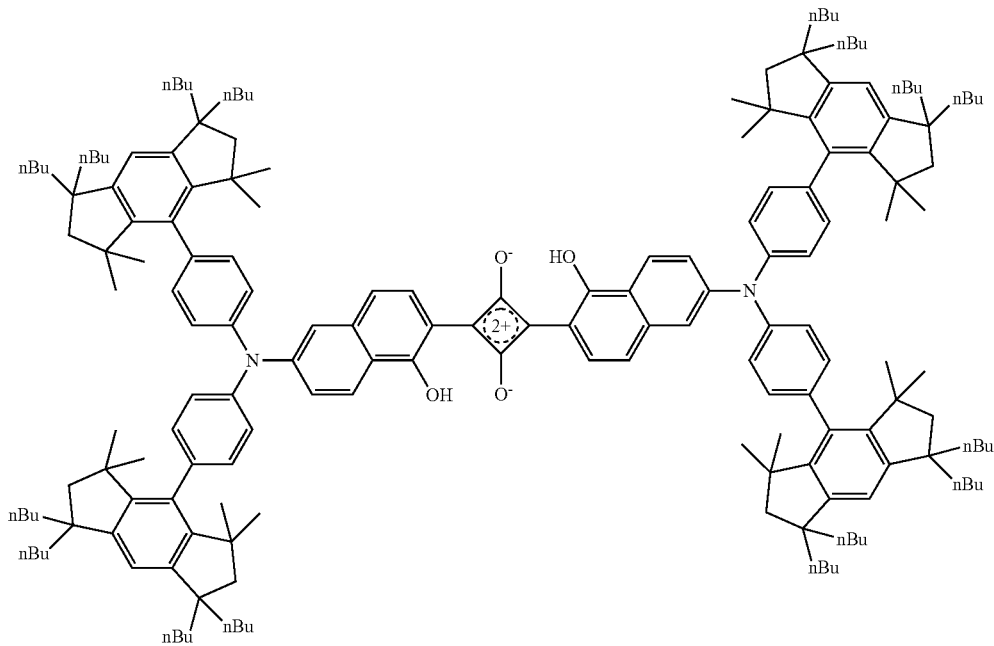
Da-17

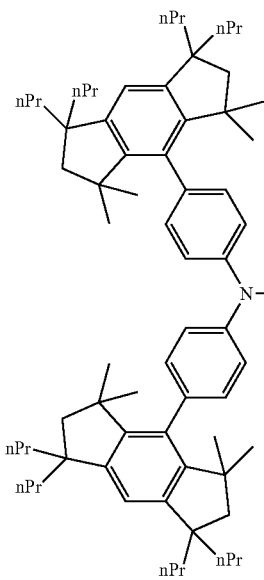
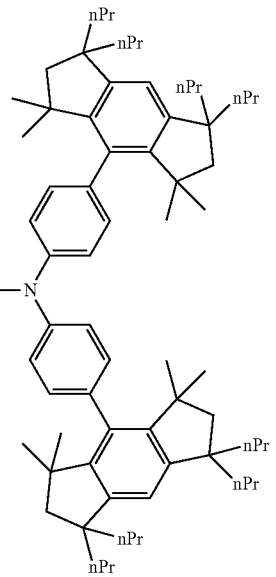
Da-18
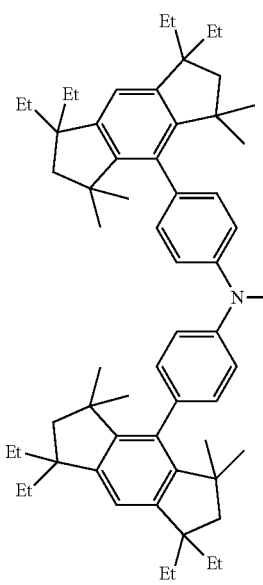
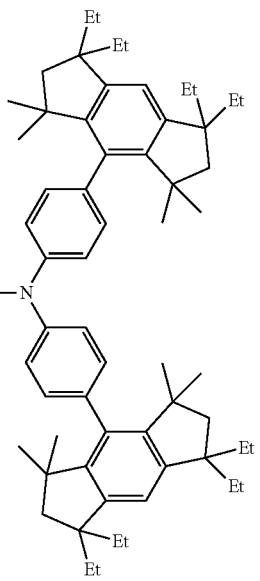
Da-19

-continued
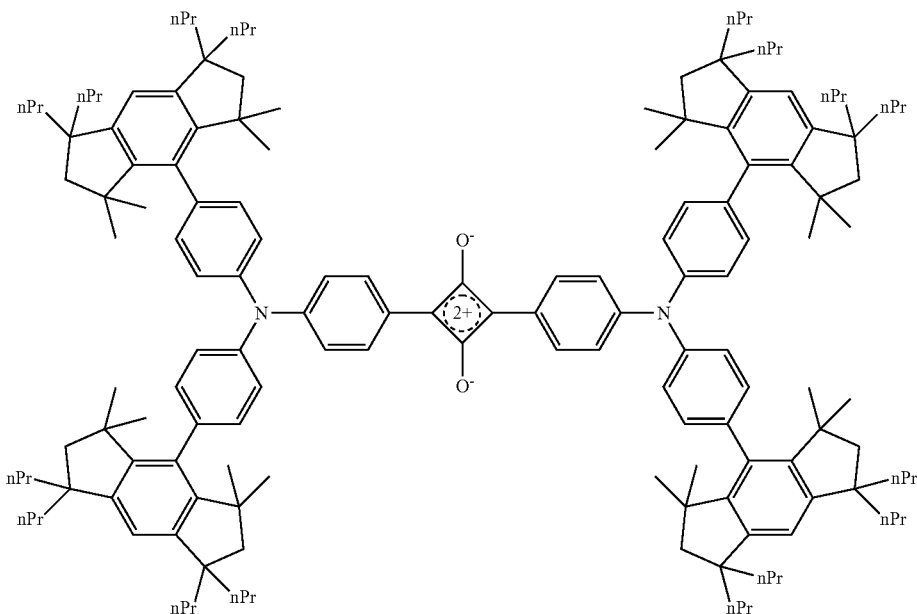
Da-20
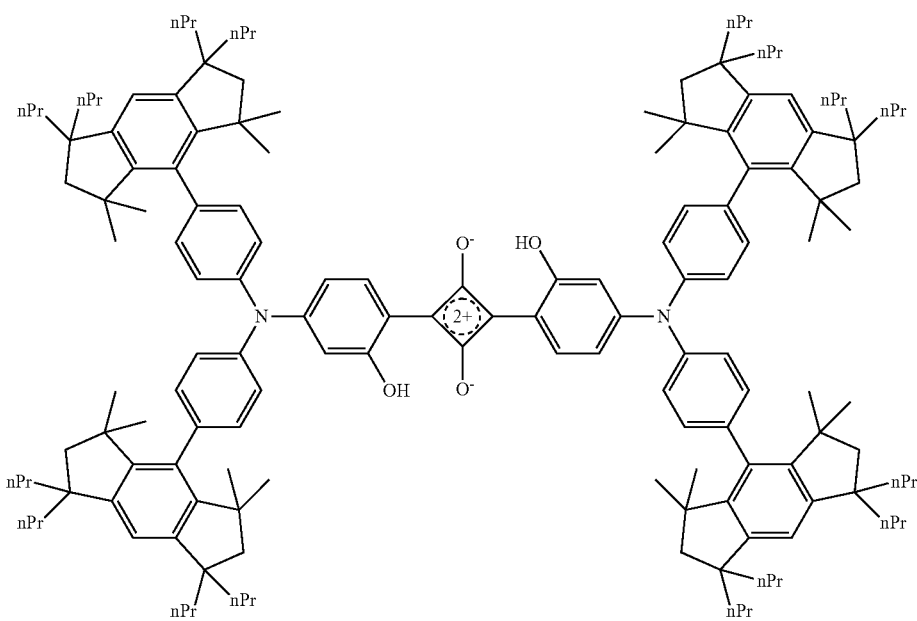
Da-21

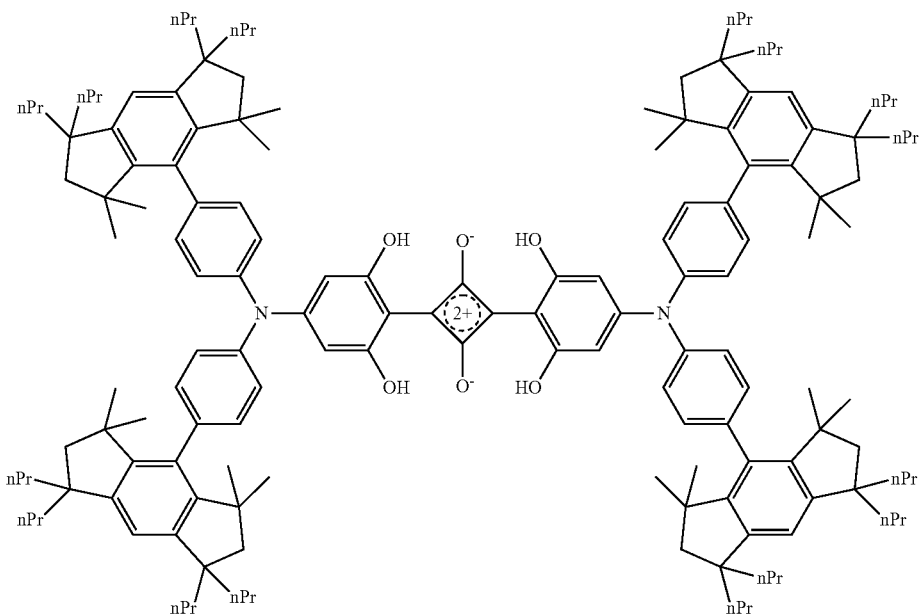
Da-22
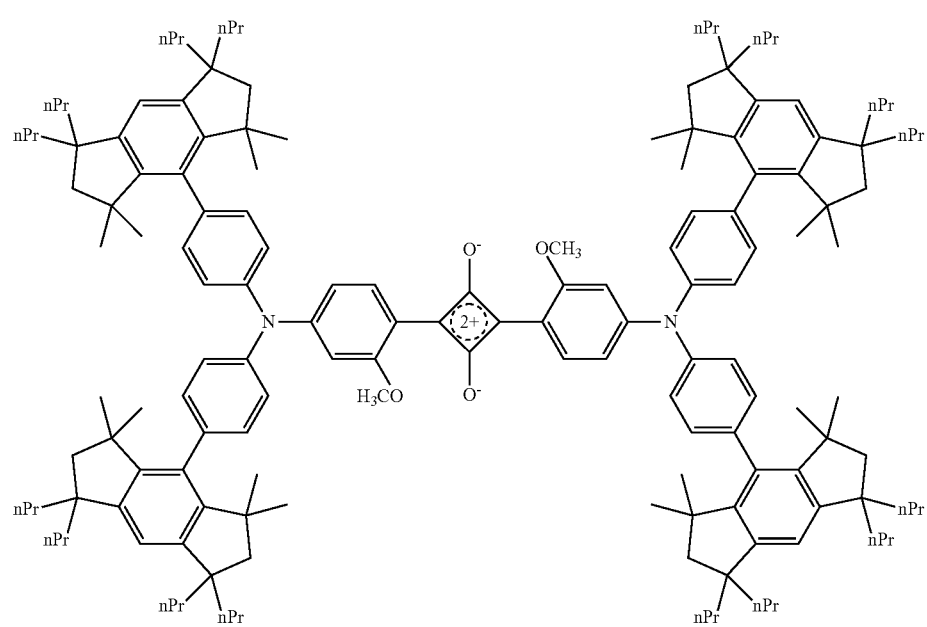
Da-23

-continued
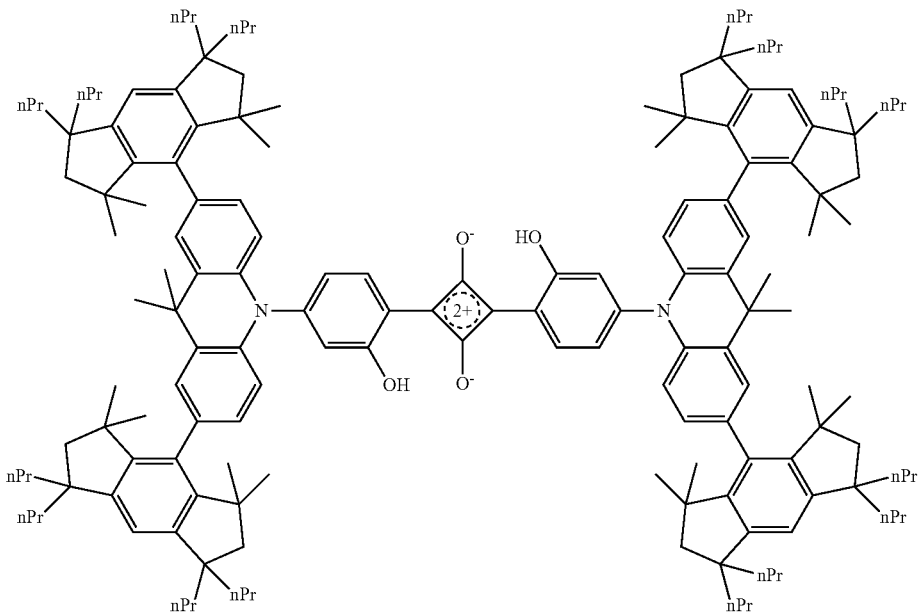
Da-24
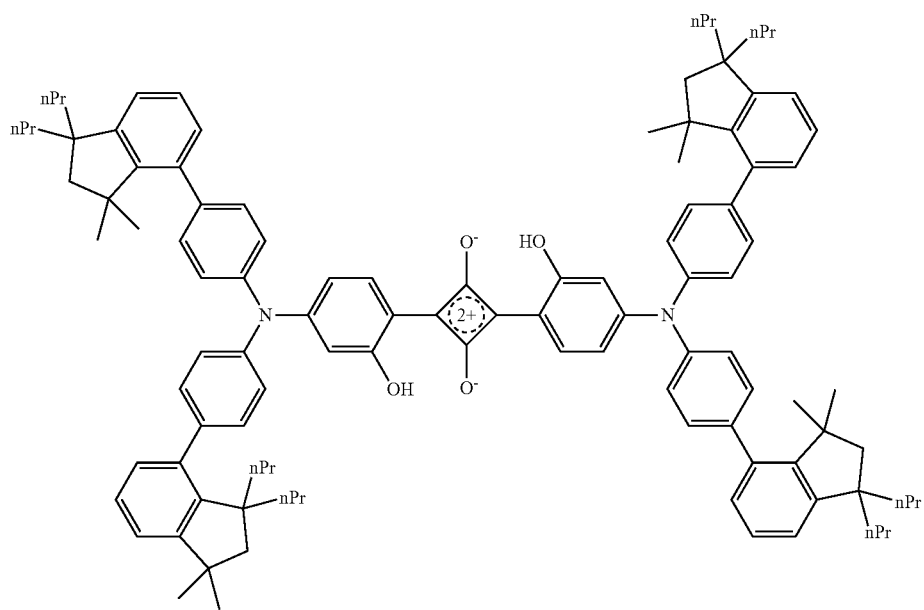
Da-25

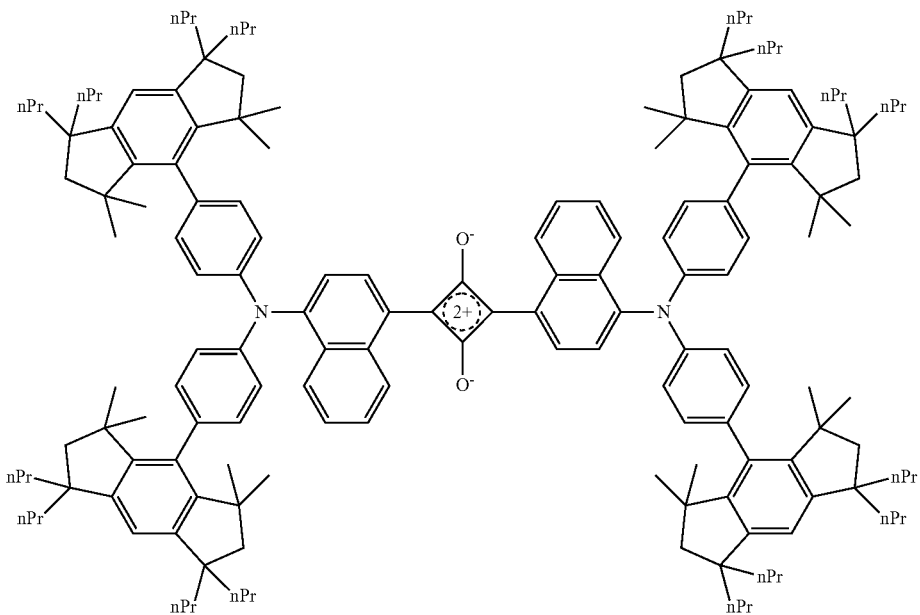
Da-26
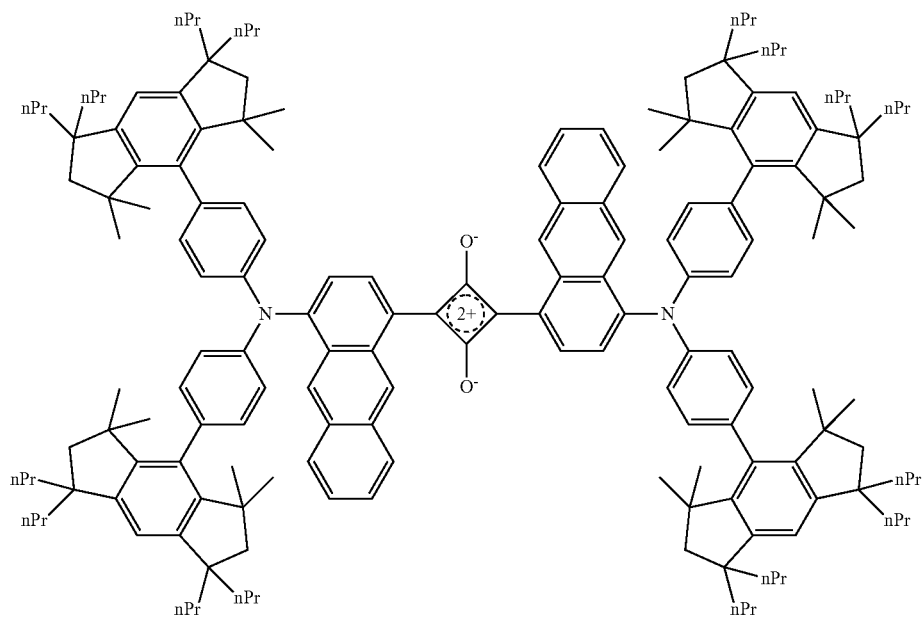
Da-27

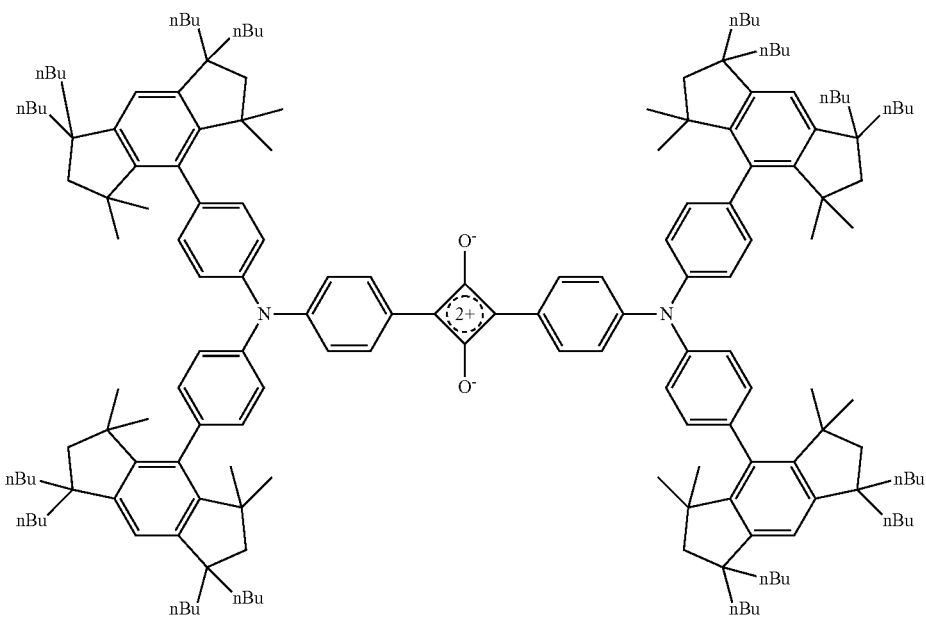
Da-28
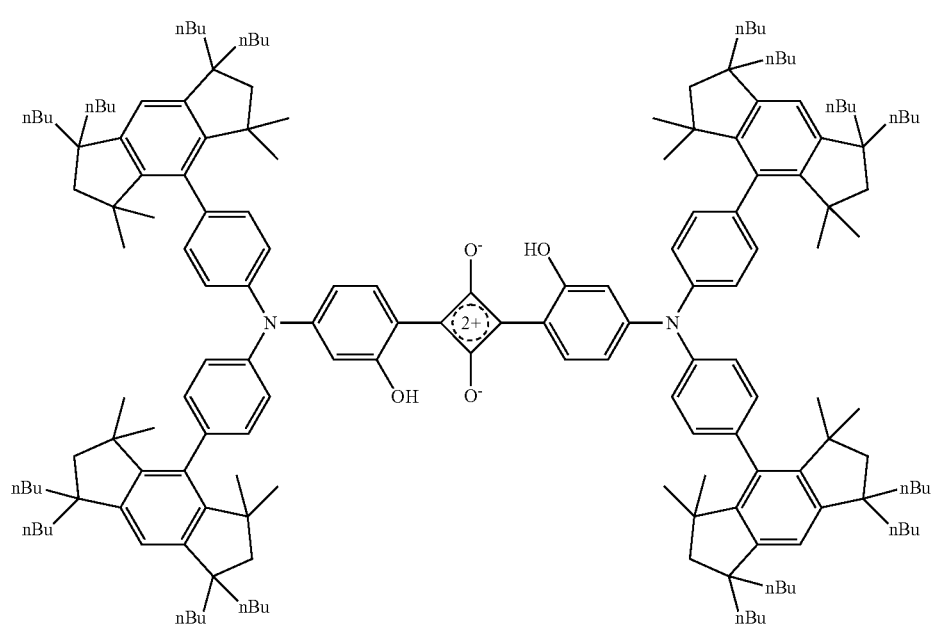
Da-29

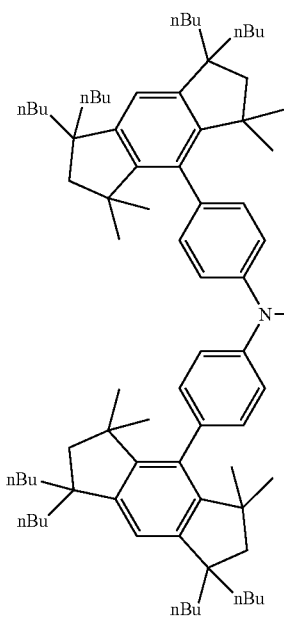
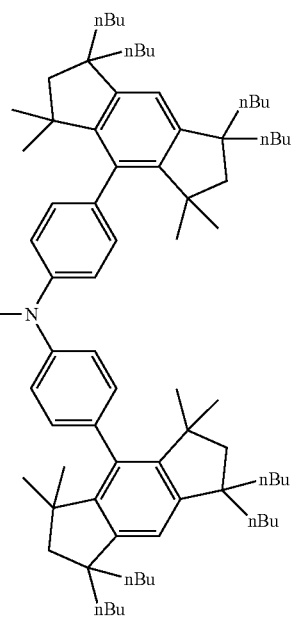
Da-30
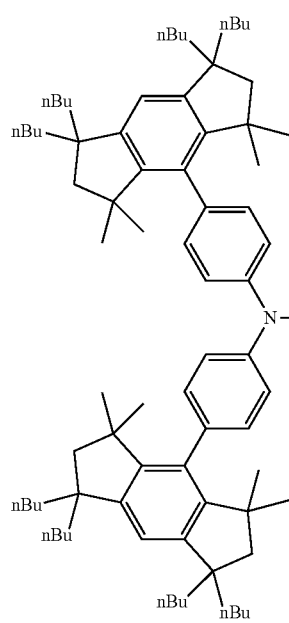
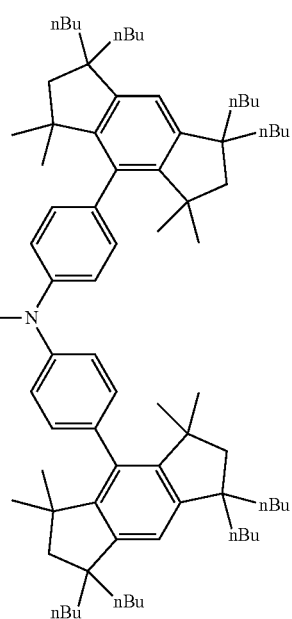
Da-31

-continued
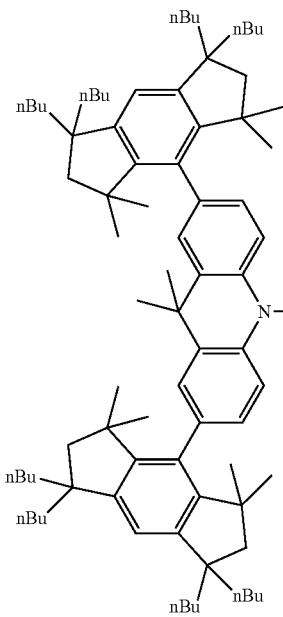
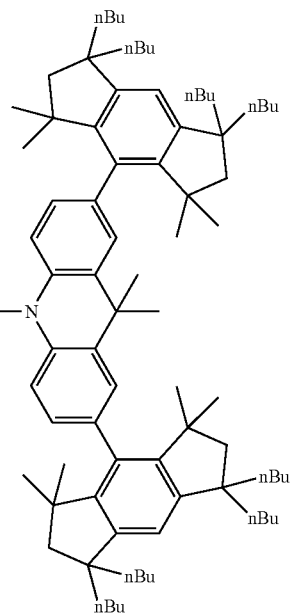
Da-32
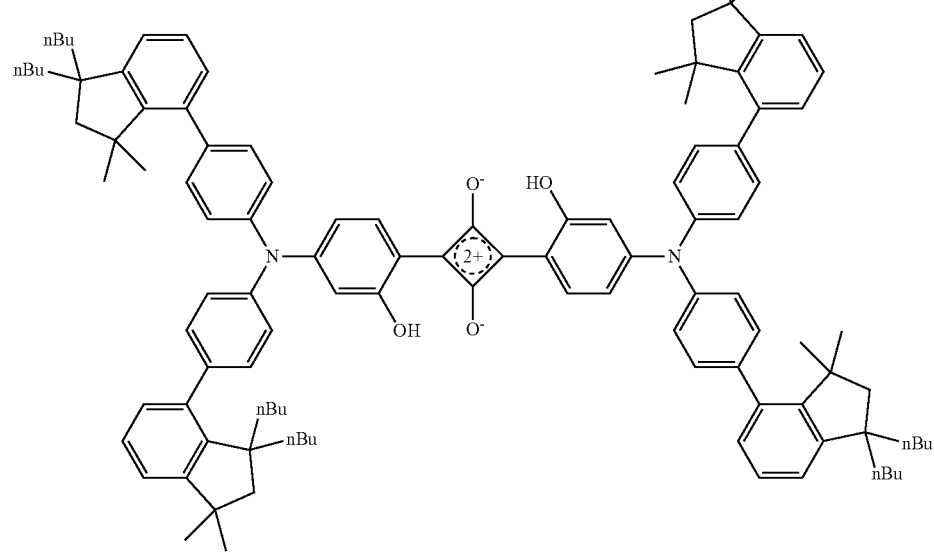
Da-33

-continued
Da-34
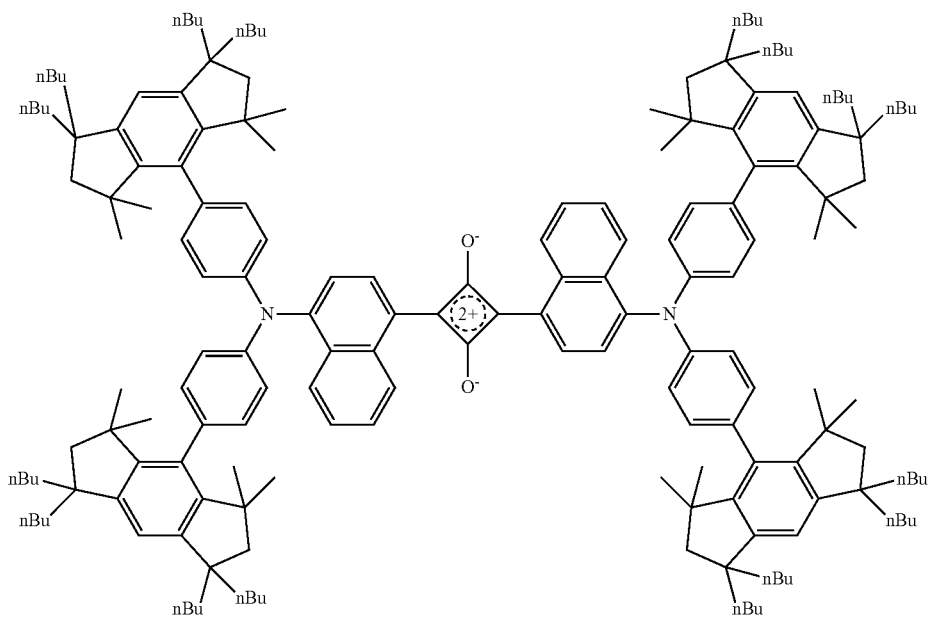
Da-35
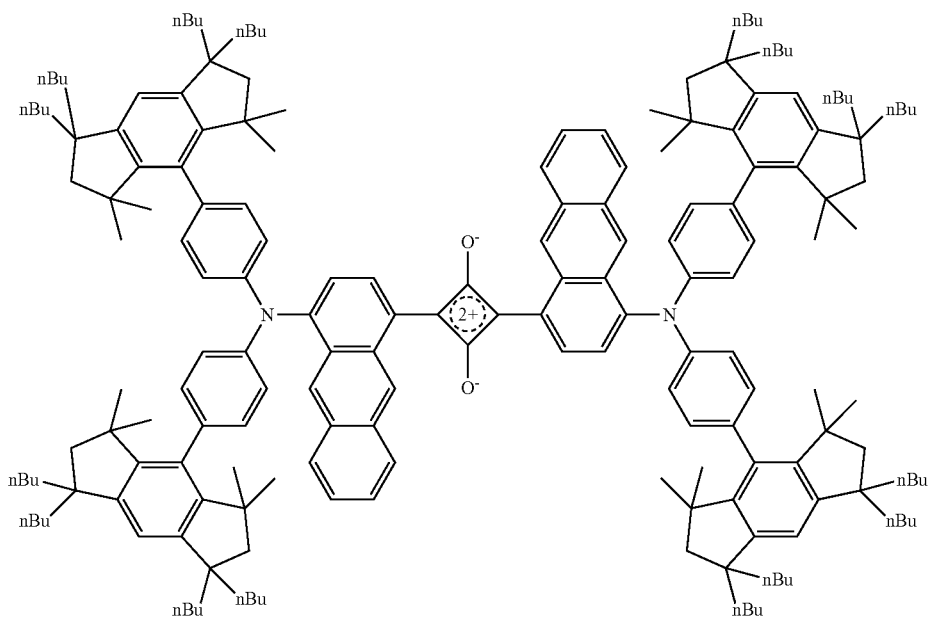
Da-36     Da-37
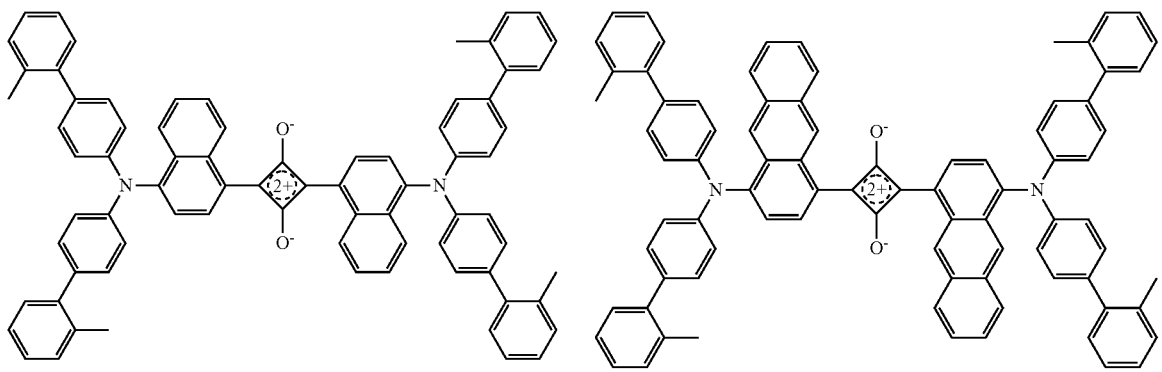

-continued
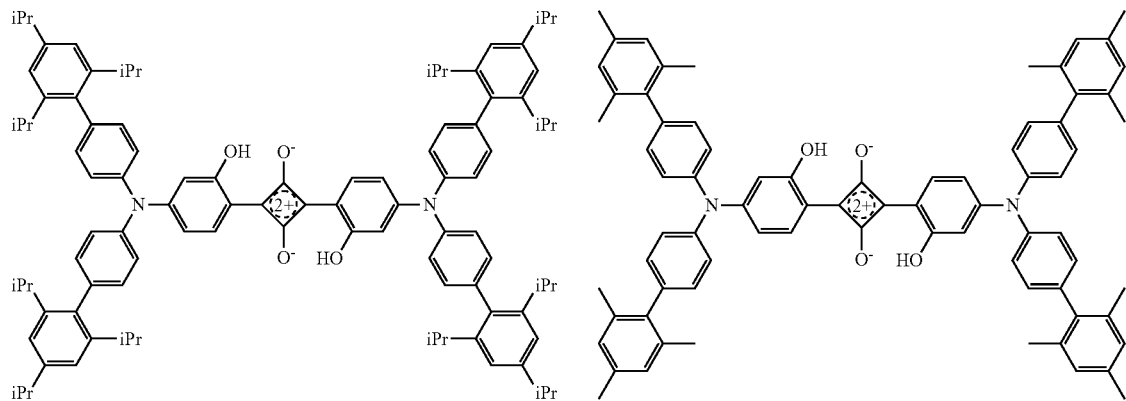
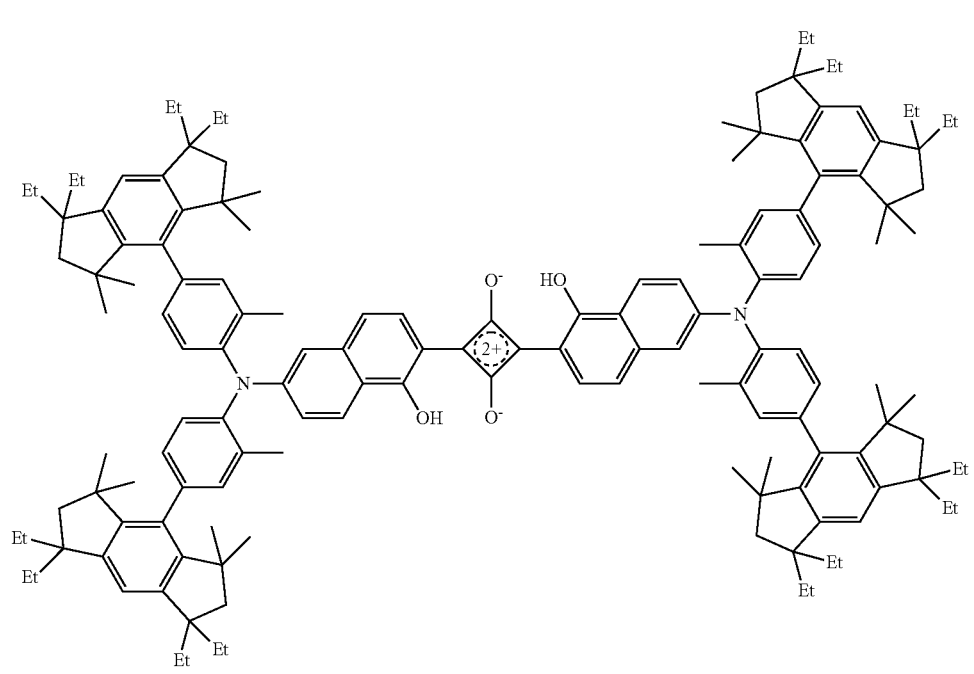

Da-41
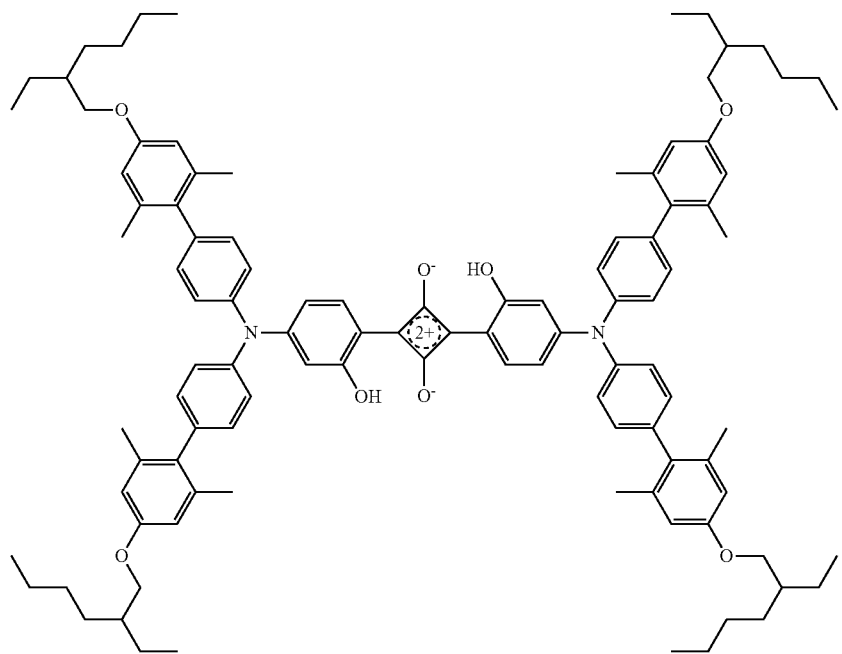
Da-42
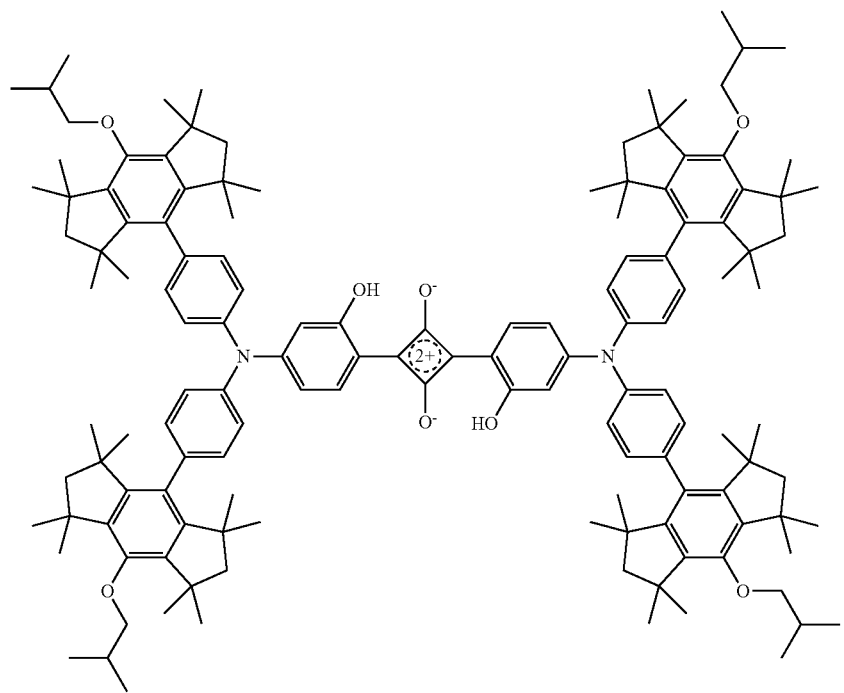

Da-43
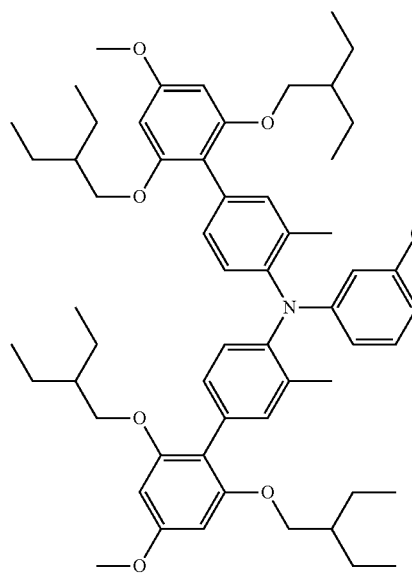
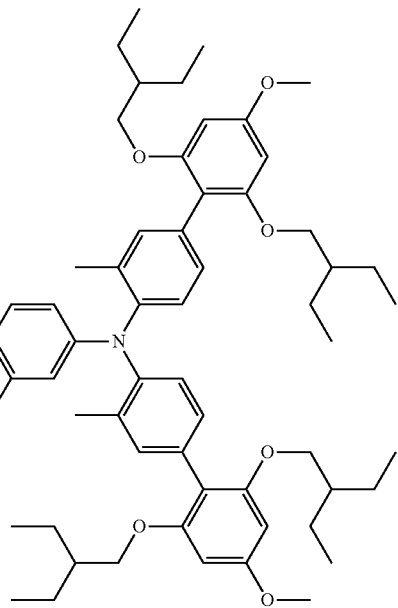
Da-44
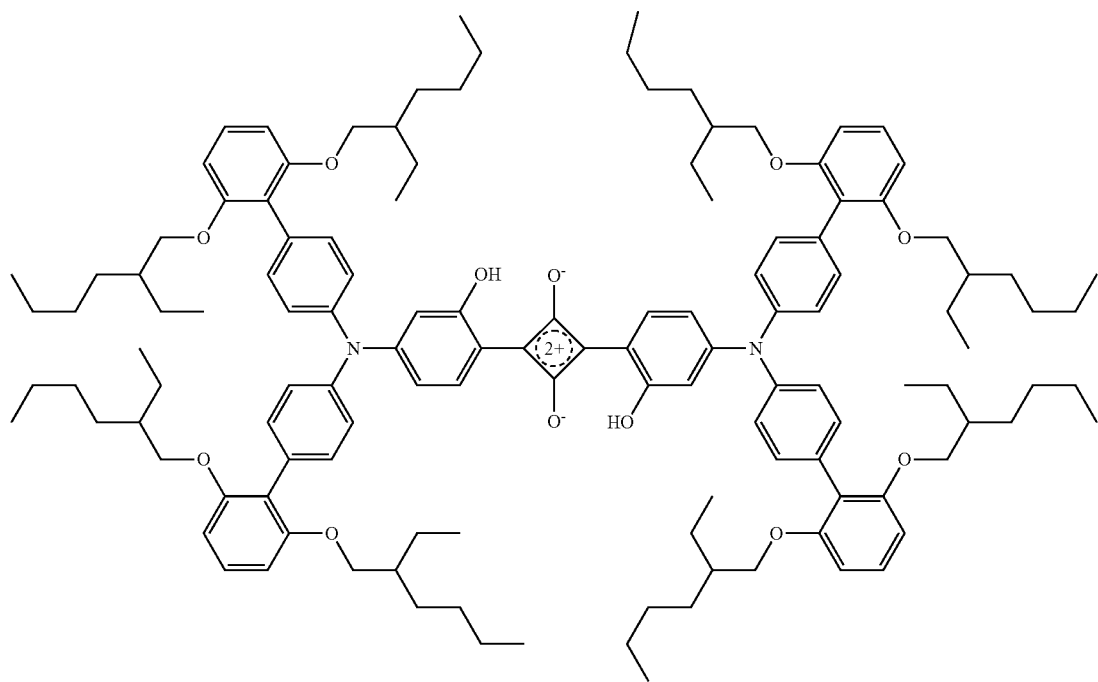

Da-45
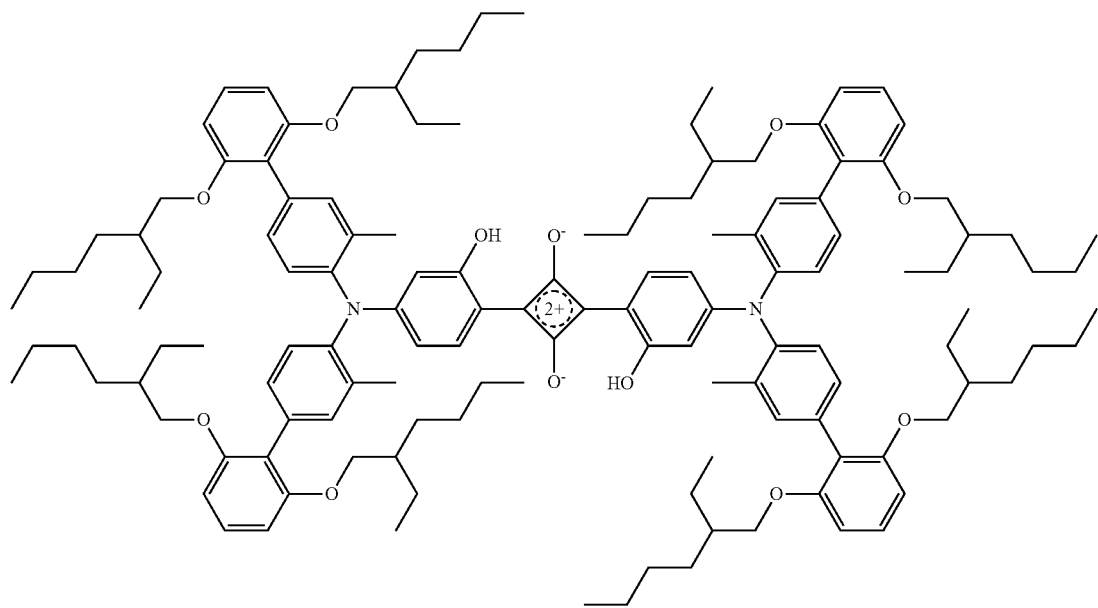
Da-46
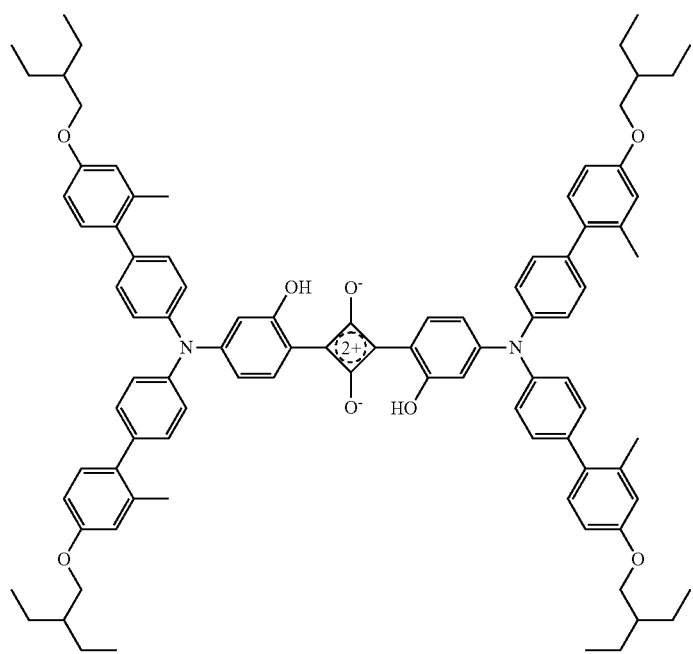

Da-47
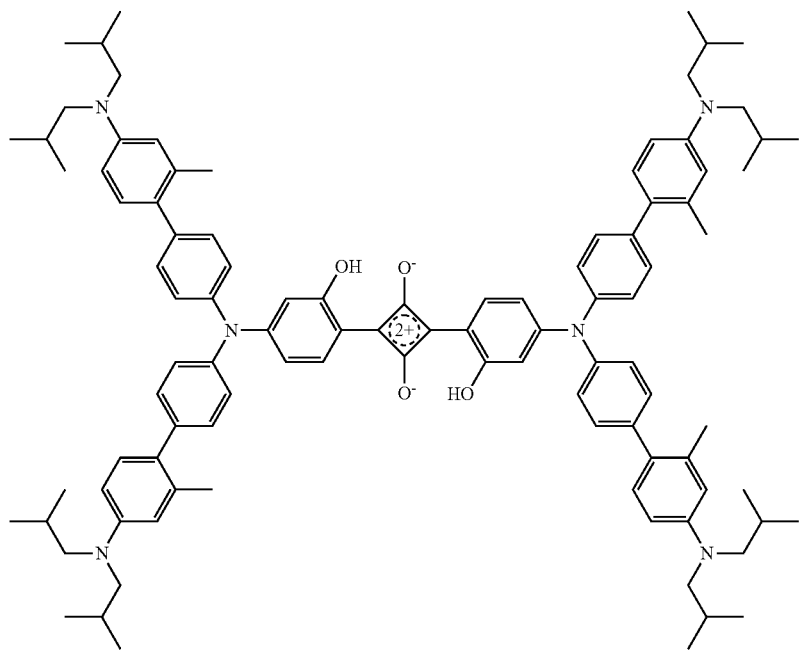
Da-48
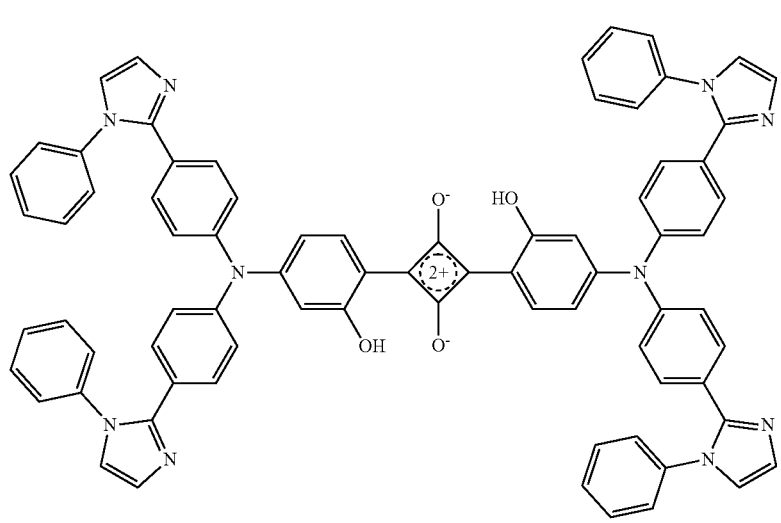
Da-49
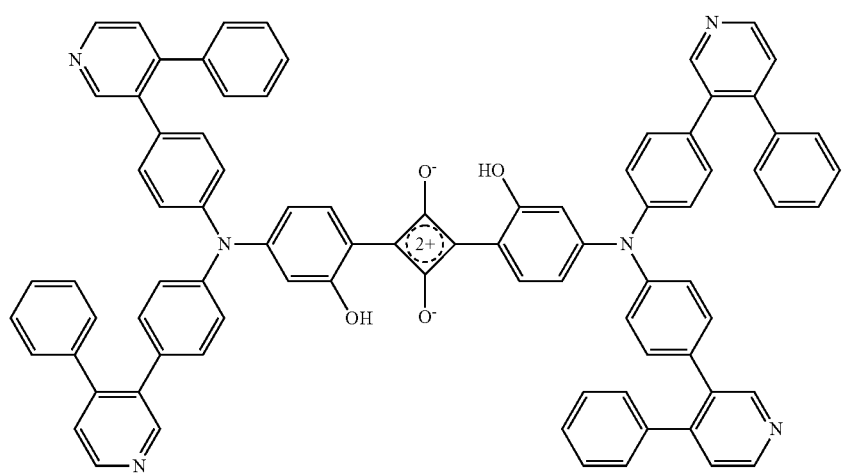

-continued
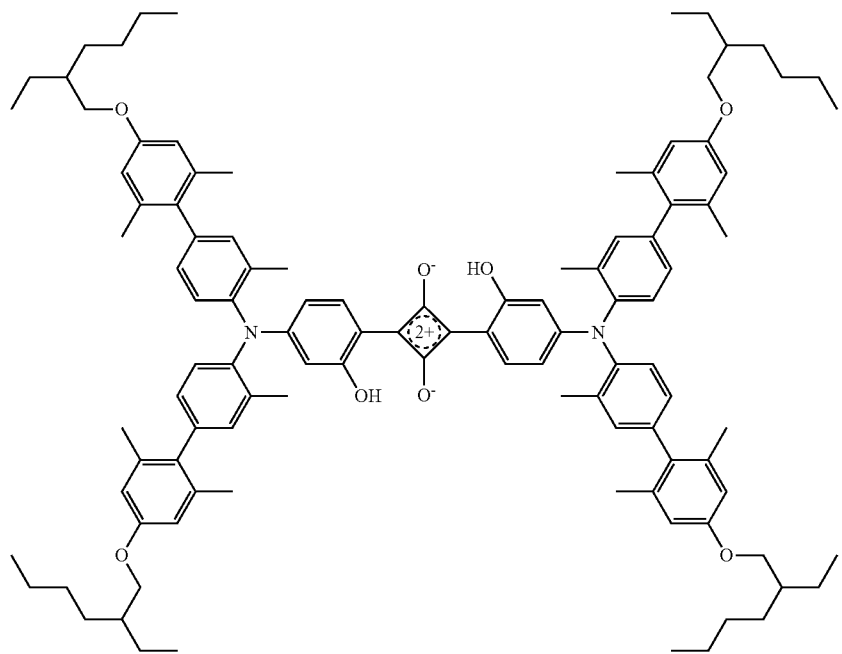
Da-50
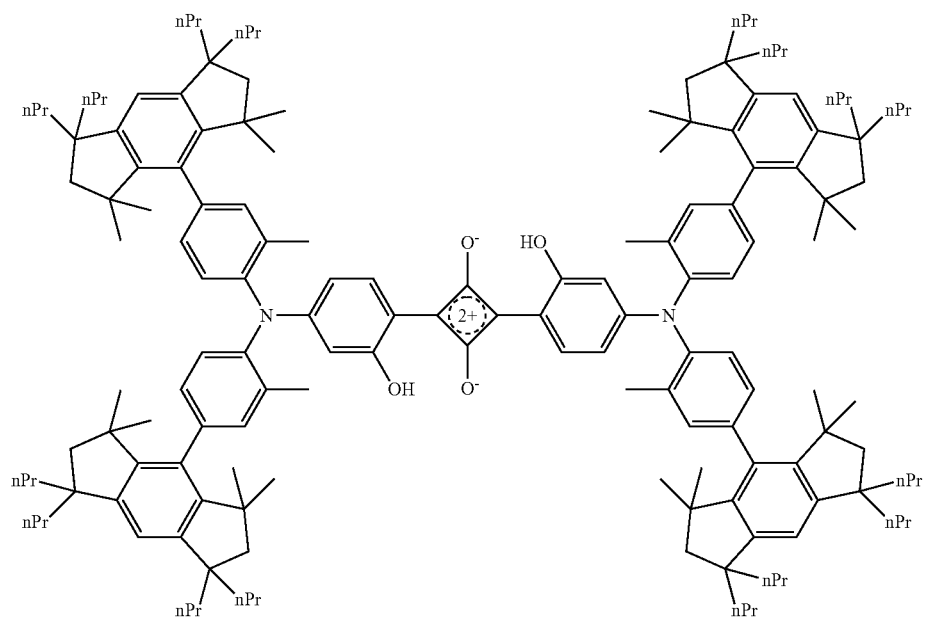
Da-51

-continued
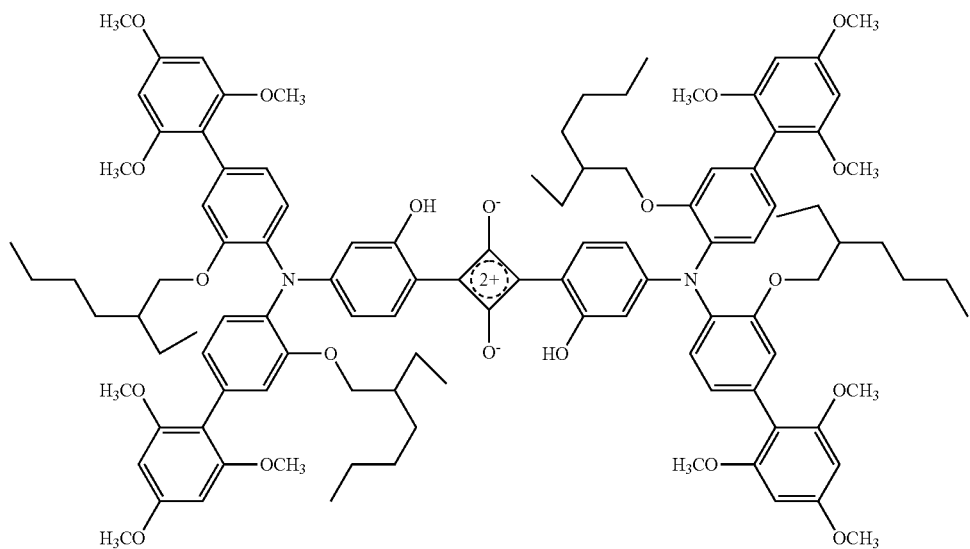
Da-52
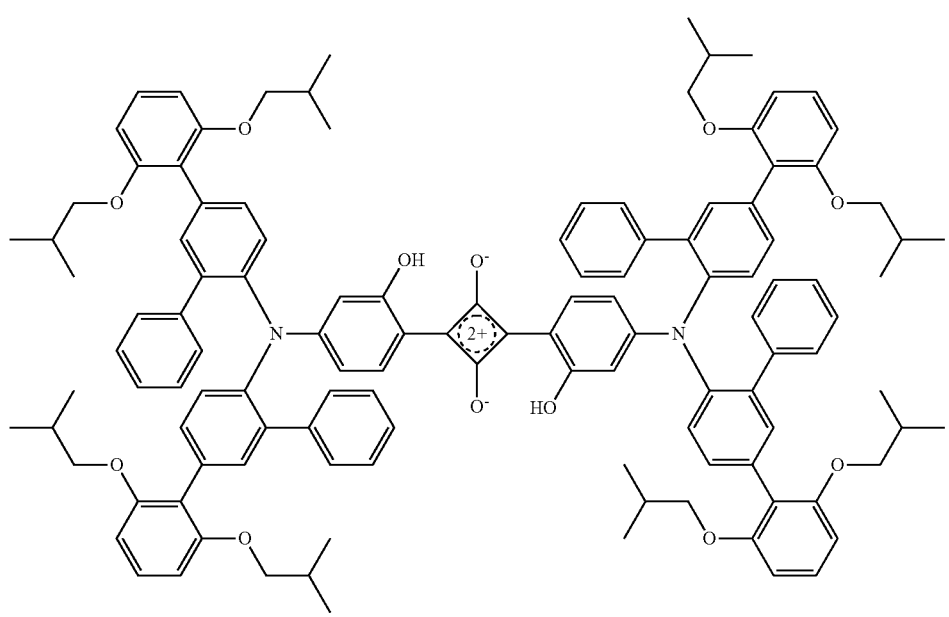
Da-53
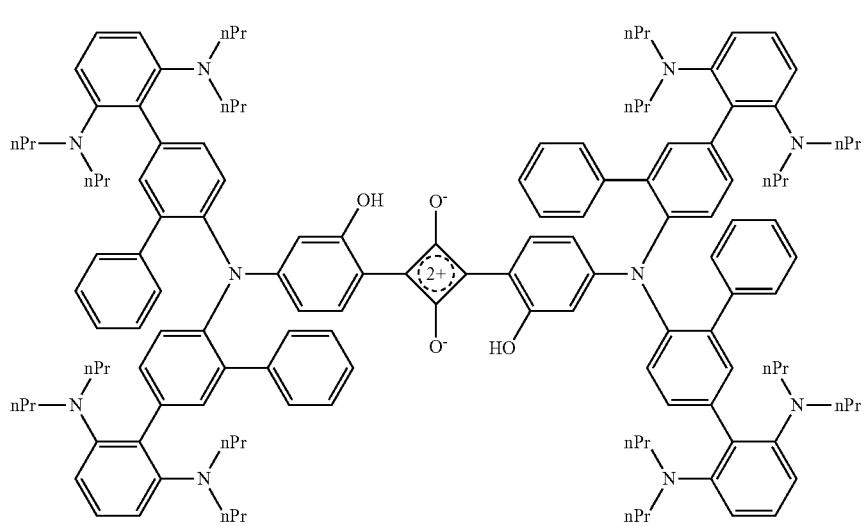
Da-54

-continued
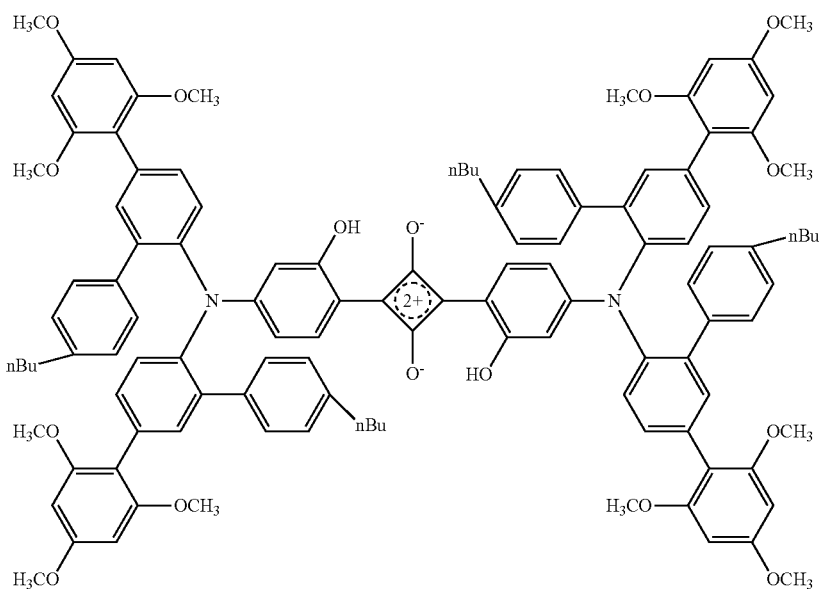
Da-55
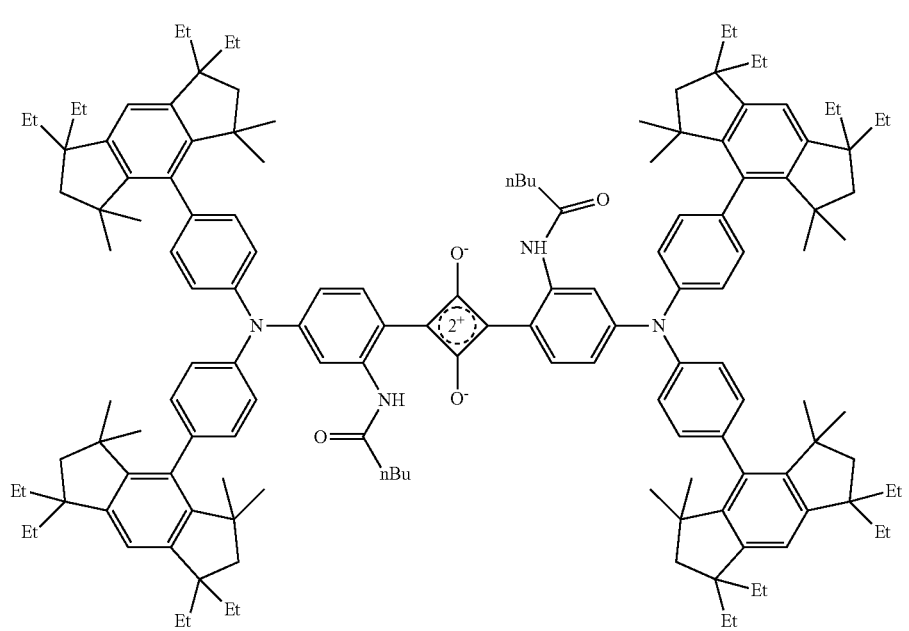
Da-56

-continued
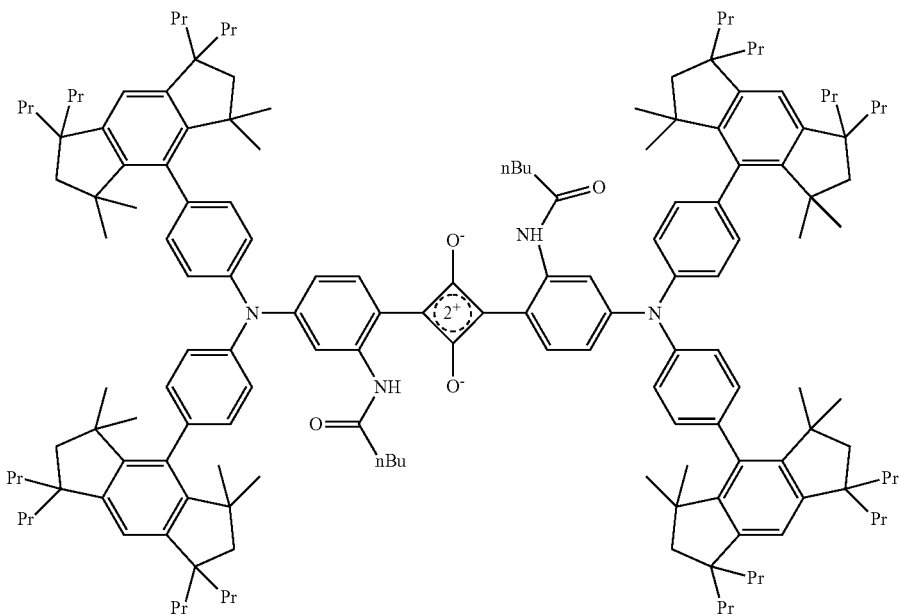
Da-57
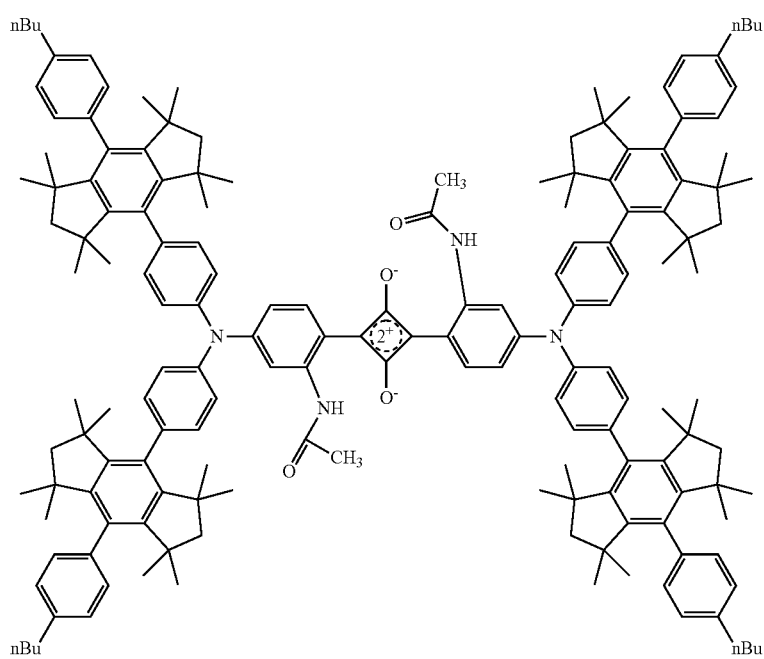
Da-58

-continued
Da-59
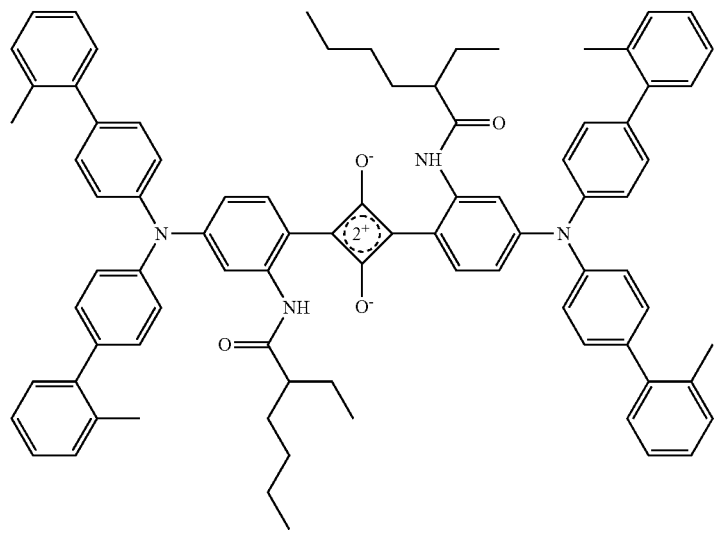
Da-60
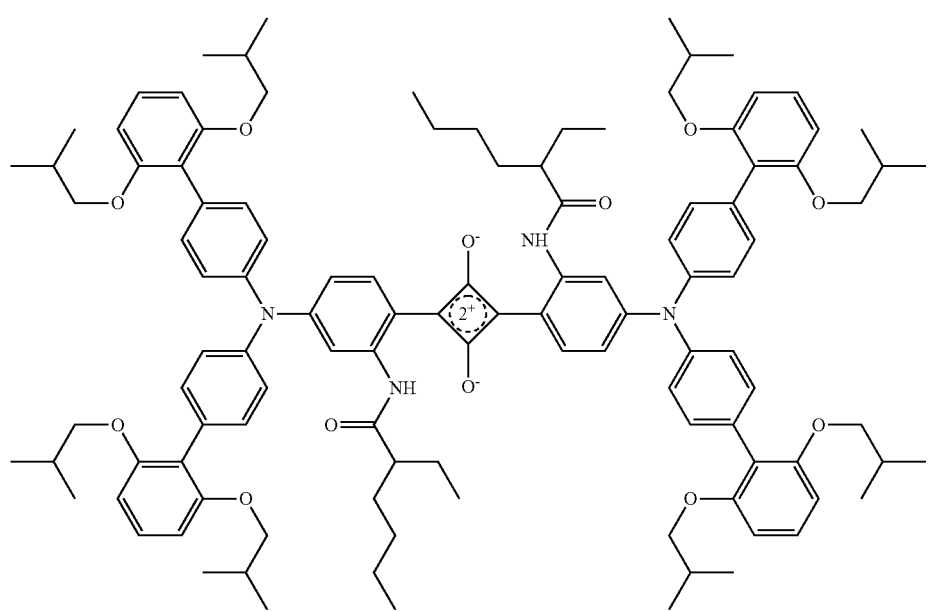

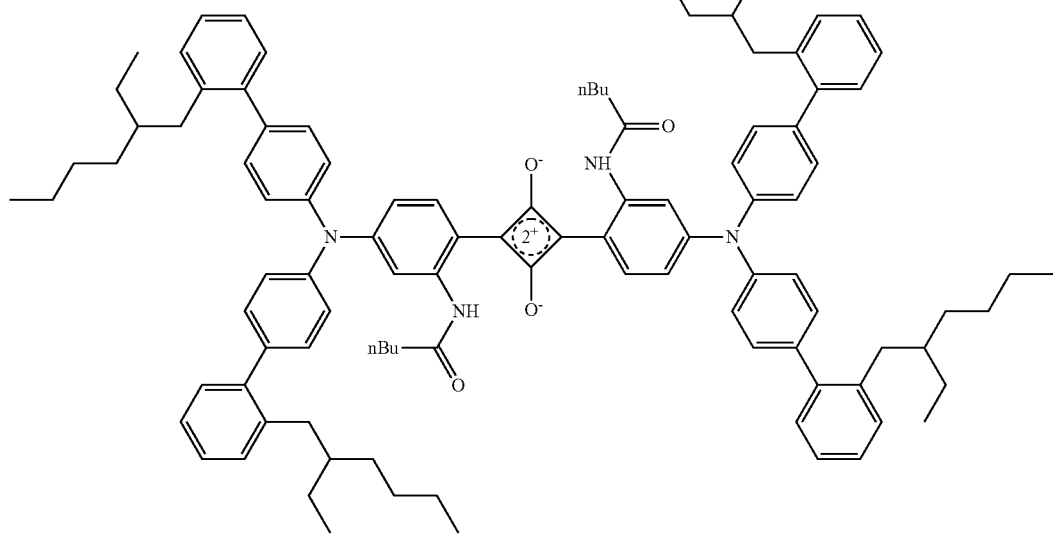
Da-61
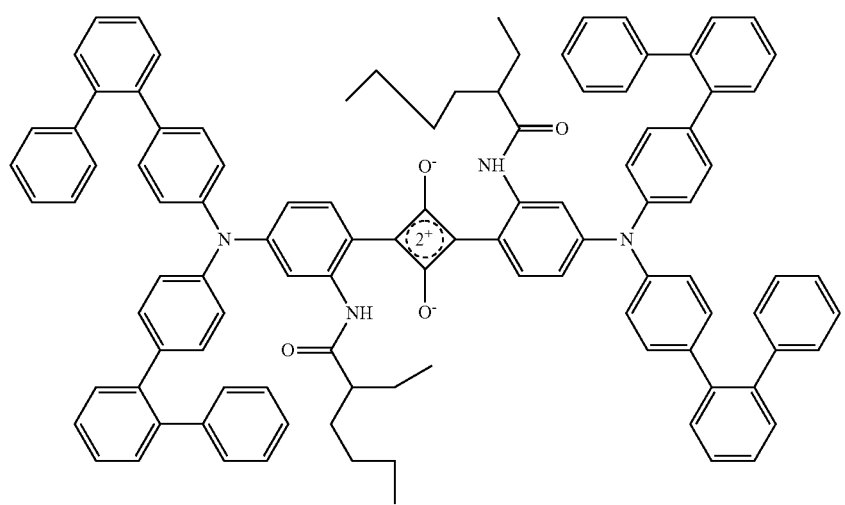
Da-62

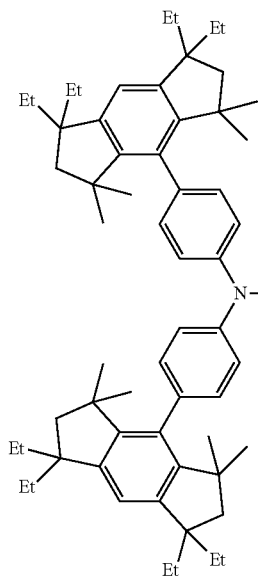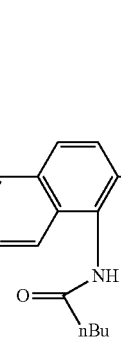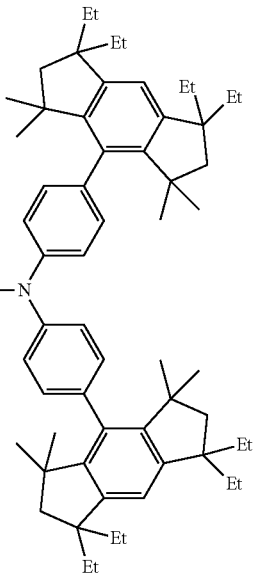
Da-63
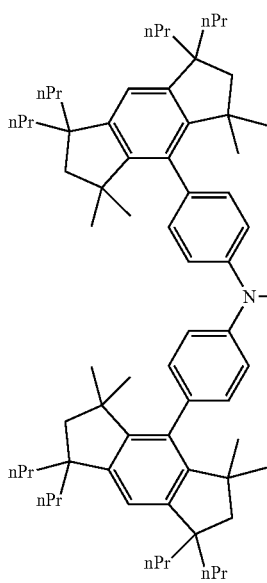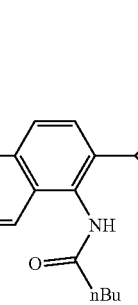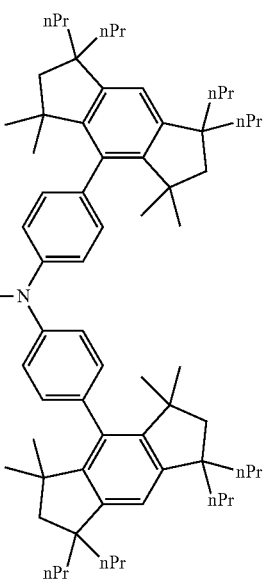
Da-64

-continued
Da-65
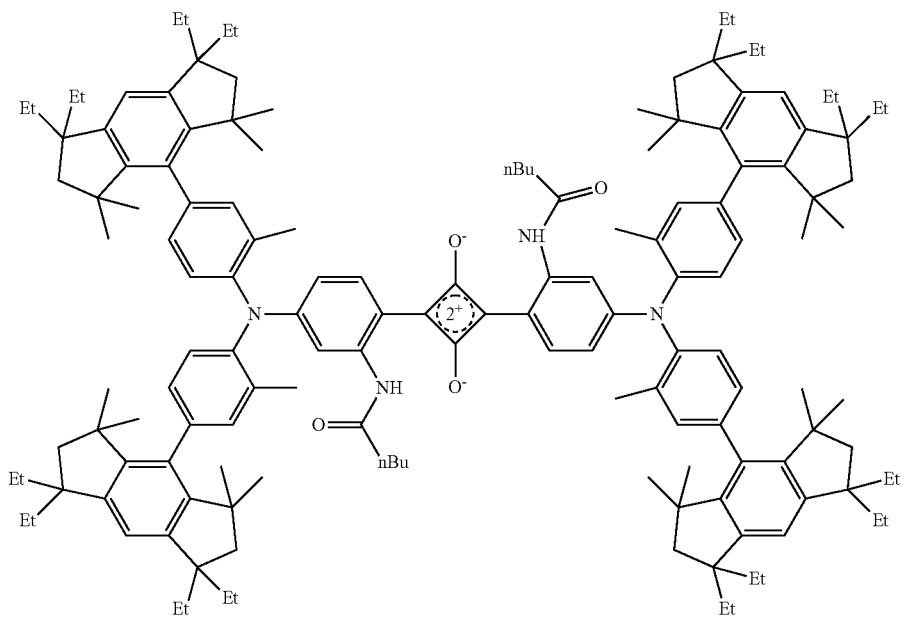
Da-66
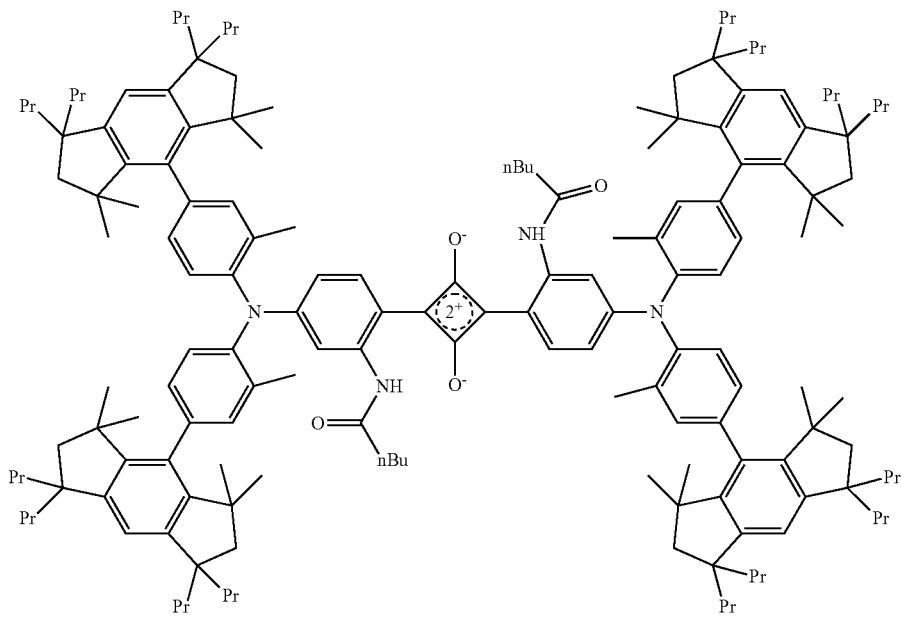

-continued
Da-67
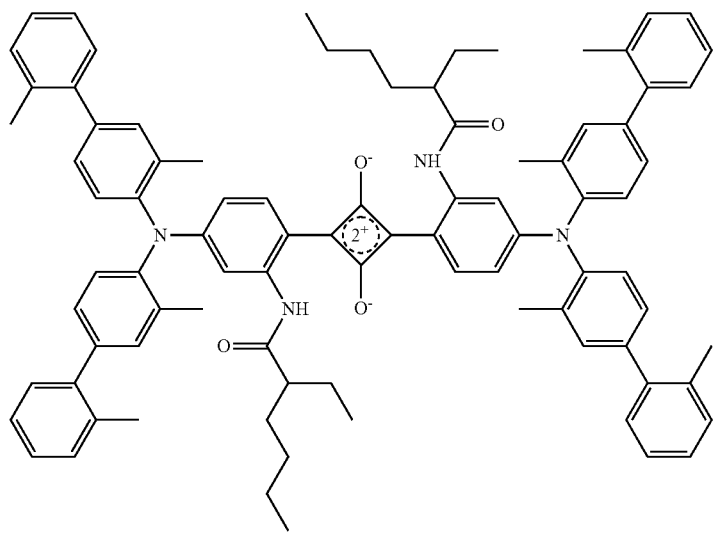
Da-68
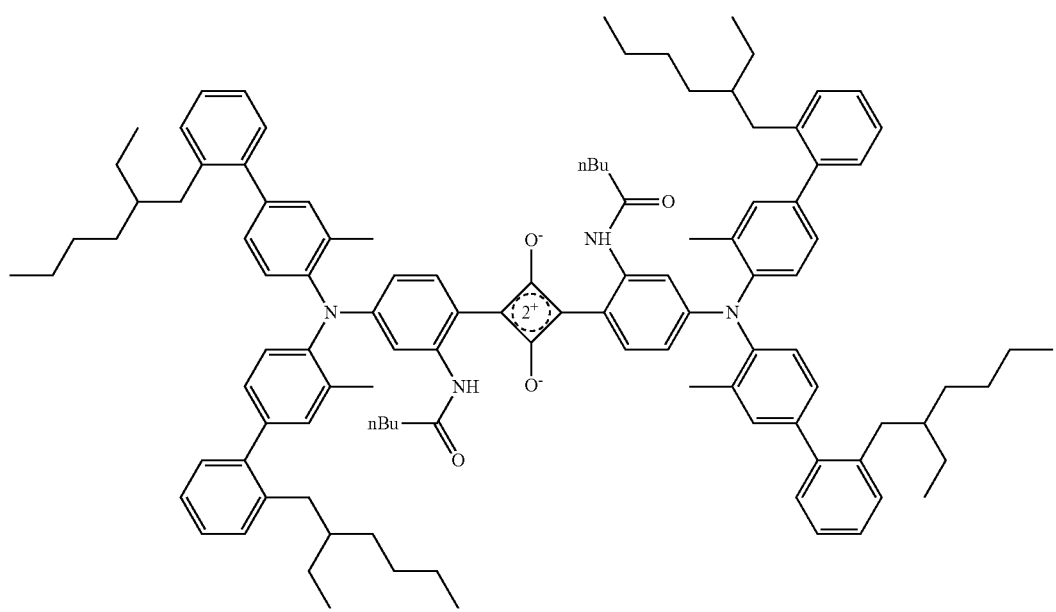

-continued
Da-69
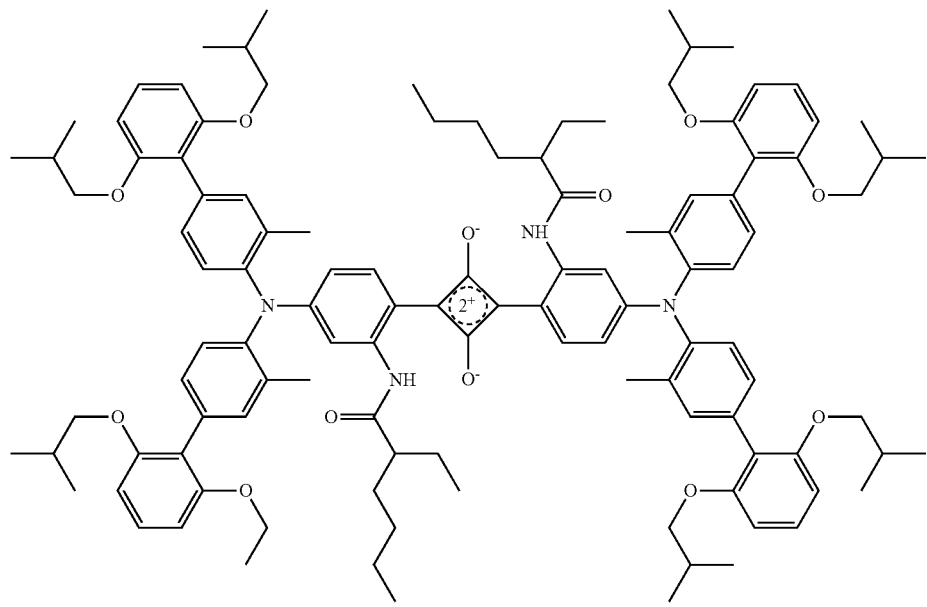
Da-70
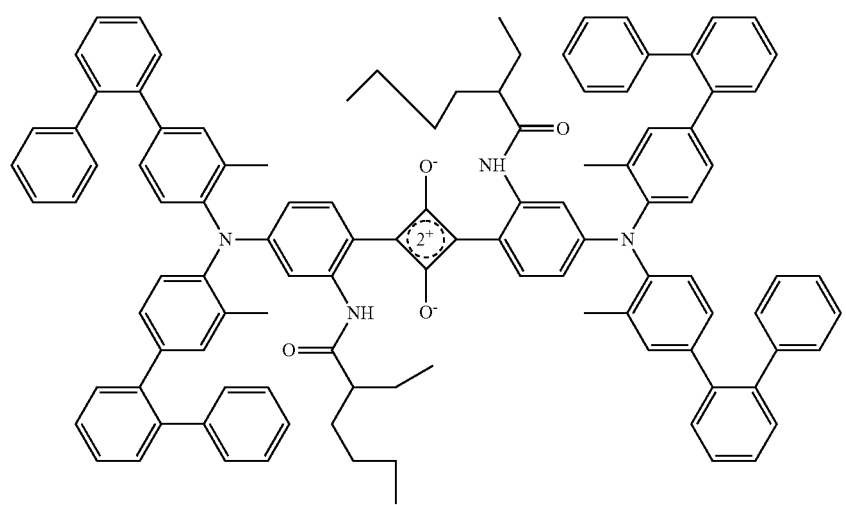

-continued
Da-71
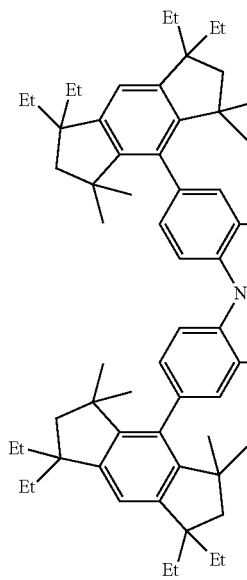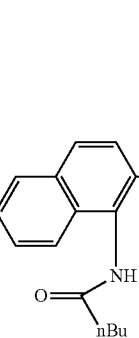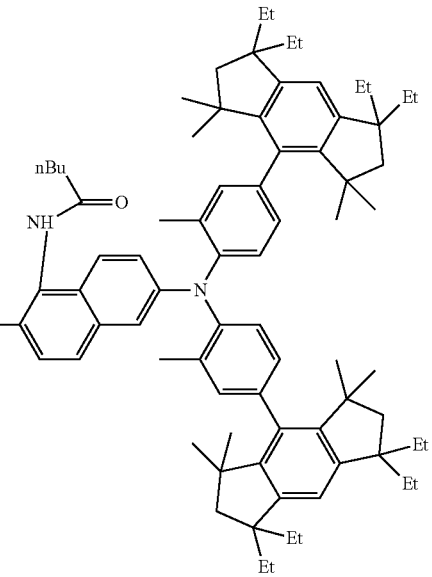
Da-72
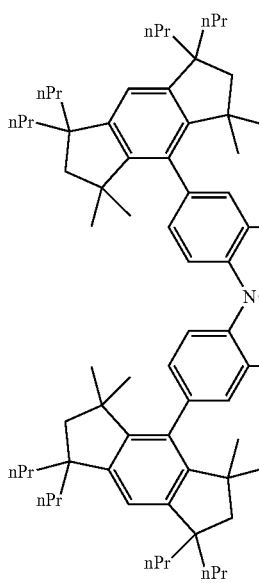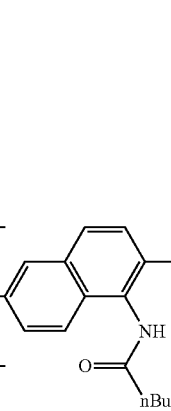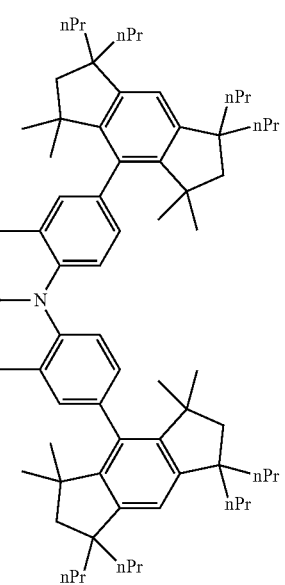

-continued
Da-73
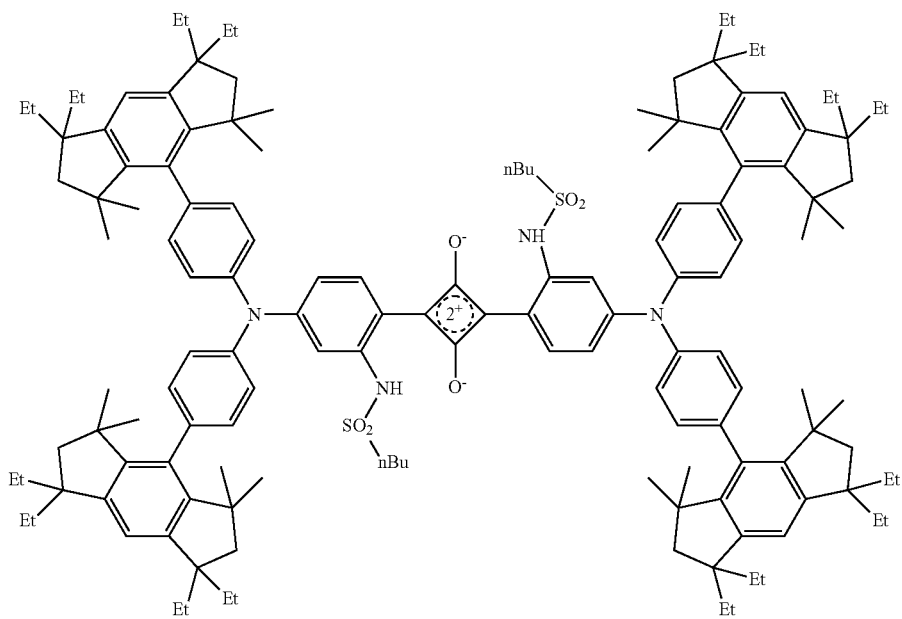
Da-74
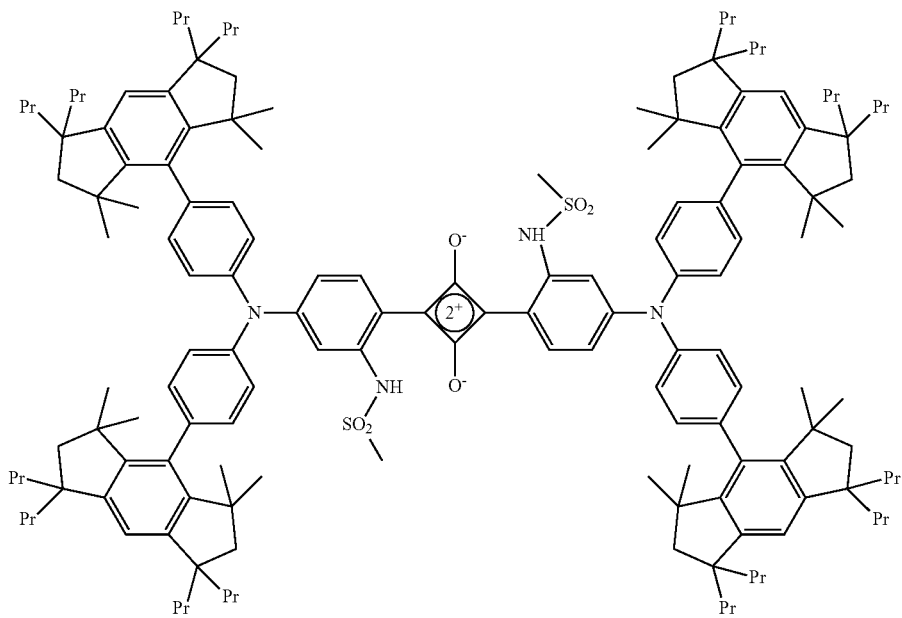

-continued
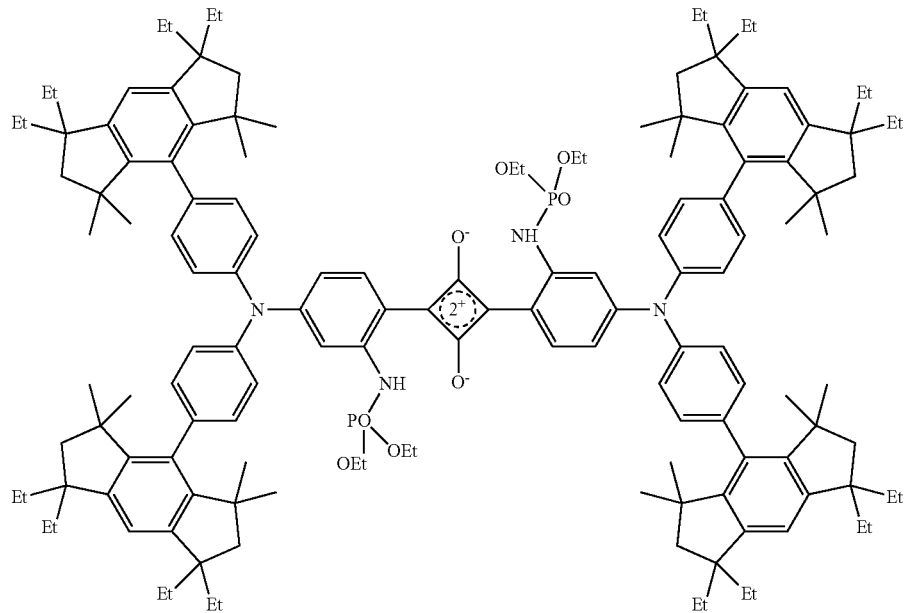
Da-75
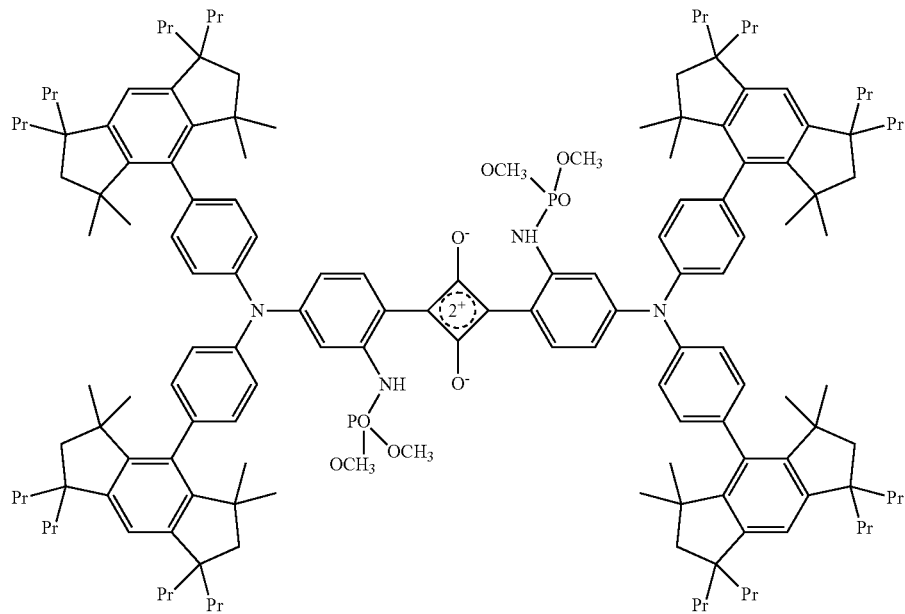
Da-76

-continued
Db-1
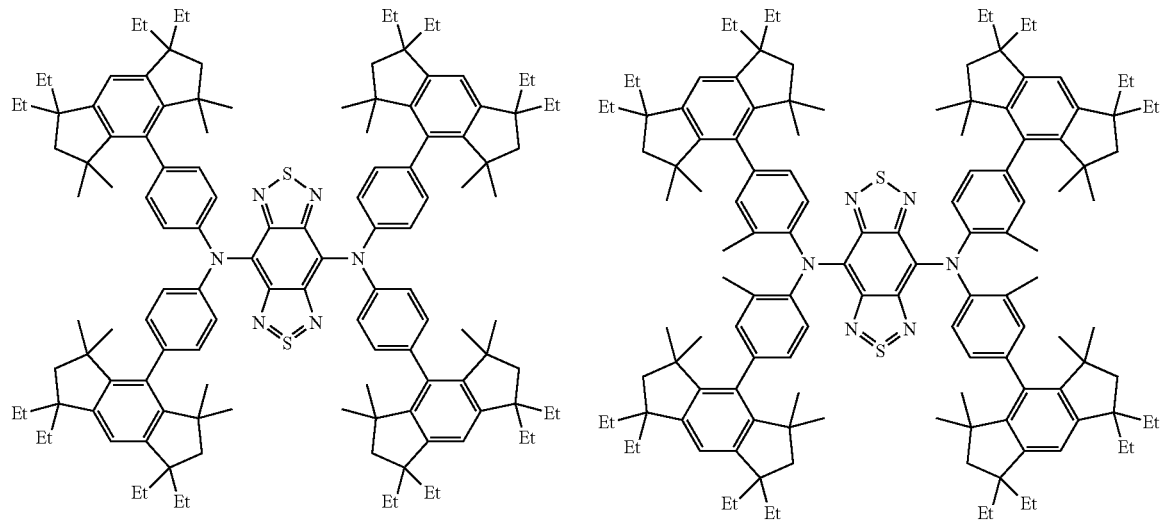
Db-2
Db-3
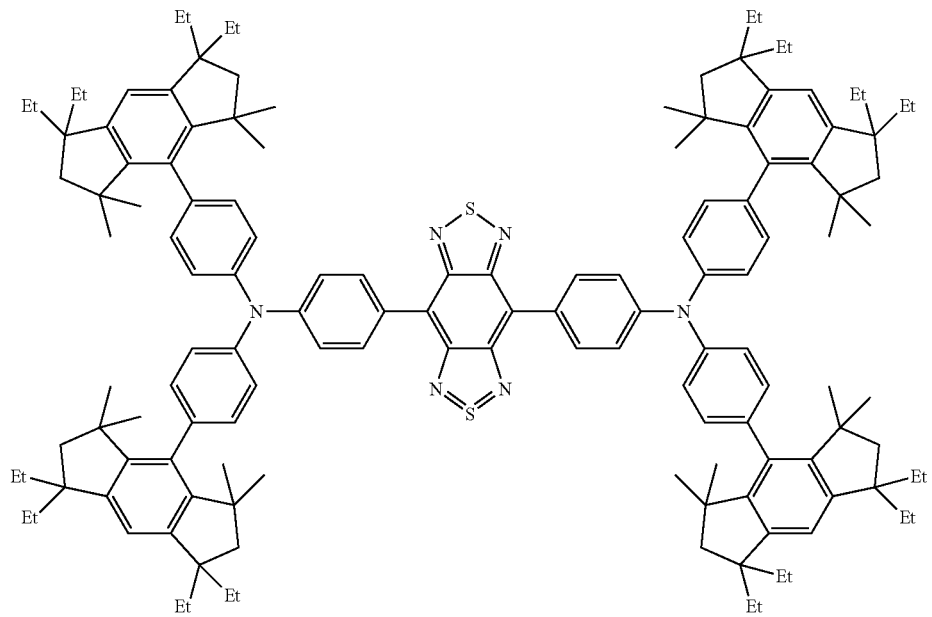

-continued
Db-4
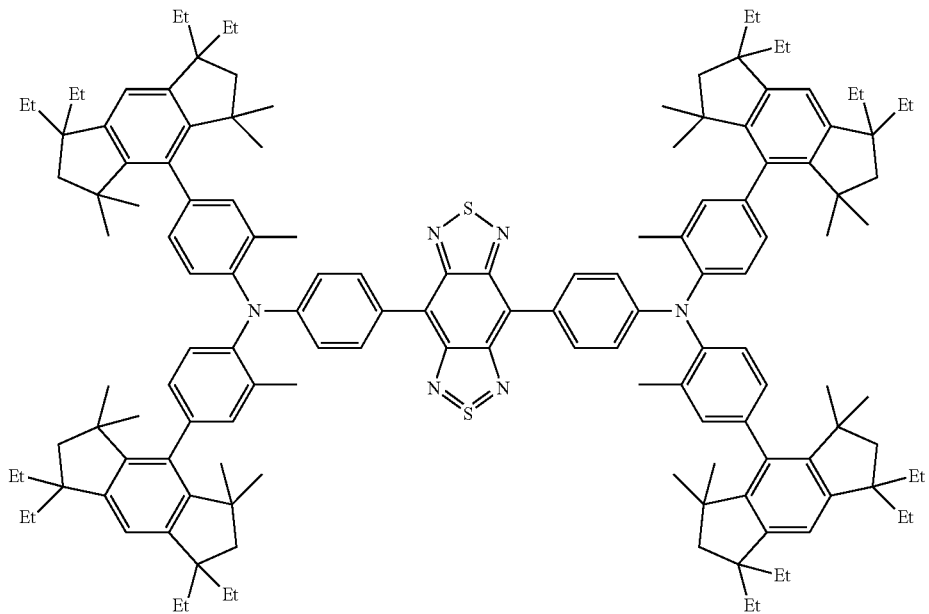
Db-5
Db-6
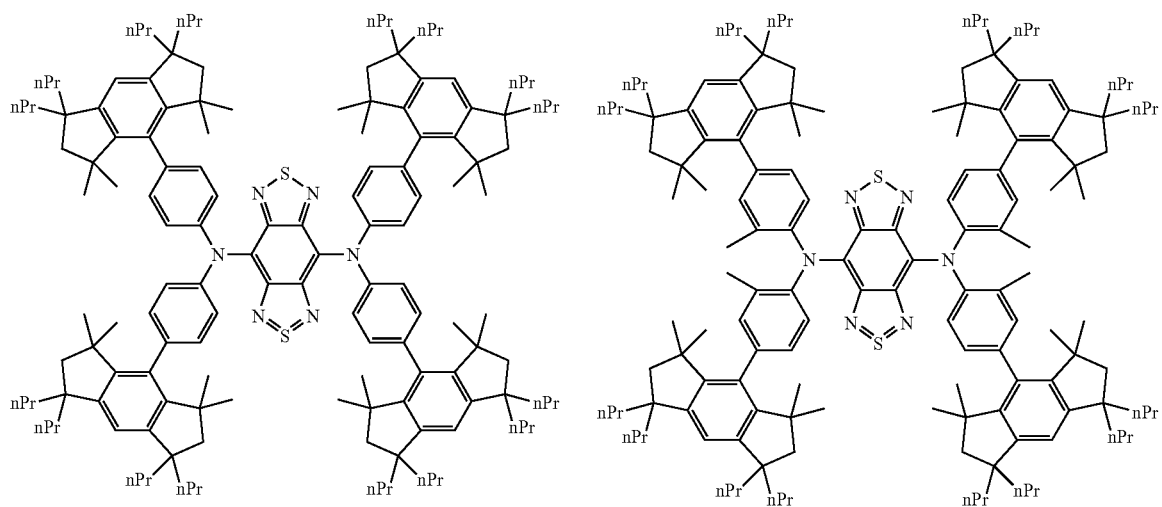

-continued
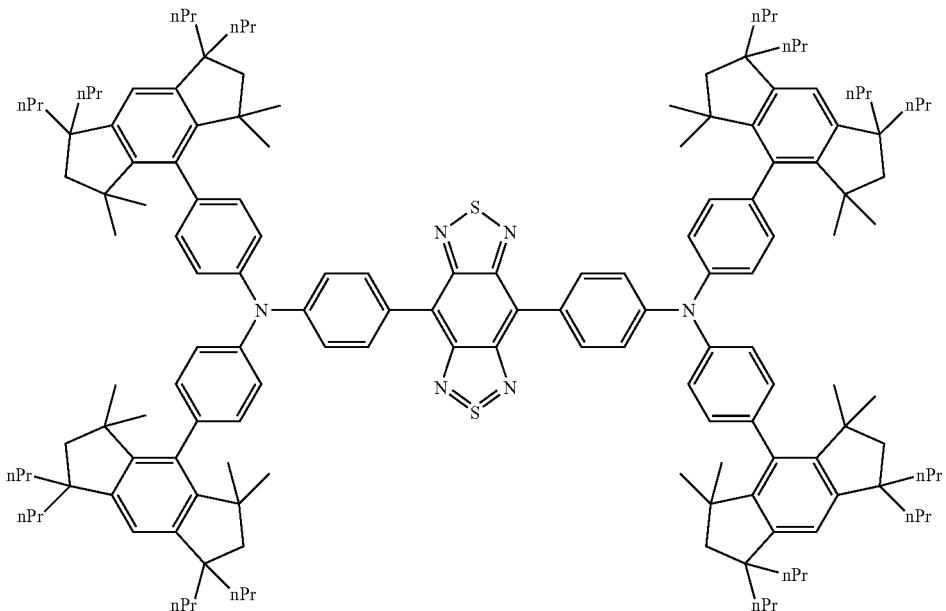
Db-7
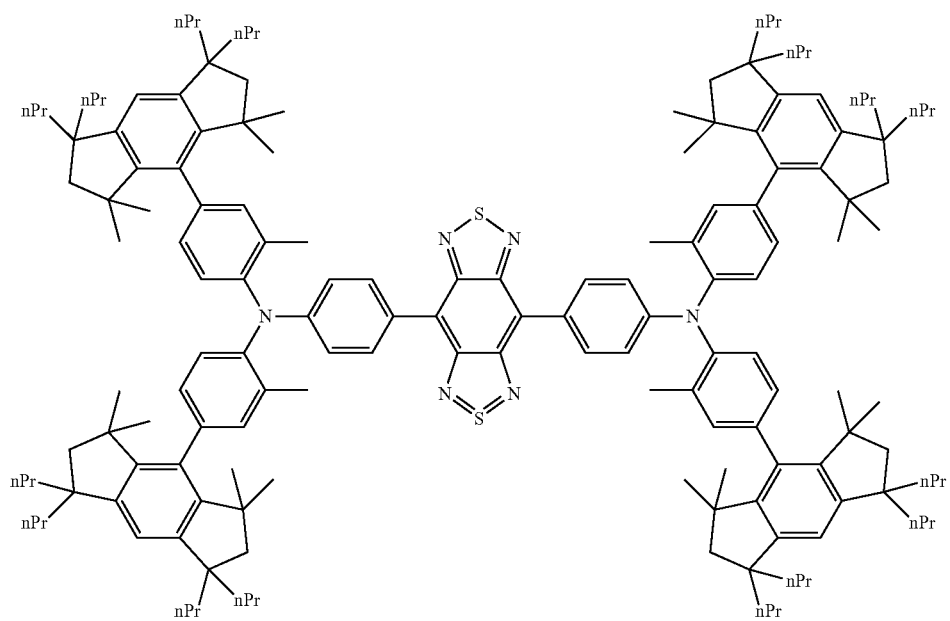
Db-8

-continued
Db-9
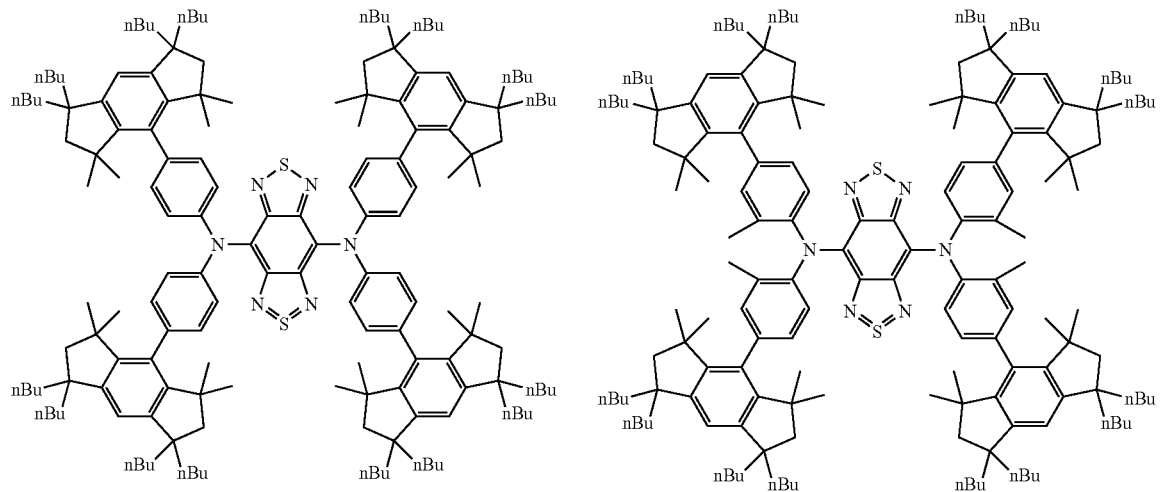
Db-10
Db-11
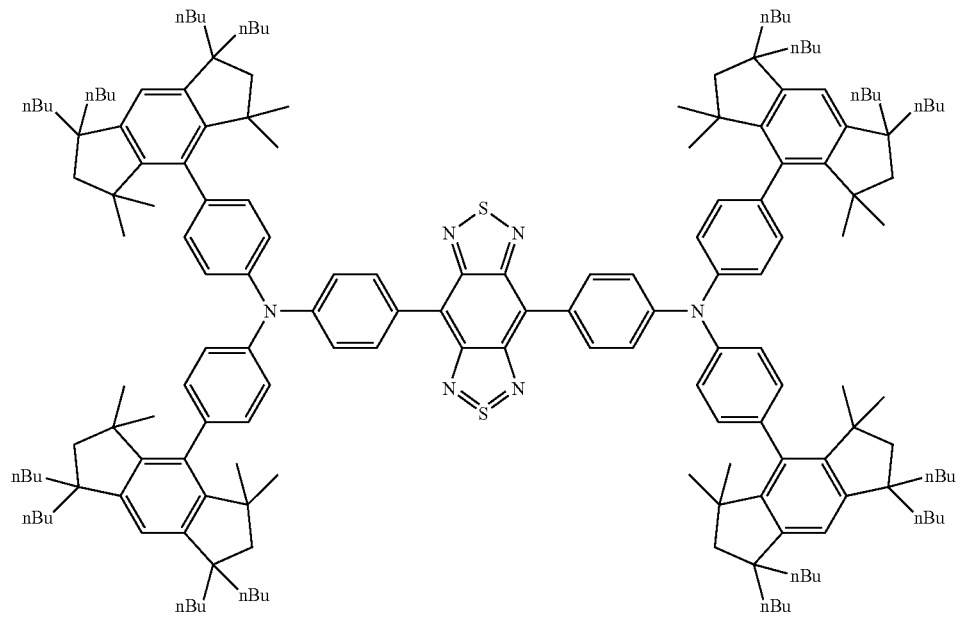

Db-12
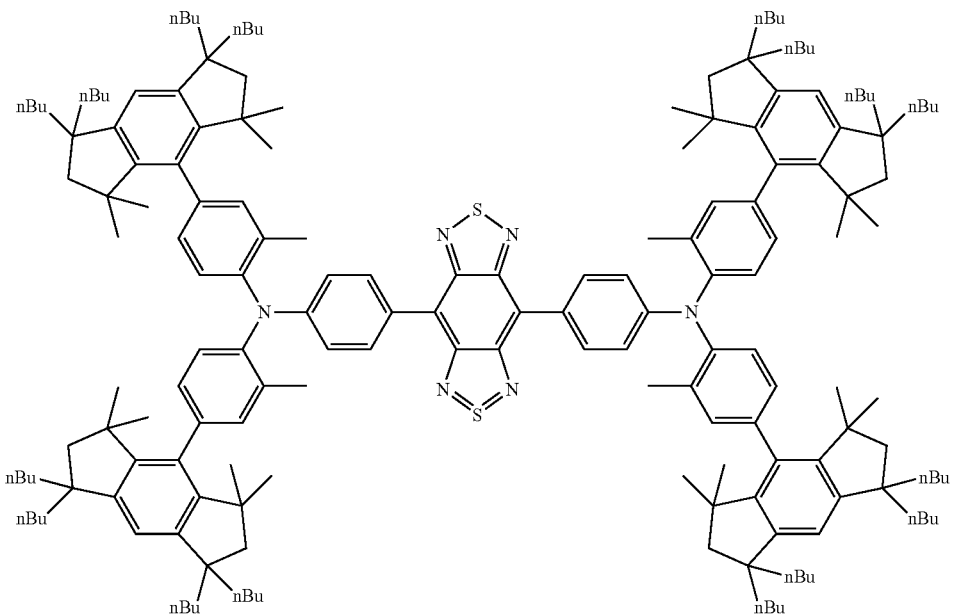
Db-13
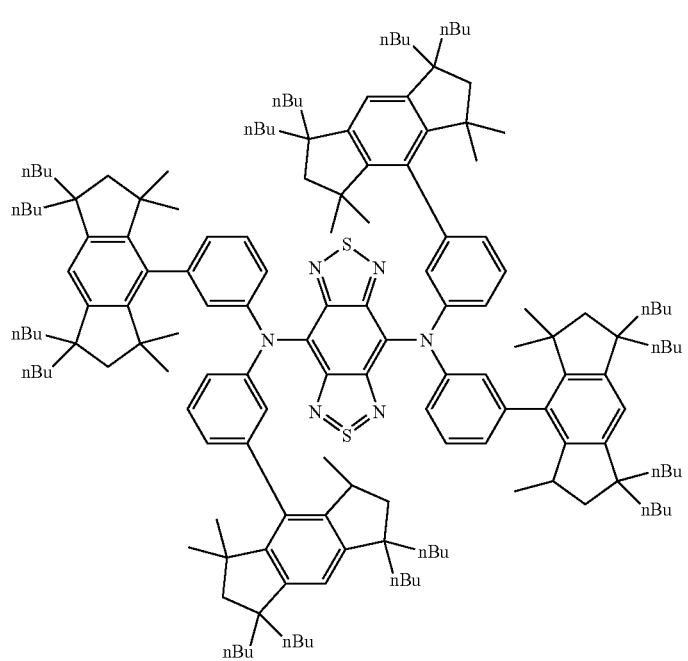

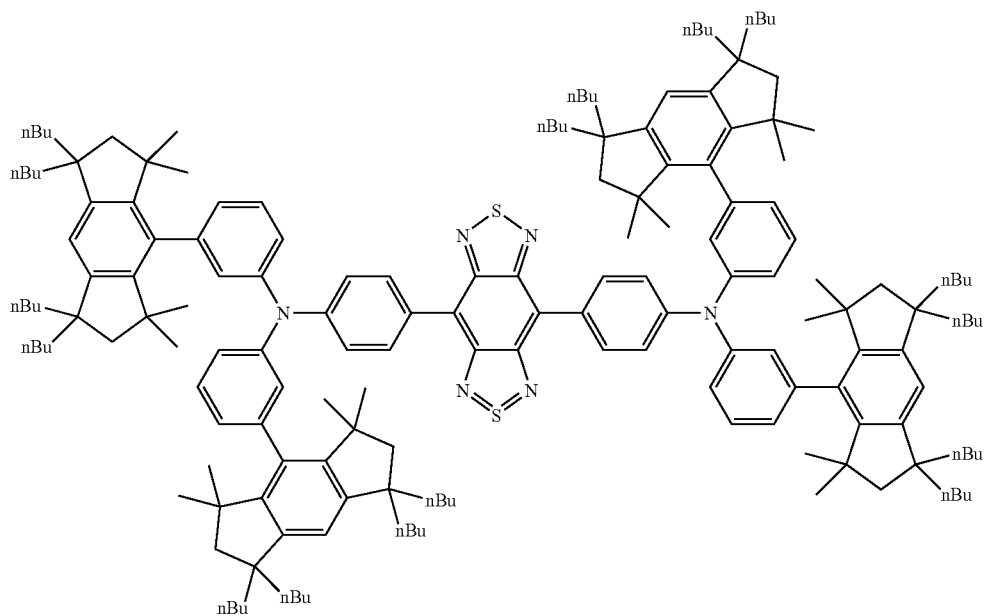
Db-14
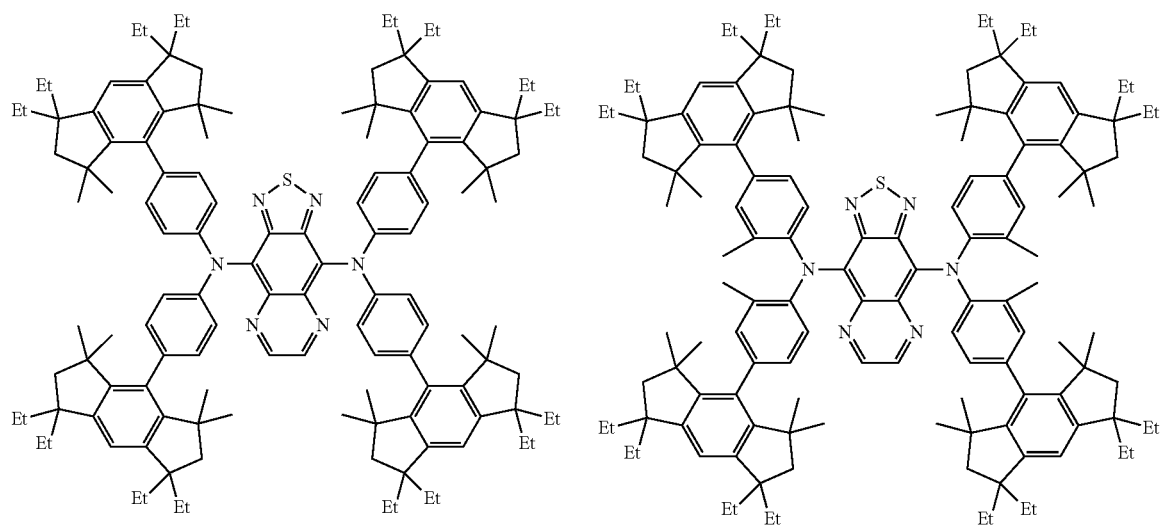
Dc-1
Dc-2

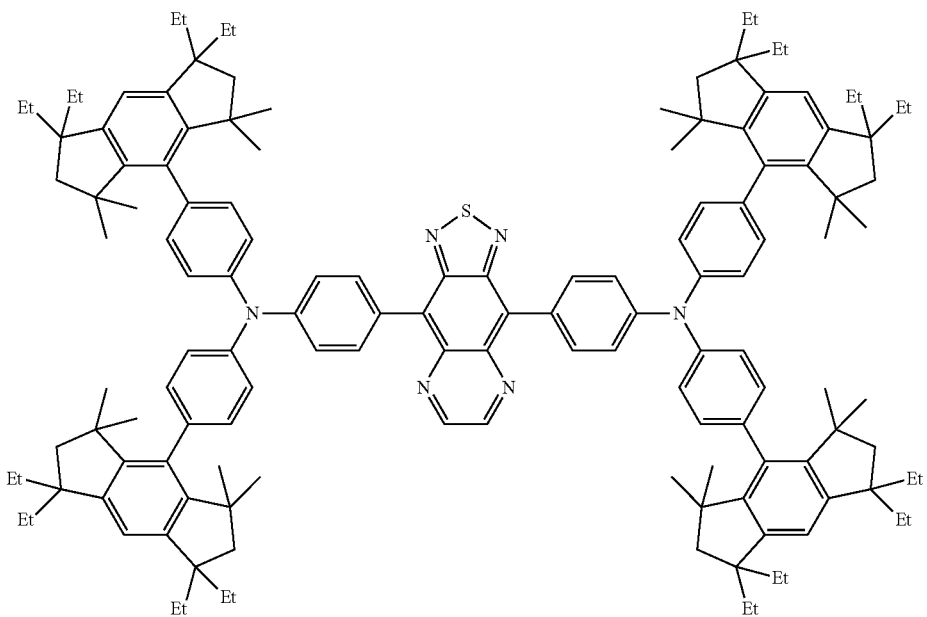
Dc-3
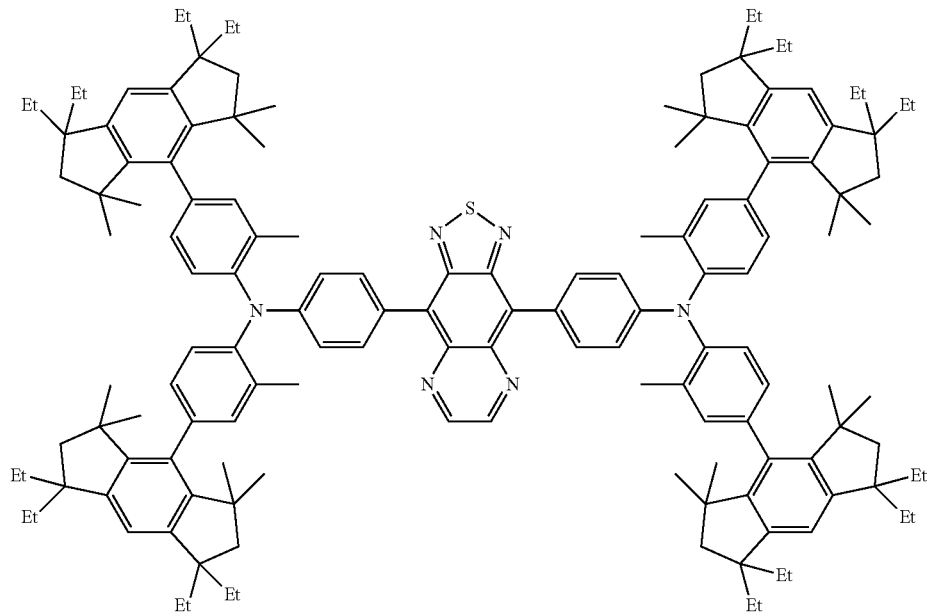
Dc-4

-continued
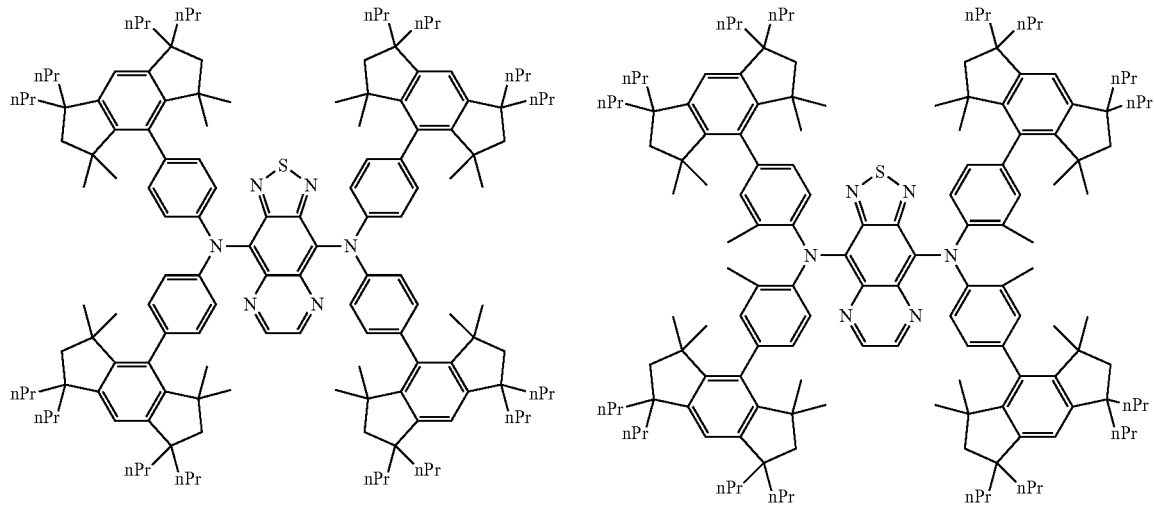
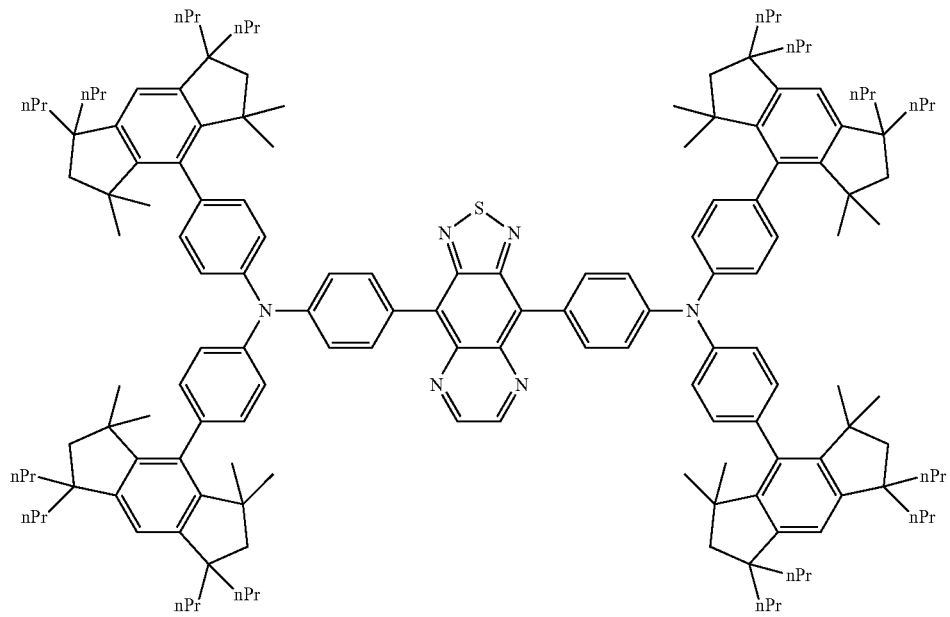

103
104
-continued
Dc-8
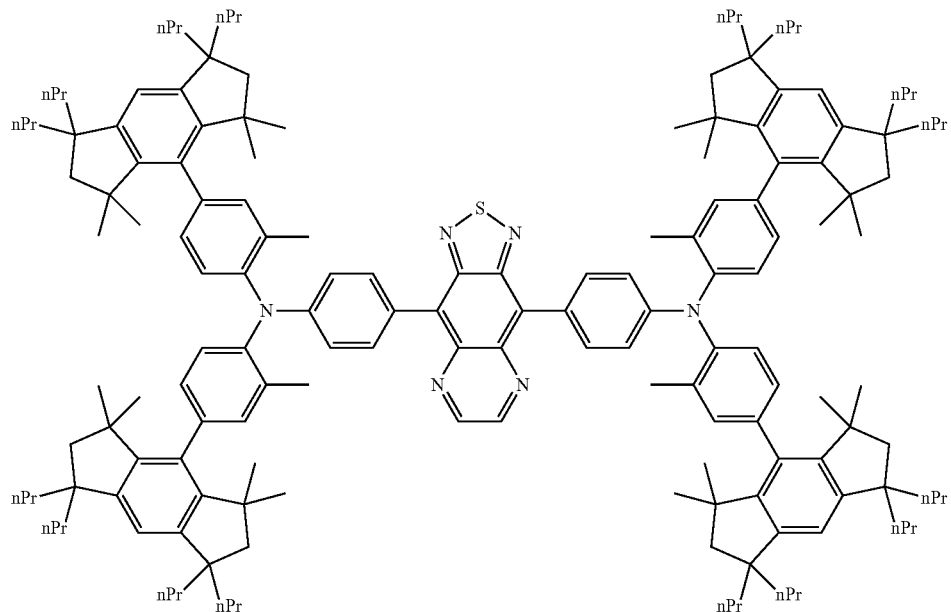
Dc-9
Dc-10
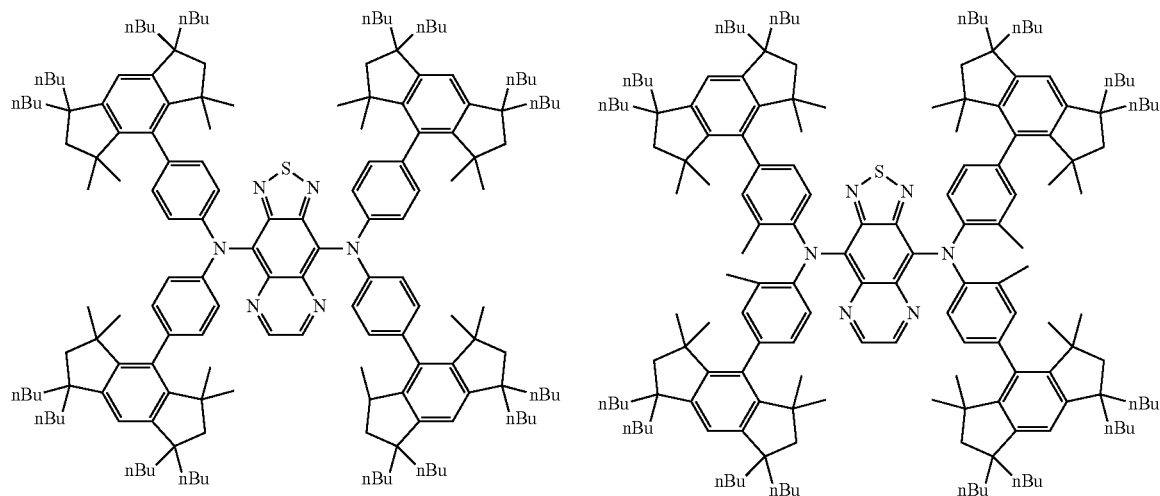

Dc-11
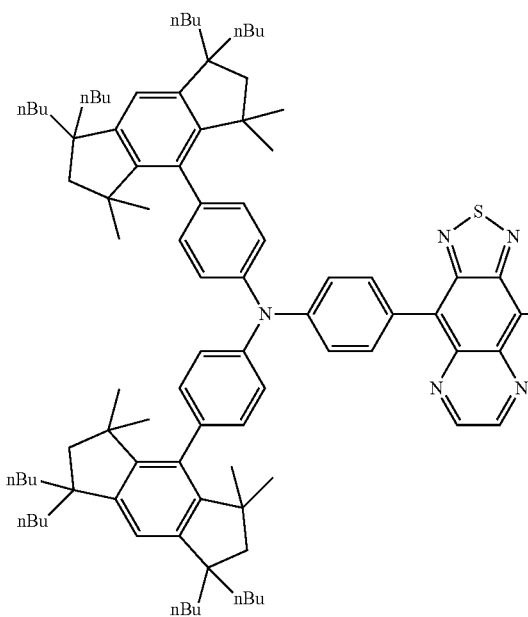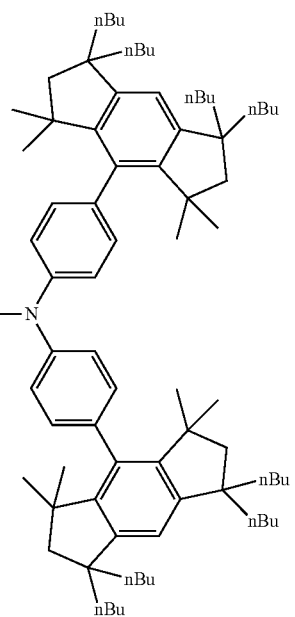
Dc-12
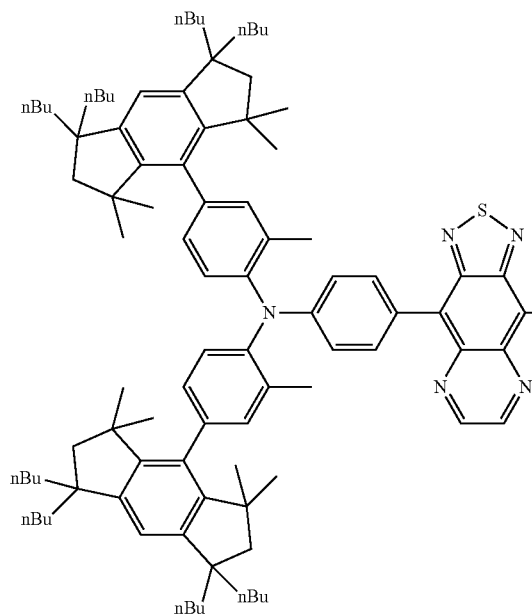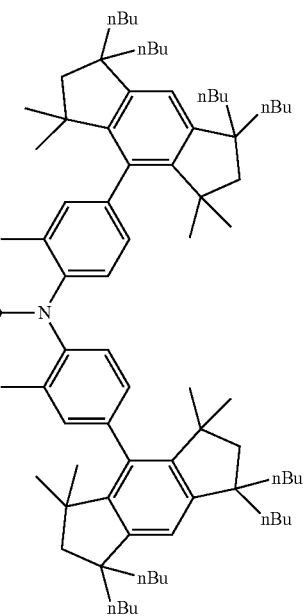

-continued
Dc-13
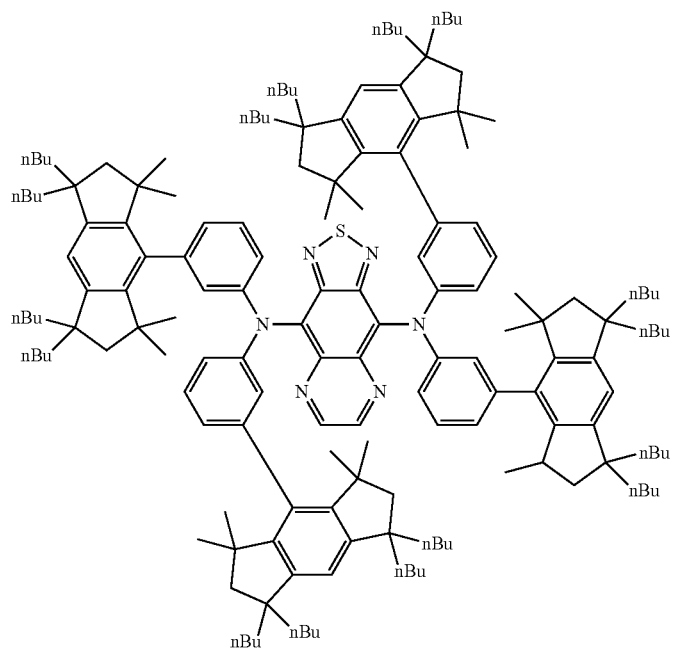
Dc-14
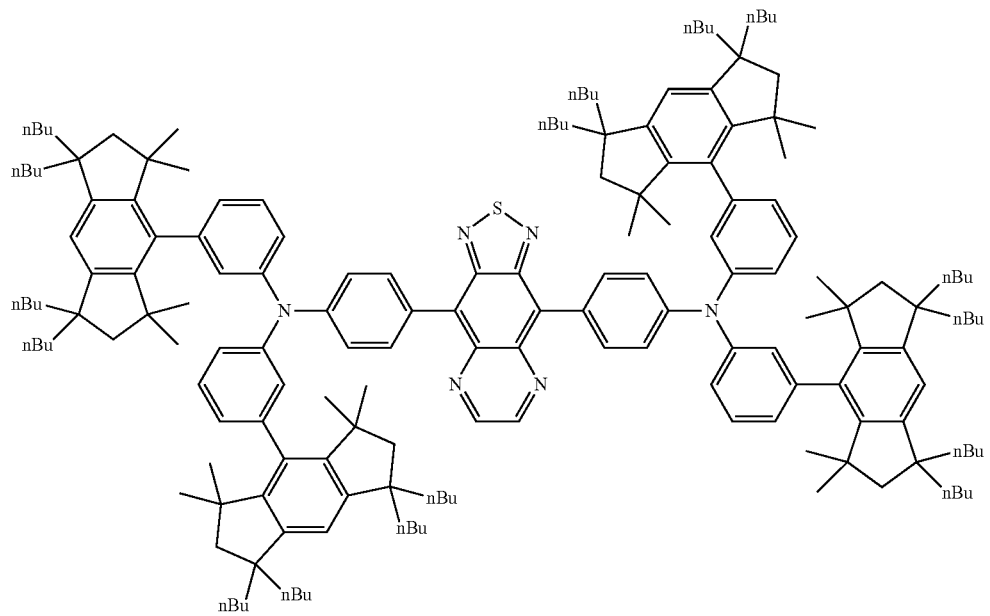

-continued
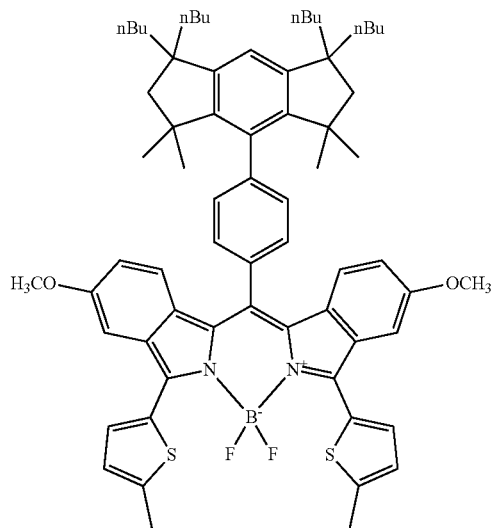
Dd-1
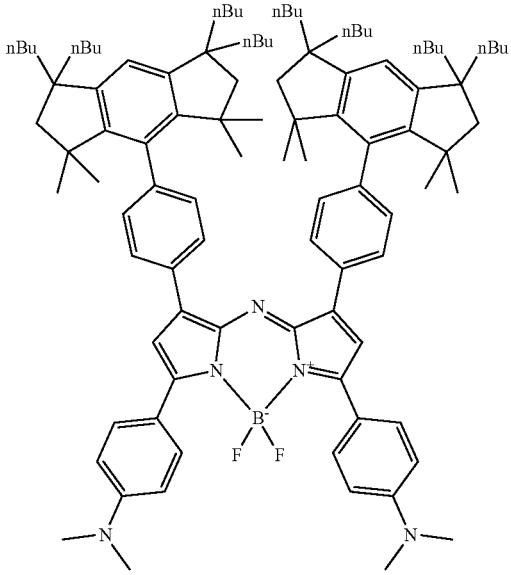
Dd-2
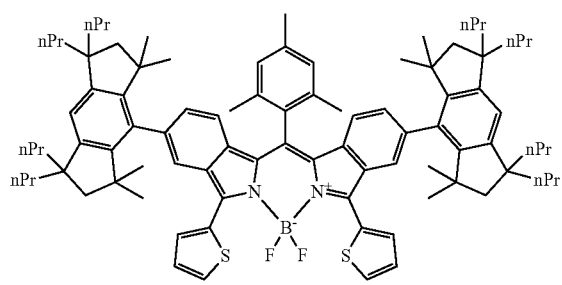
Dd-3
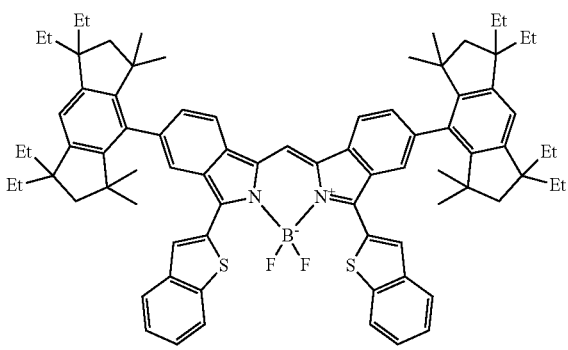
Dd-4
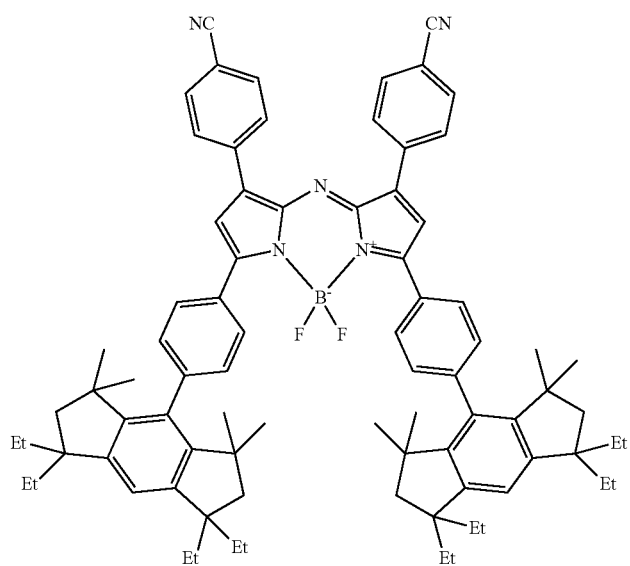
Dd-5

-continued
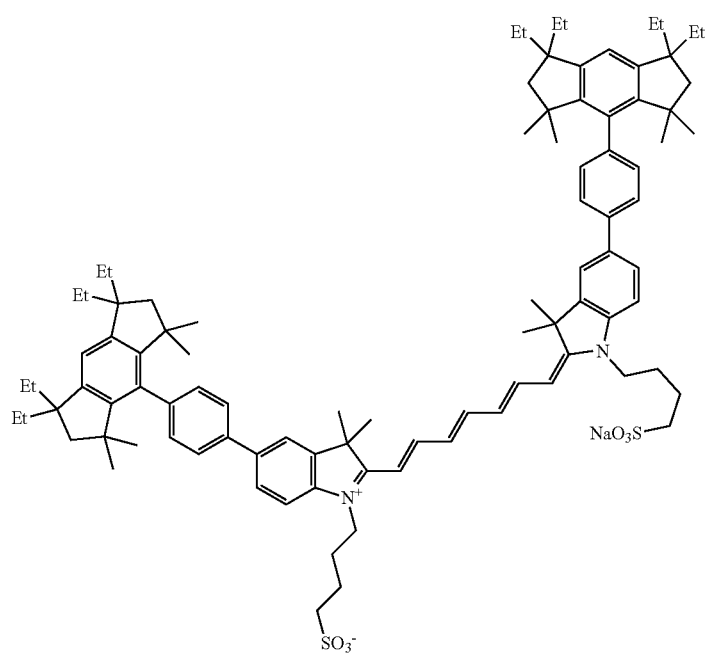
De-1
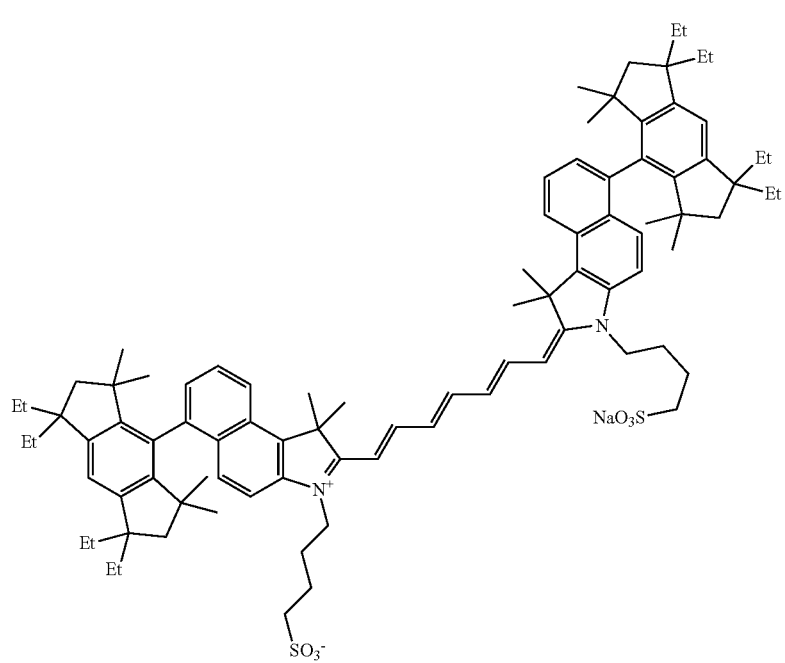
De-2

-continued
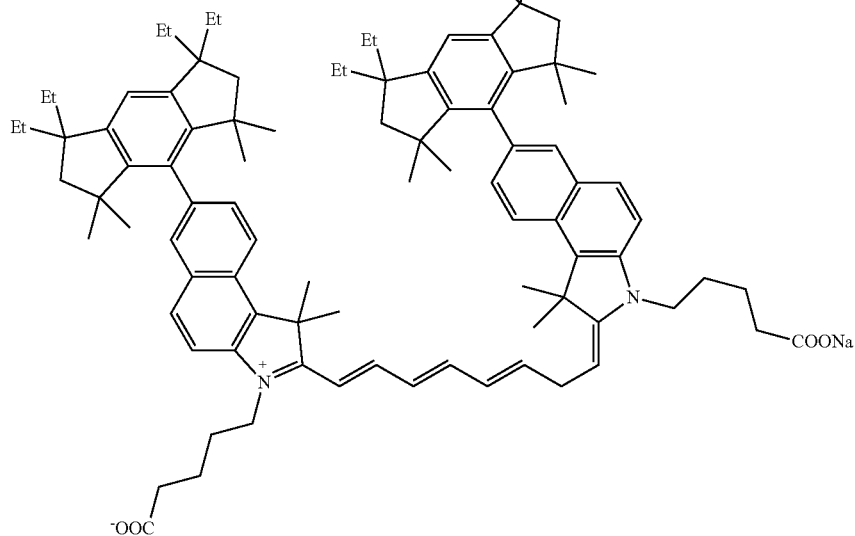
De-3
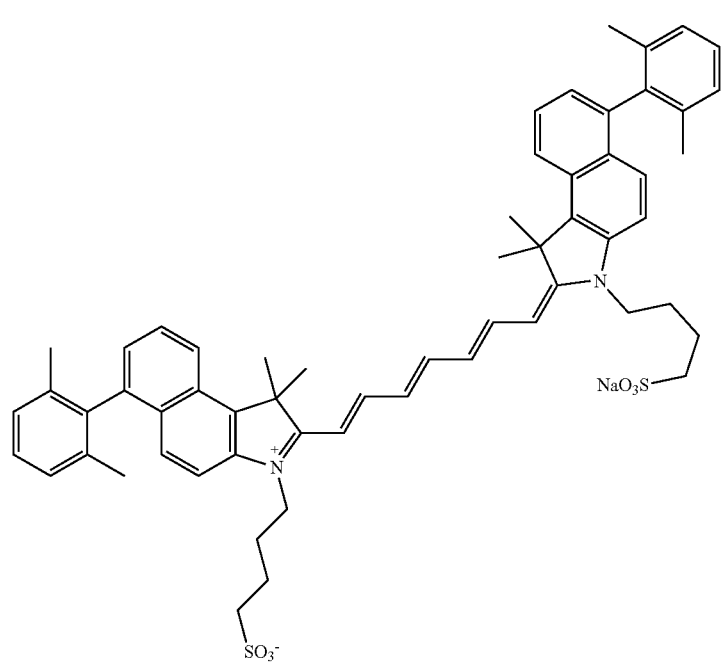
De-4

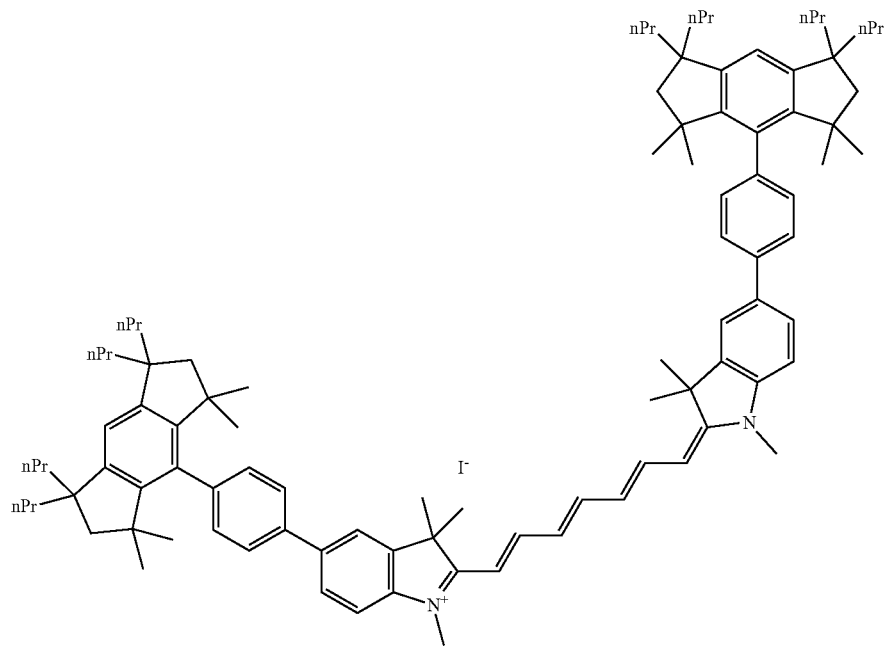
De-5
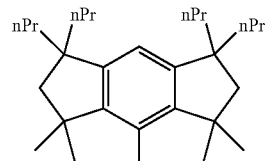
De-6
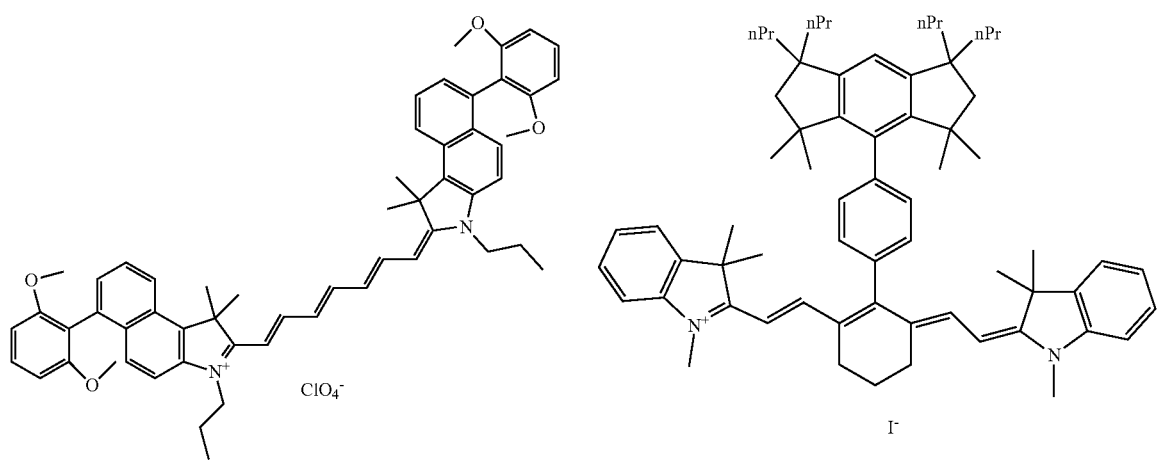
De-7

-continued
Df-1
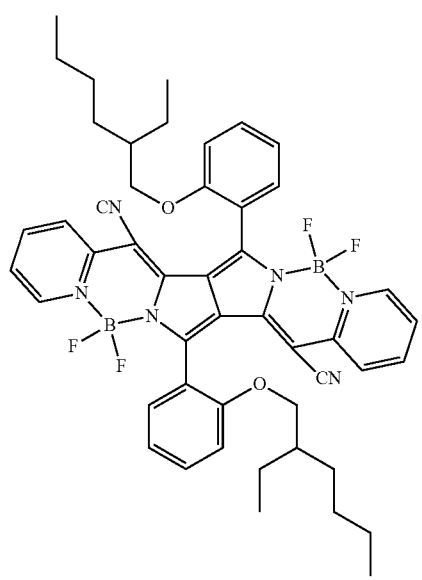
Df-2
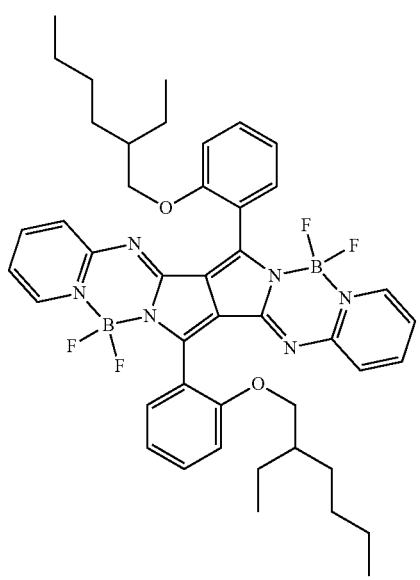
Df-3
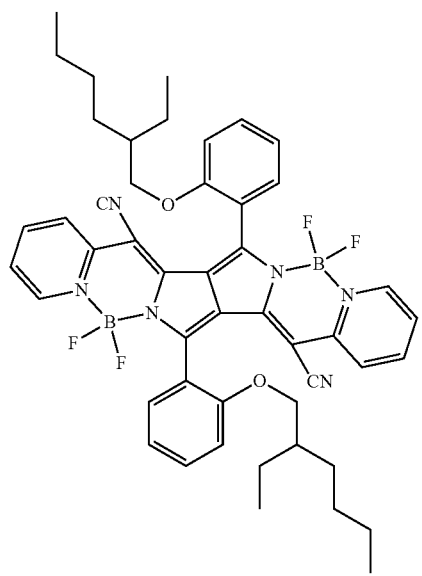
Df-4
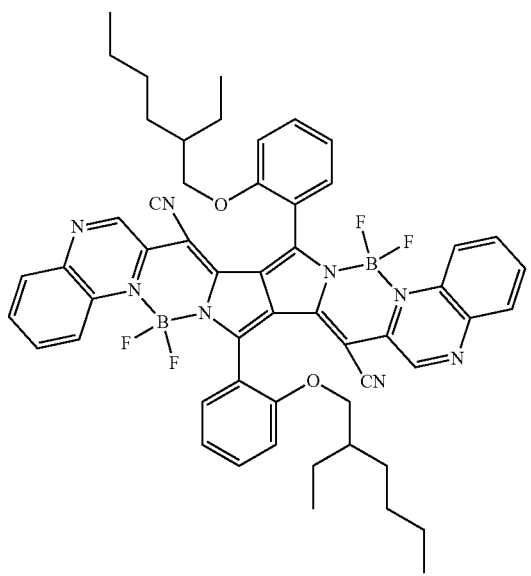

-continued
Df-5
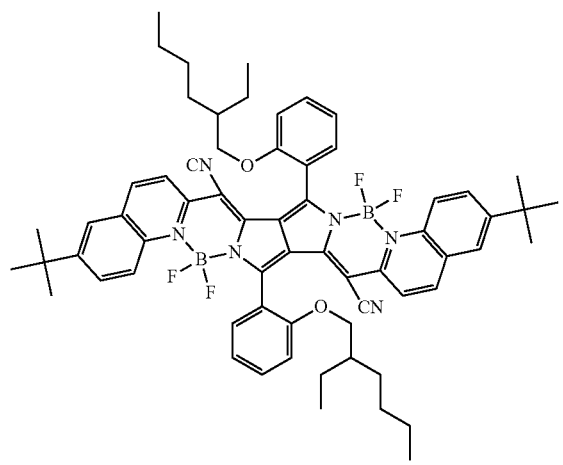
Df-6
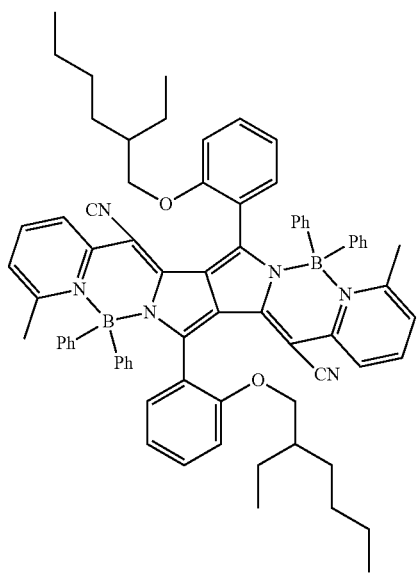
Df-7
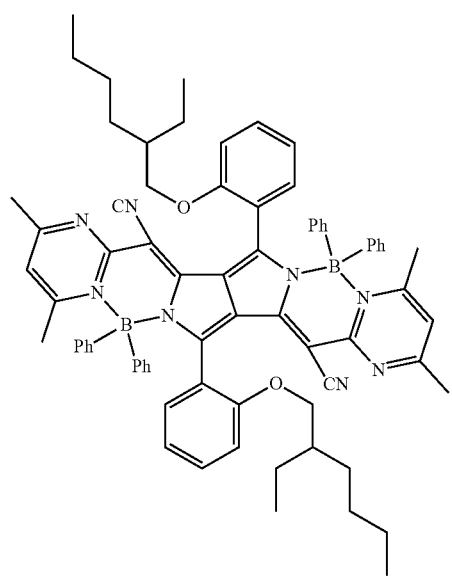
Df-8
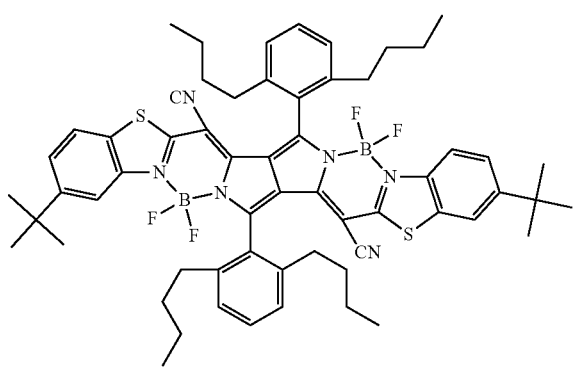

-continued
Df-9
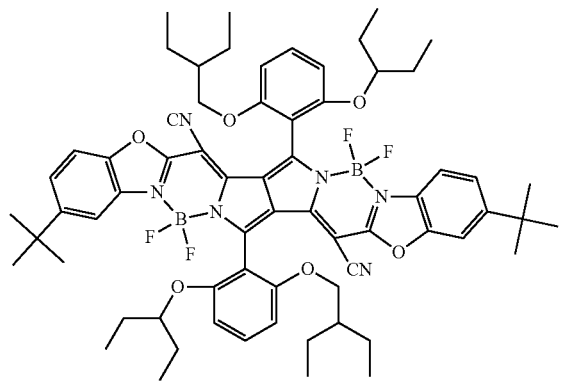
Df-10
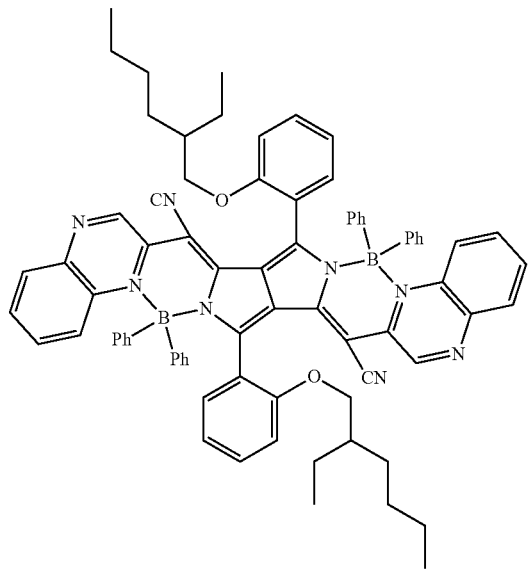
Df-11
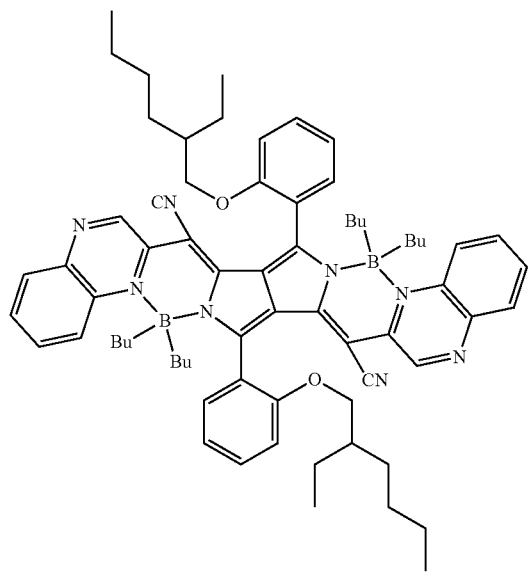
Df-12
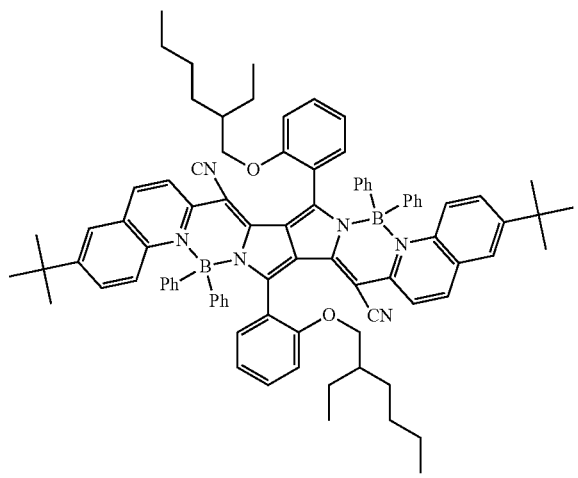

-continued
Df-13
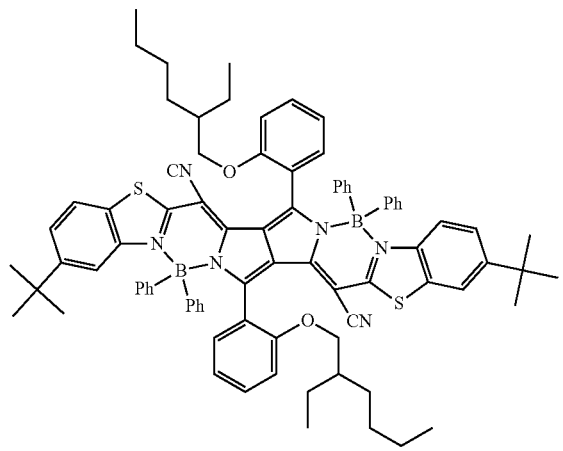
Df-14
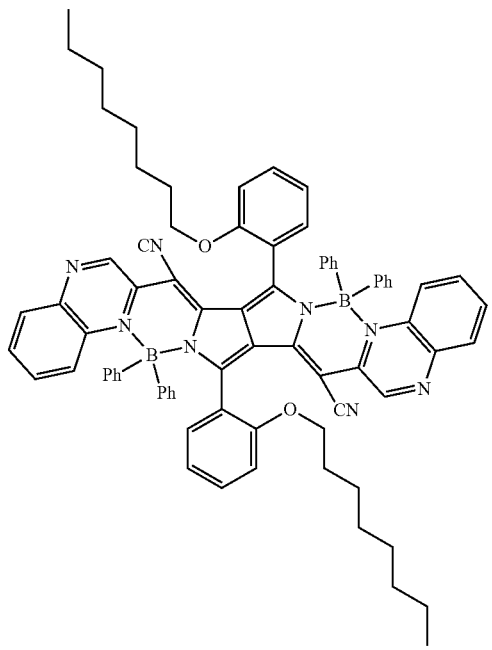
Df-15
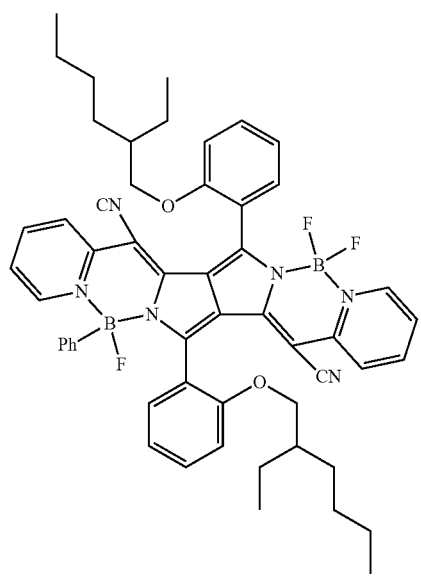
Df-16
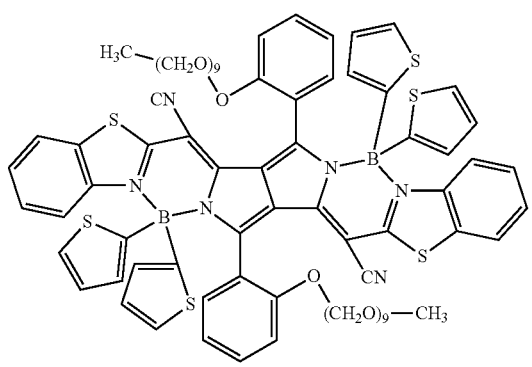

125 126
-continued
Df-17
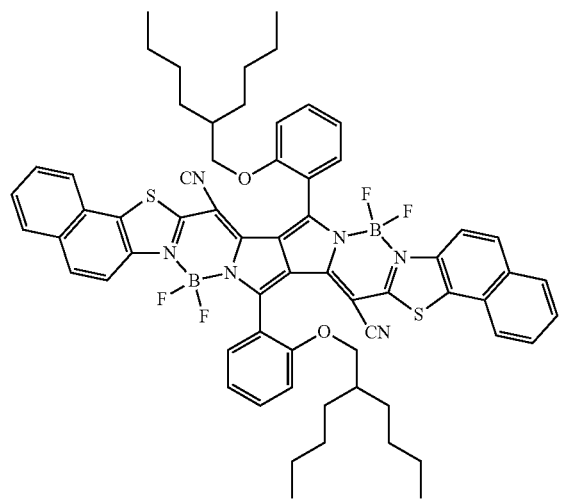
Df-18
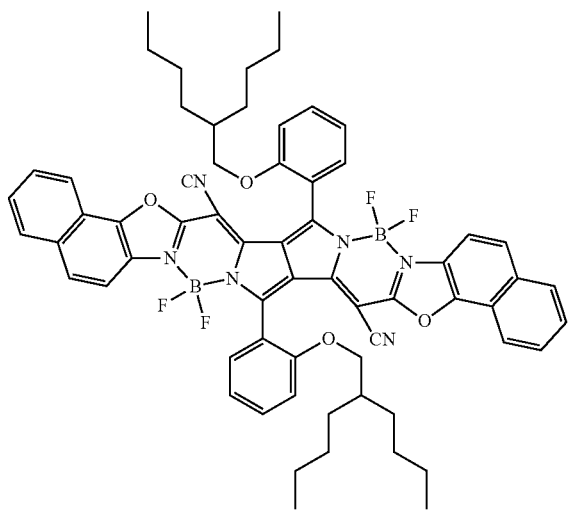
Df-19
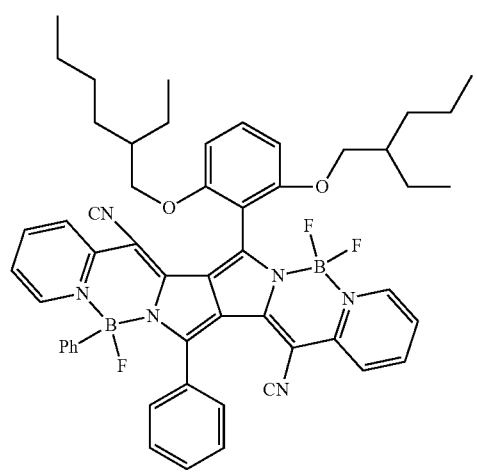
Df-20
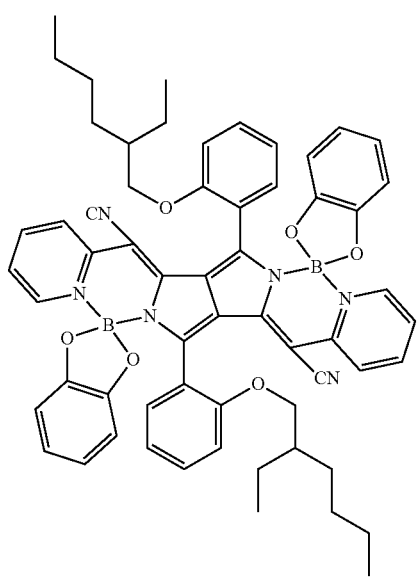
Df-21
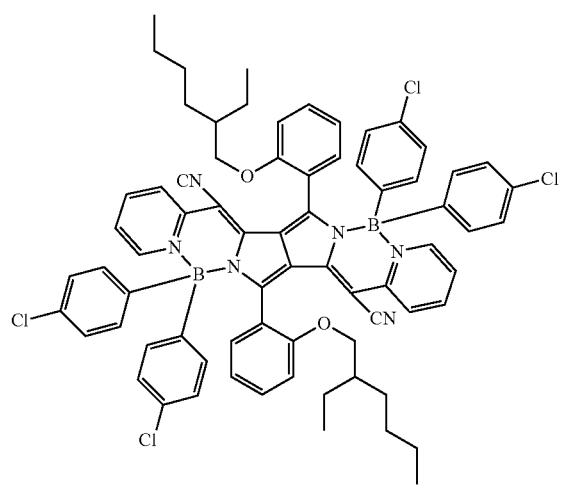
Df-22
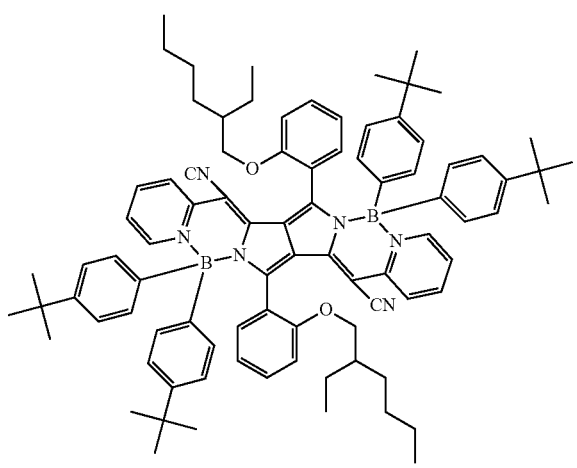

-continued
Df-23
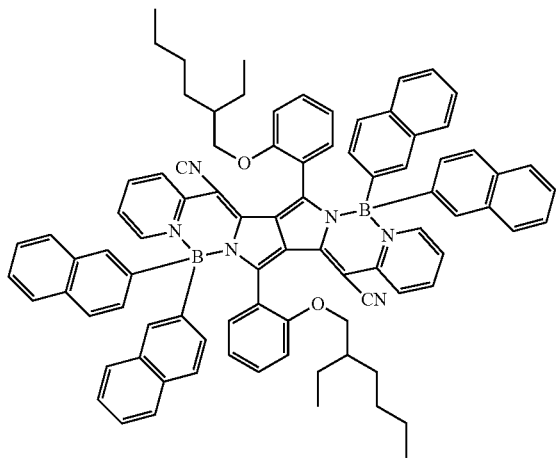
Df-24
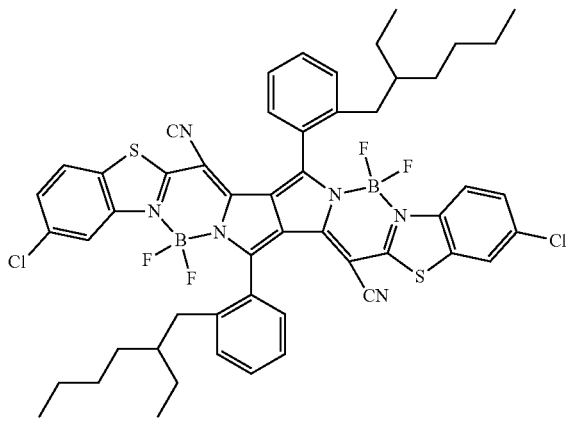
Df-25
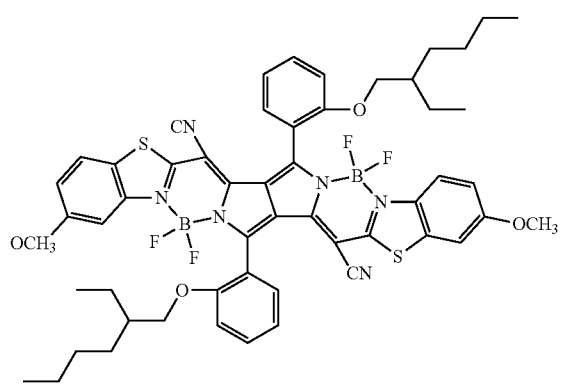
Df-26
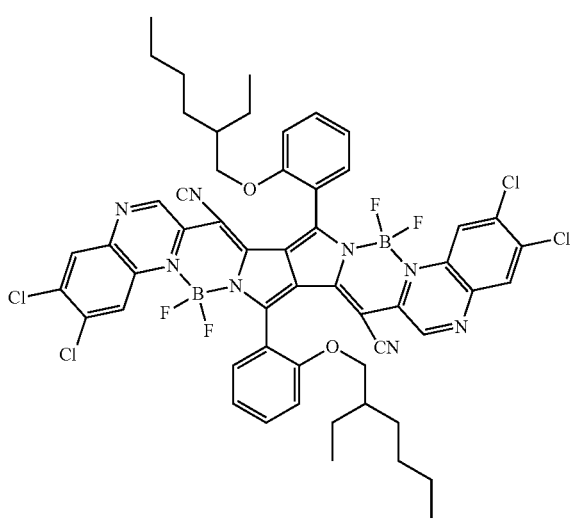
Df-27
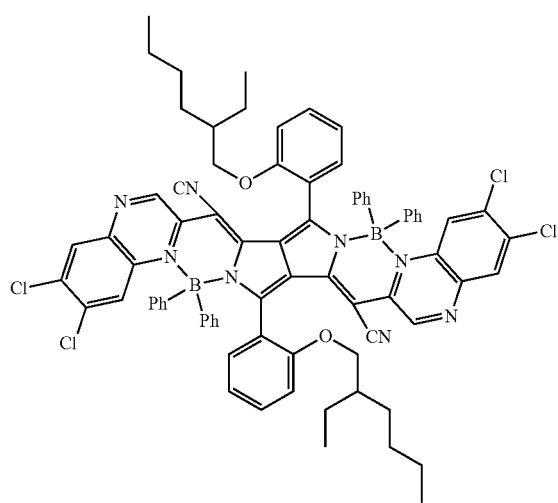
Df-28
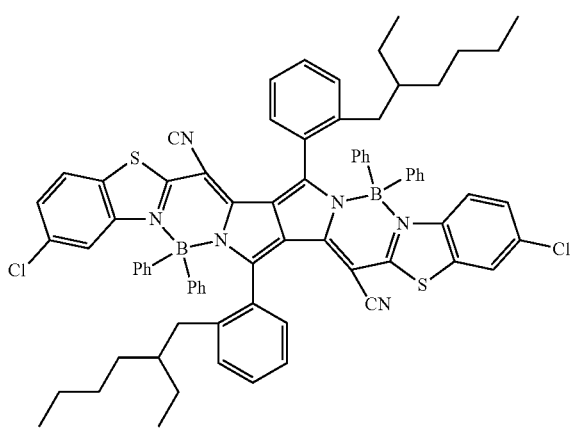

-continued
Df-29
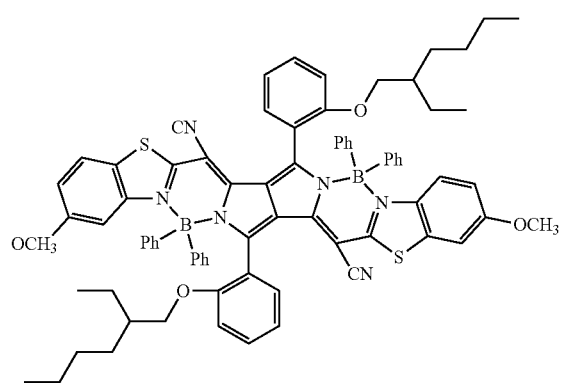
Df-30
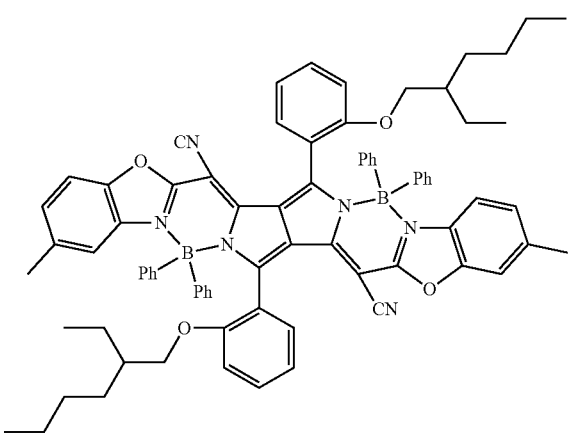
Df-31
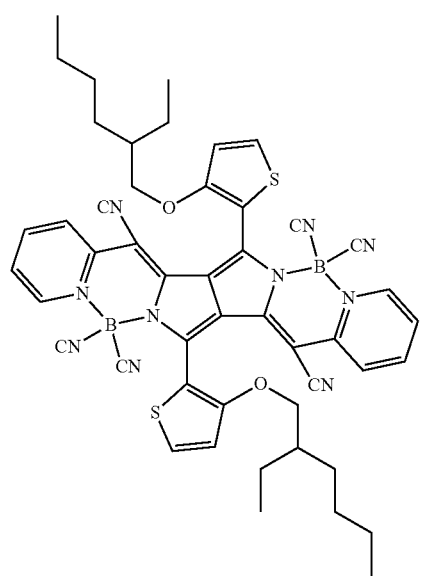
Df-32
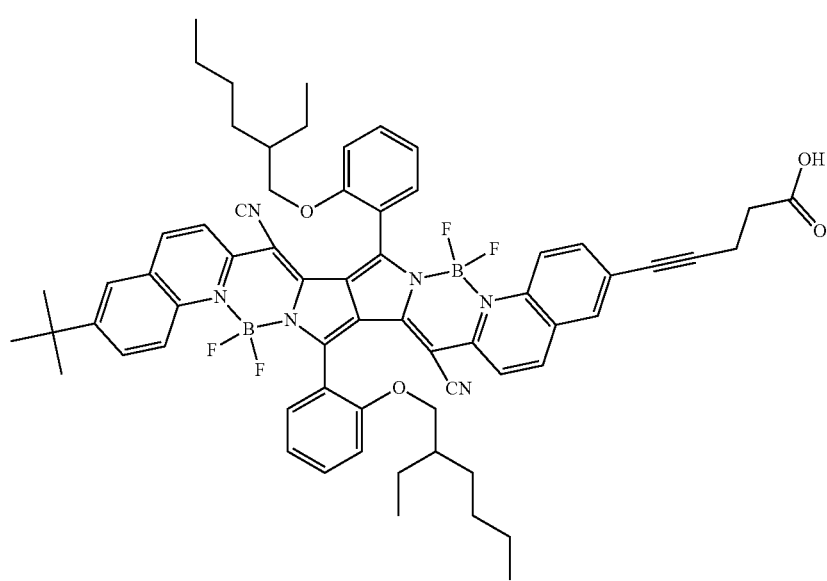

-continued
Df-33
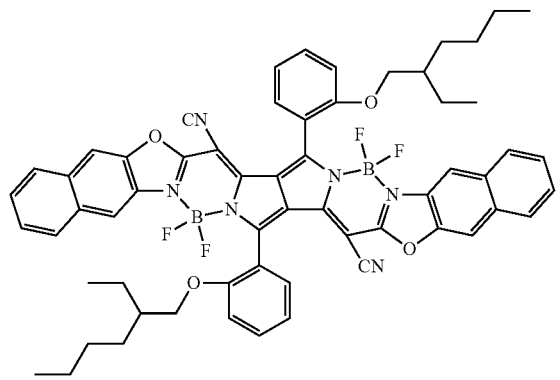
Df-34
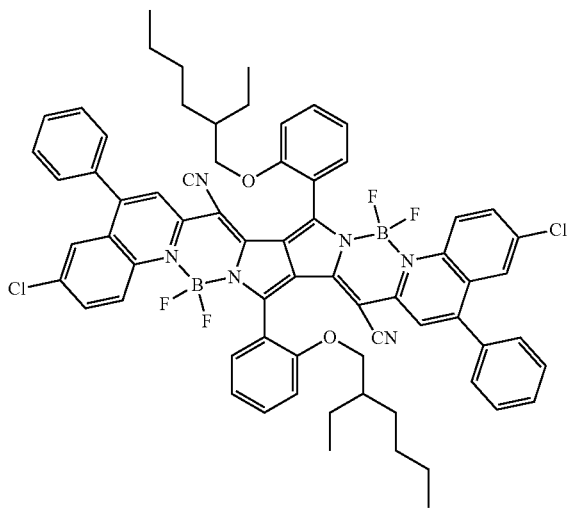
Df-35
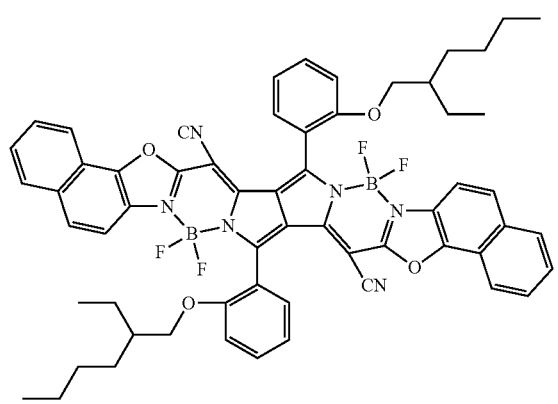
Df-36
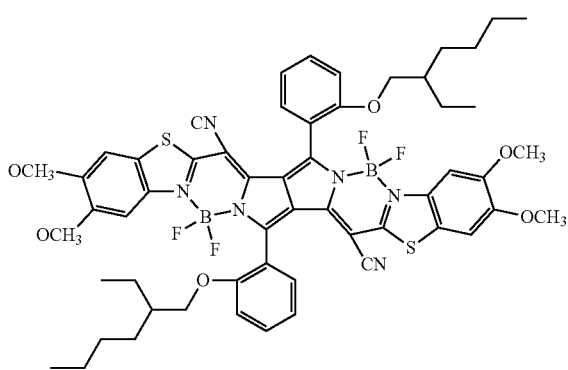
Df-37
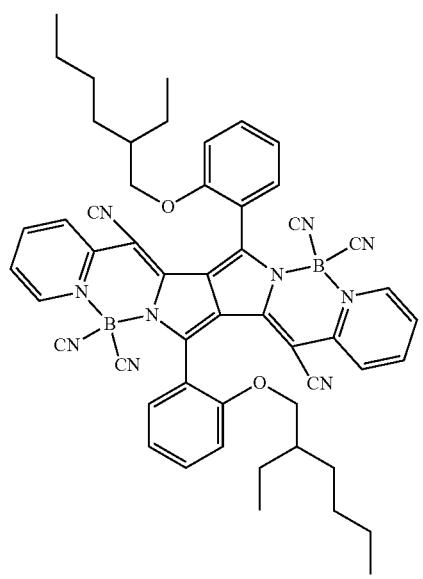
Df-38
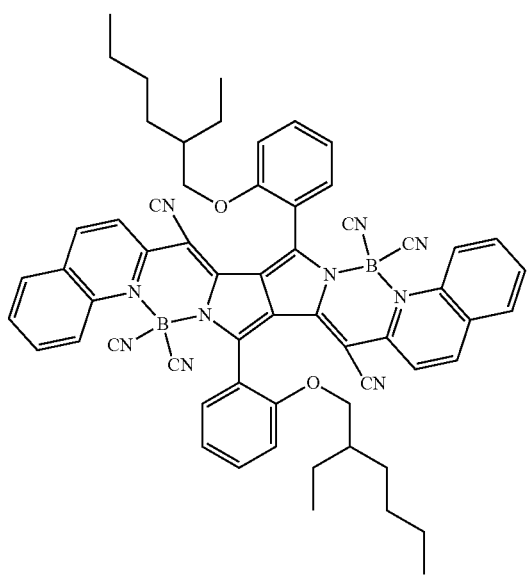

-continued
Df-39
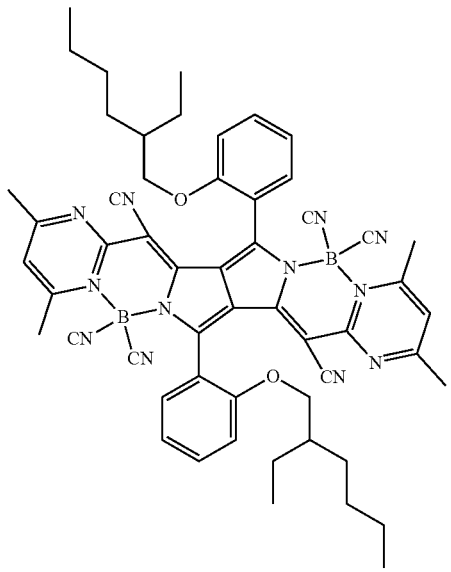
Df-40
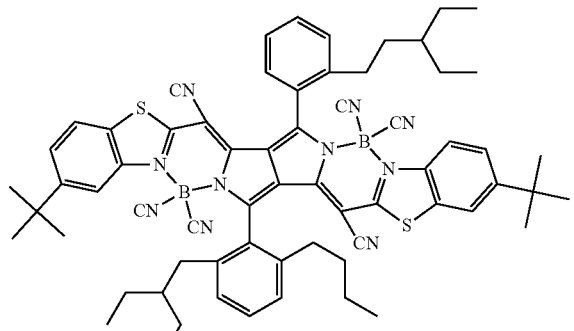
Df-41
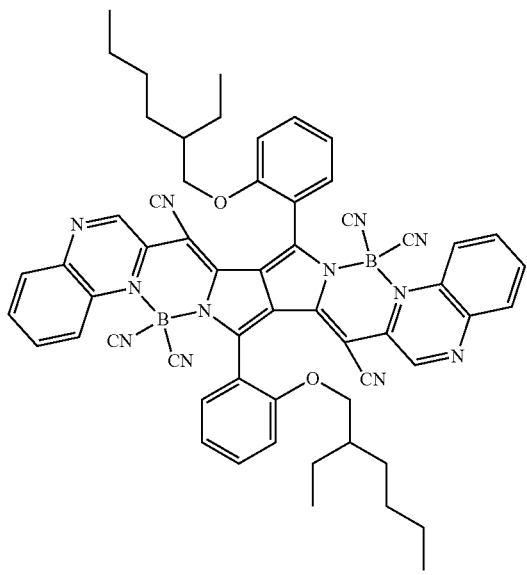
Df-42
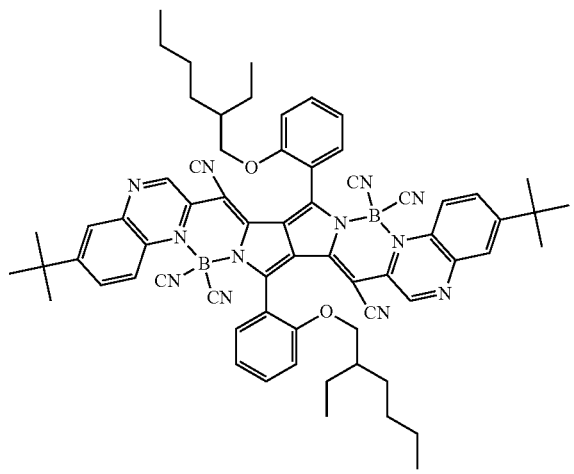
Df-43
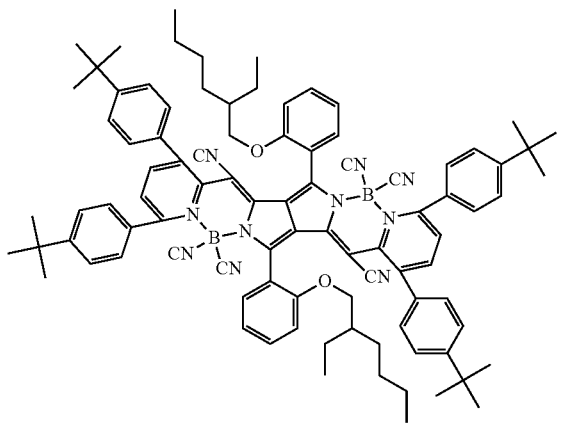
Df-44
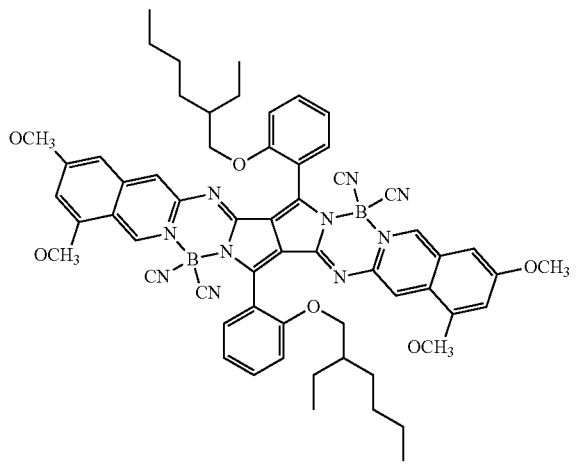

-continued
Df-45
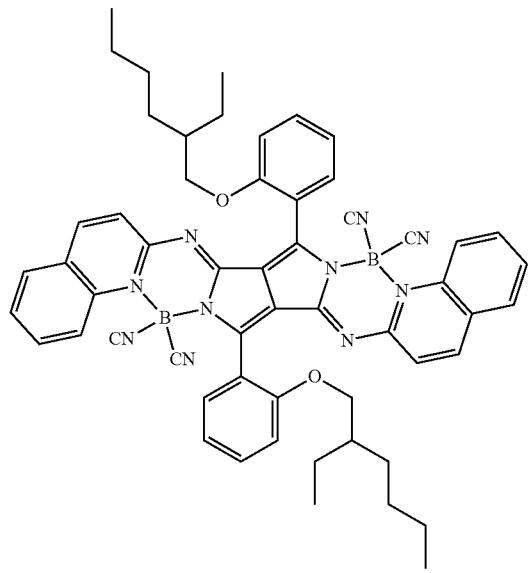
Df-46
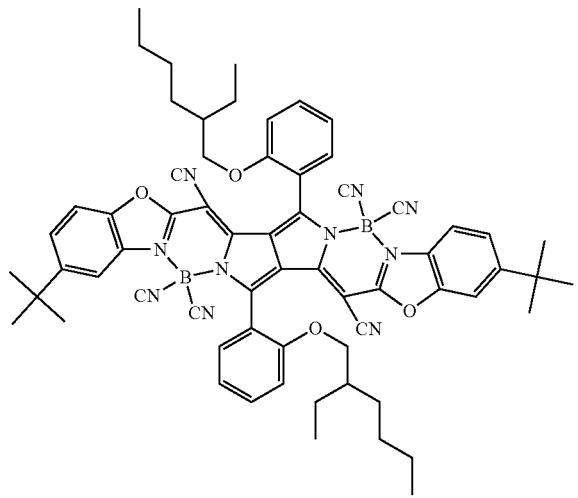
Df-47
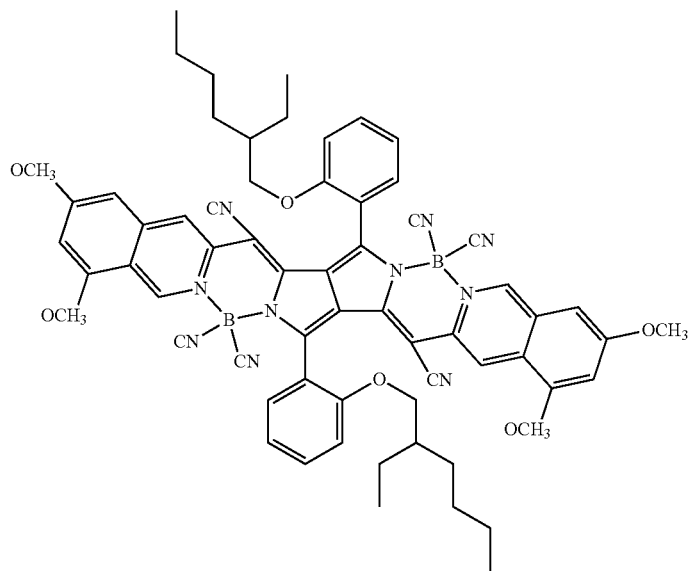

[Synthetic Method]

The squarylium compound represented by Formula (2a) according to the present invention may be synthesized by referring to the methods described in, for example, Chemistry of Materials, Vol. 23, p. 4789 (2011), The Journal of Physical Chemistry. Vol. 91, p. 5184 (1987), or the methods described in the references described in these documents. As an example, a synthetic example of an exemplified compound Da-2 is shown below <Synthesis of Exemplified Compound Da-2>

An exemplified compound Da-2 may be synthesized by the following scheme.

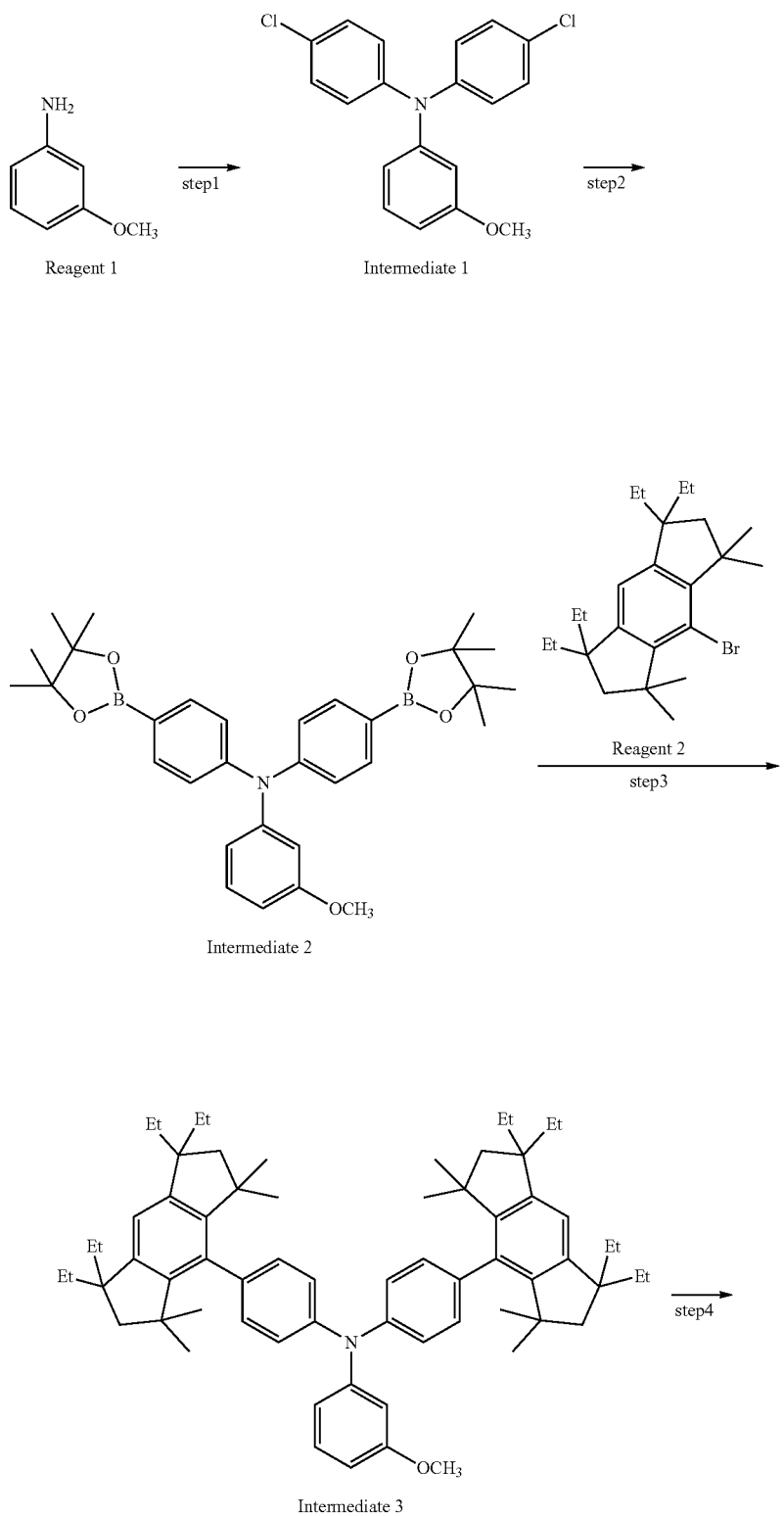

-continued

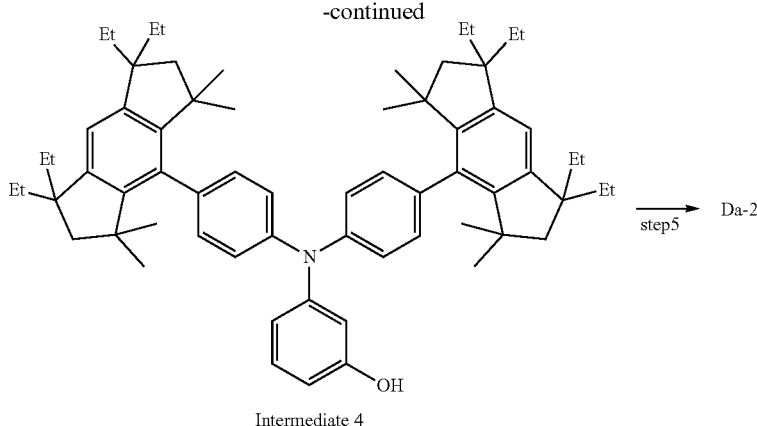

Intermediate 4

[$^1$H-NMR Spectrum of Da-2]

Measurement apparatus: JNM-ECZ400S (400 MHz, $^1$H-NMR)

Measuring conditions: 24.6° C., CDCl$_3$, solvent used, tetramethylsilane as standard (0 ppm):

δ/ppm=0.81 (48H, t, J=7 Hz), 0.97 (48H, s), 1.50-1.63 (nm, 16H), 1.60-1.72 (m, 16H), 6.47-6.54 (4H, m), 6.68 (4H, s), 7.20 (8H, d, J=8 Hz), 7.31 (8H, d, J=8 Hz), 7.92 (0.8H, d, J=9 Hz), 8.05 (0.2H, d, J=9 Hz), 11.5 (0.2H, s), 12.2 (0.8H, s).

The compounds represented by Formula (3a), Formula (4a), Formula (5a), Formula (6a), and Formula (7a) according to the present invention may also be synthesized by introducing the substituent according to the present invention in the same manner, for example, with reference to the method described in the patent document shown below.

Nature Materials vol. 15, 2016, p. 235-243
J. Phys. Chem. C, 2009, 113, p. 1589-1595
Materials, 2013, 6, p. 1779-1788
Molecules, 2018, 23, p. 226
Chem. Commun., 2010, 46, p. 5289-5291

[Emission Quantum Yield]

The emission quantum yield Φ(%) is expressed as a ratio of the number of absorbed photons and the number of emitted photons. If all of the excited molecules are returned to the ground state by fluorescence, the emission quantum yield Φ(%) is 100%, but it is not 100% when nonradiative deactivation occurs.

Nonradiative deactivation is a transition that returns to the ground state without fluorescence, and includes relaxation to the triplet state by intersystem crossing, internal conversion in which the energy of the electron state is converted into vibrational energy to finally become thermal energy, and energy transfer in which energy is transferred to other molecules. When the rate constants of the fluorescent transition and the nonradiative transition of the molecular in the excited state are Kf and Knr, respectively, the luminescence quantum yield Φ(%) is as follows.

$$\Phi(\%) = (Kf/(Kf+Knr)) \times 100$$

Therefore, in order to improve the emission quantum yield, it is necessary to suppress the nonradiative deactivation of the molecule in the excited state.

[Measurement of Fluorescence Spectrum]

The infrared-emitting compound of the present invention is a compound that emits fluorescence. The fluorescence spectrum of the infrared-emitting compound of the present invention may be confirmed by the following method.

The infrared-emitting compound of the present invention is adjusted to $10^{-6}$ M in toluene solution, and the fluorescent spectrum of this sample is measured at room temperature (300K). For measuring the emission spectrum, a spectrofluorometer (F7000, manufactured by Hitachi High-Tech Corporation) is used. This infrared-emitting compound exhibits fluorescence emission in which the maximum emission wavelength (wavelength at which the emission intensity is maximized; also referred to as "emission peak wavelength") exceeds 700 mu.

<<Applications>>

The infrared-emitting compound of the present invention exhibits long wavelength emission and high emission quantum yield. Since it has such a property, the infrared-emitting compound of the present invention may be used as a luminescent thin film, a luminescent particle, and a wavelength conversion film. For example, it may be utilized in bioimaging as a new type of dye for fluorescent probes as a label in biology and medicine. In addition, the infrared-emitting compound of the present invention, which emits fluorescence as extra energy when excited electrons return to the ground state, has wavelength conversion ability because of the difference between absorption and emission energy, and may be used as a color conversion filter for a dye, a pigment, an optical filter, or an agricultural film.

<Luminescent Thin Film>

The luminescent thin film of the present invention is characterized in that it contains an infrared-emitting compound of the present invention. The luminescent thin film of the present invention may be produced by forming a composition obtained by adding a dispersant to an infrared-emitting compound of the present invention for film forming stability, or a composition obtained by further adding a solvent to the composition in a thin film form.

Examples of the dispersant include (meth)acrylate-based resins, polyester-based resins, polyamide-based resins, polyimide-based resins, polystyrene-based resins, polyepoxy-based resins, polyester-based resins, amino-based resins, fluorine-based resins, phenol-based resins, polyurethane-based resins, polyethylene-based resins, polypropylene-based resins, polyvinyl chloride-based resins, polyvinyl alcohol-based resins, polyether-based resins, polyether ketone-based resins, polyphenylene sulfide resins, polycarbonate-based resins, aramid resins, and the like, but are preferably polystyrene-based resins, polyethylene-based resins, polypropylene-based resins, and polyvinyl chloride-based resins. Also, the copolymers of these are likewise preferred.

The (meth)acrylate-based resin is synthesized by homopolymerization or copolymerization of various methacrylate-based monomers or acrylate-based monomers, and a desired (meth)acrylate-based resin may be obtained by variously changing the monomer species and the monomer composition ratio. Further, in the present invention, it may also be used by copolymerizing with a (meth)acrylate-based monomer together with a copolymerizable monomer having an unsaturated double bond other than the (meth)acrylate-based monomer. And further, in the present invention, it may be used even when a plurality of other resins are mixed together with a poly (meth)acrylate-based resin.

Examples of the monomer component that form (meth) acrylate resins used in the present invention include (meth) acrylic acid, methyl (meth)acrylate, ethyl (meth)acrylate, propyl (meth)acrylate, butyl (meth)acrylate, isobutyl (meth) acrylate, t-butyl (meth)acrylate, stearyl (methylacrylate, 2-hydroxyethyl (meth)acrylate, acetoacetoxyethyl (meth) acrylate, dimethylaminoethyl (meth)acrylate, 2-hydroxypropyl (meth)acrylate, 2-hydroxypropyl (meth)acrylate, di(ethylene glycol) ethyl ether (meth) acrylate, ethylene glycol methyl ether (meth)acrylate, isobonyl (meth)acrylate, ethyltrimethylammonium chloride (meth)acrylate, trifluoroethyl (meth)acrylate, octafluoropentyl (meth)acrylate, 2-acetamidomethyl (meth)acrylate, 2-methoxyethyl (meth)acrylate, 2-dimethylaminoethyl (meth) acrylate, 3-trimethoxysilanepropyl (meth)acrylate, benzyl (methacrylate, tridecyl (meth)acrylate, 4-hydroxybutyl (meth)acrylate, tetrahydrofurfuryl (meth)acrylate, dodecyl (meth)acrylate, octadecyl (meth)acrylate, 2-diethylaminoethyl (meth)acrylate, 2-ethylhexyl (meth)acrylate, cyclohexyl (meta)acrylate, phenyl (meth)acrylate, and glycidyl (meth)acrylate. Among these, preferable are (meta)acrylic acid, methyl (meth)acrylate, ethyl (meth)acrylate, propyl (meth)acrylate, butyl (meth) acrylate, stearyl (meth)acrylate, 2-hydroxyethyl (meth)acrylate, acetoacetoxyethyl (meth)acrylate, benzyl (meth)acrylate, tridecyl (meth)acrylate, dodecyl (meth)acrylate, and 2-ethylhexyl (meth)acrylate.

Examples of the polystyrene-based resin include a homopolymer of a styrene monomer, or a random copolymer obtained by copolymerizing a monomer having another unsaturated double bond copolymerizable with a styrene monomer, a block copolymer, and a graft copolymer. In addition, blends or polymer alloys in which other polymers are compounded into such polymers are also included. Examples of the styrene monomer include nuclear alkyl-substituted styrenes such as styrene, α-methylstyrene, α-ethylstyrene, α-methylstyrene, p-methylstyrene, o-methylstyrene, m-methylstyrene, and p-methylstyrene; and nuclear halogenated styrenes such as o-chlorostyrene, m-chlorostyrene, p-chlorostyrene, p-bromostyrene, dichlorostyrene, dibromostyrene, trichlorostyrene, and tribromostyrene, among which styrene and α-methylstyrene are preferable.

Examples of the resin used in the present invention by homopolymerization or copolymerization of these include a copolymer resin of benzyl methacrylate/ethyl acrylate or butyl acrylate, a copolymer resin of methyl methactylate/2-ethylhexyl methacrylate, a copolymer resin of methyl methacrylate/methacrylate/stearyl methacrylate/acetoacetoxyethyl methacrylate, a copolymer resin of styrene/acetoacetoxyethyl methacrylate/stearyl methacrylate, a copolymer of styrene/2-hydroxyethyl methacrylate/stearyl methacrylate, and a copolymer resin of 2-ethylhexyl methacrylate/2-hydroxyethyl methacrylate.

The content of the luminescent material in the luminescent composition and the luminescent thin film of the present invention is a preferable lower limit of 0.001 parts by mass and a preferable upper limit of 50 parts by mass per 100 parts by mass of the above dispersant. When the content of the luminescent material is within this range, an image having high transparency and high luminance may be displayed by irradiation with light. A more preferable lower limit of the content of the above luminescent material is 0.01 parts by mass, a more preferable upper limit is 10 parts by mass, a further preferable lower limit is 0.05 parts by mass, a further preferable upper limit is 8 parts by mass, a particularly preferable lower limit is 0.1 parts by mass, and a particularly preferable upper limit is 5 parts by mass. In addition, the luminescent thin film of the present invention may be appropriately used within a thickness range of 0.1 nm to 1 mm.

<<Luminescent Particles>>

The luminescent particles of the present invention are characterized in that they contain an infrared-emitting compound of the present invention. The luminescent particle may be a luminescent particle in which an infrared-emitting compound is adsorbed on a particle surface, or may be a luminescent particle in which an infrared-emitting compound is contained.

For example, an infrared-emitting compound may be aggregated in a polymer particle dispersion in a liquid to produce luminescent particles. Further, when the polymer particles are immersed in a solvent, the particles may be luminescent particles containing an infrared-emitting compound using a swellable polymer which absorbs a solvent and expands in volume.

As the polymer particles, a commercially available product may be used, and those synthesized by a conventionally known method may be used. The conventionally known method is not particularly limited, and examples thereof include a dispersion polymerization method, a suspension polymerization method, and an emulsion polymerization method. Among them, an emulsion polymerization method is preferred. As the monomer serving as a raw material of the polymer, various monomers mentioned as the aforementioned dispersant may be used.

Further, the solvent for aggregating the infrared-emitting compound in the polymer dispersion in the liquid is not particularly limited Known solvents may be used.

The volume average particle diameter of the polymer particles is preferably within a range of 0.01 to 50 m, more preferably 0.02 to 1 m, and still more preferably 0.04 to 0.5 µm.

When the volume average particle diameter is in the above range, the obtained luminescent particles may be applied to various applications. The volume averaged particle diameter nay be specifically measured by a laser diffraction scattered light particle size distribution measuring apparatus LS13320 type.

The weight average molecular weight of the polymer particles is preferably within a range of 1000 to 1000000, more preferably 5000 to 800000, and still more preferably 10000 to 600000.

The polymer particles contained in the luminescent particles of the present invention may be one or two or more kinds, but are usually one kind.

<Wavelength Conversion Film and Infrared-Emitting Surface Light Source>

The wavelength conversion film of the present invention is characterized in that it contains an infrared-emitting compound of the present invention. The wavelength conversion film may be applied to an infrared-emitting surface light source which emits infrared light. The infrared-emitting surface light source of the present invention is characterized in that it includes a wavelength conversion film. The infrared-emitting surface light source of the present invention is a luminescent member that emits infrared light, and absorbs light of a surface light source such as an organic EL element, a micro LED, or an LED combined with a diffusion plate that emits light within a range of a visible light region (380 to 1000 nm) including a near-infrared light region, preferably a green to red region (495 to 900 nm) including a near-red light region, and particularly preferably a red region (600 to 850 nm) including a near-red light region, and emits light in a region of near-infrared light, for example, exceeding 700 nm and not exceeding 1500 un.

FIG. 1 shows a basic configuration of an infrared-emitting surface light source having a wavelength conversion film of the present invention. The infrared-emitting surface light source 1 shown in FIG. 1 has a configuration in which a wavelength conversion film 3 is placed on a surface light source 2 that emits visible light. An example of the surface light source 2 is an organic EL element that emits red light (R). The wavelength conversion film 3 of the present invention converts the visible light of the surface light source 2 into near-infrared light (IR).

The surface light source that emits visible light (red) is a light source having at least a characteristic of emitting red light, preferably a surface light source having a luminance uniformity of 70% or more when emitted uniformly A specific surface light source is preferably an organic electroluminescence element.

As a form of the infrared-emitting surface light source having a wavelength conversion film of the present invention, a surface light source that emits visible light (red) may be manufactured separately from the surface light source that emits light, and the wavelength conversion film may be used by superimposing it on the surface light source that emits visible light (red). Or, a wavelength conversion film may be laminated on the surface light source for emitting visible light (red). Alternatively, it may also serve as an adhesive or a scaling film. The thickness of the infrared-emitting surface light source including the wavelength conversion film of the present invention is also appropriately determined depending on the application, but 0.1 to 1000 μm is preferable from the viewpoint of flexibility and miniaturization, and more preferably within the range of 1 to 500 μm. An infrared-emitting surface light source comprising a wavelength conversion film of the present invention is suitably used in a biometric device and a biometric authenticator.

EXAMPLES

Hereinafter, the present invention will be specifically described with reference to Examples, but the present invention is not limited thereto. In Examples, "parts" or "%" is used, but unless otherwise specified, it indicates "parts by mass" or "% by mass".

Example 1

<Dihedral Angle>

For each of the 13 infrared-emitting compounds of the present invention and the comparative compounds $R_4$ to R-6 used in the following examples, the dihedral angle was calculated using a Gaussian 09 manufactured by Gaussian, Inc. as a software for calculating a molecular orbital under the conditions described above The results are indicated in Table I. In the case of a compound having no substituent according to the present invention, it was described as a hyphen "-".

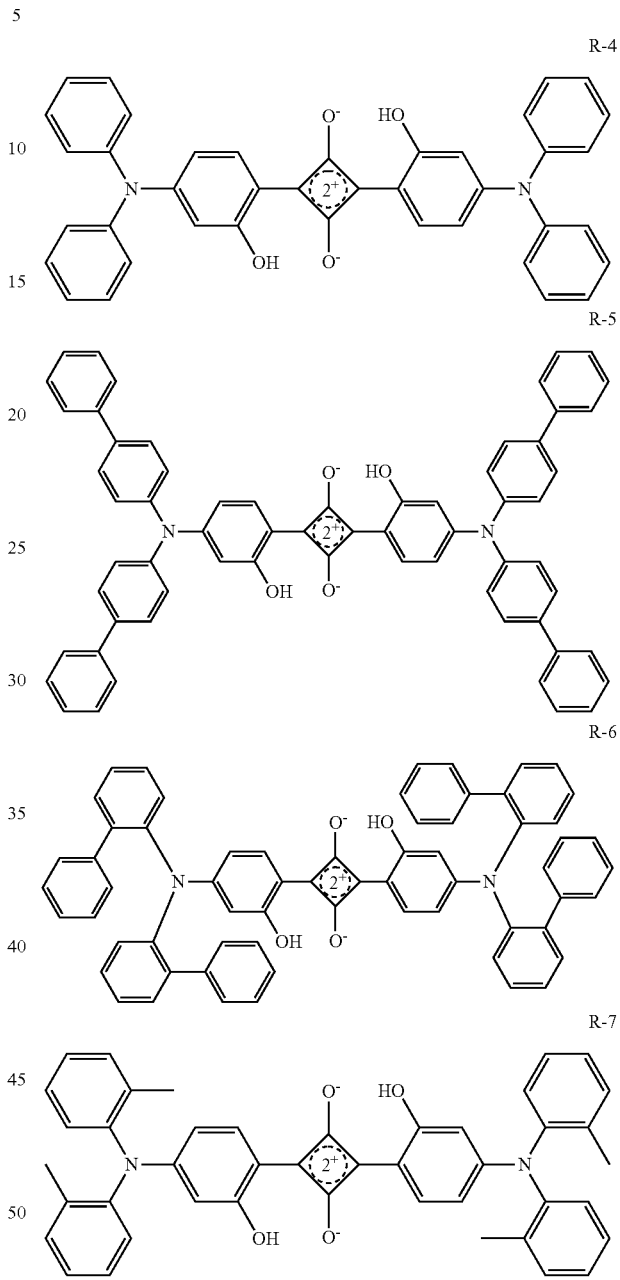

TABLE I

| Compound | Dihedral angle [degree] | Remarks |
| --- | --- | --- |
| R-4 | — | Comparative Example |
| R-5 | 38.4 | Comparative Example |
| R-6 | 38.4 | Comparative Example |
| Da-21 | 86.4 | Present Example |
| Da-38 | 90 | Present Example |
| Da-2 | 86.4 | Present Example |
| Da-41 | 90 | Present Example |
| Da-44 | 58.8 | Present Example |
| Da-45 | 58.8 | Present Example |

TABLE I-continued

| Compound | Dihedral angle [degree] | Remarks |
|---|---|---|
| Da-46 | 55.1 | Present Example |
| Da-9 | 55.1 | Present Example |
| Da-50 | 90.0 | Present Example |
| Da-51 | 86.4 | Present Example |
| Da-18 | 86.4 | Present Example |
| Da-66 | 86.4 | Present Example |
| Da-69 | 58.8 | Present Example |

<Measurement of Emission Wavelength and Emission Quantum Yield>

The emission wavelength and the emission quantum yield in the solution of each of the 13 infrared-emitting compounds of the present invention and the comparative compounds R-4 to R-6 shown in Table I were evaluated by the following methods.

(1) Evaluation of Emission Wavelength and Emission Quantum Yield in Solution

The infrared-emitting compound of the present invention was adjusted to $10^{-6}$M in a toluene solution, and the emission wavelengths (fluorescent spectrum) of the samples of the present invention were measured at room temperature (300 K). The emission wavelengths were measured using a spectrofluorometer (F7000, manufactured by Hitachi High-Tech Corporation). The emission quantum yield of the solution was measured using an absolute PL quantum yield measuring apparatus (C11347, manufactured by Hamamatsu Photonics K.K.).

The emission wavelength was evaluated based on the following criteria. ΔPL (λmax) is defined below.

ΔPL (λmax)[nm]=(Maximum emission wavelength of the corresponding compound)−(Maximum emission wavelength of compound R-6)

Figure 3:
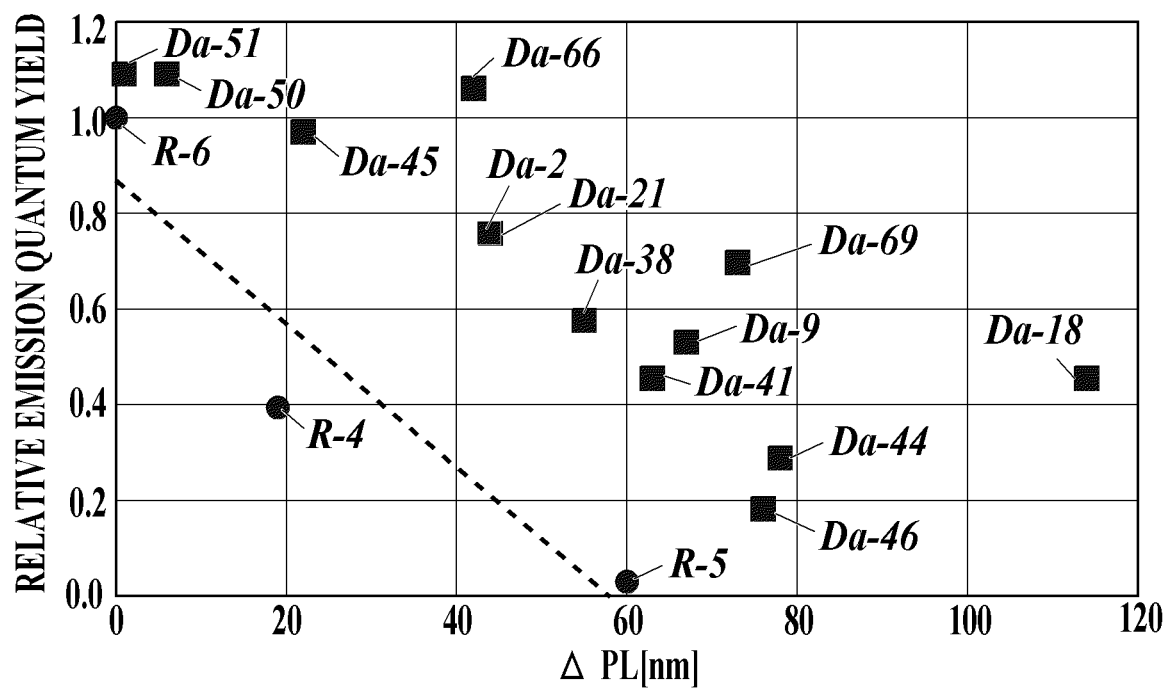
FIG. 3 is a graph showing an emission maximum wavelength and a relative emission quantum yield with respect to the comparative compound R-6.

The relative emission quantum yield when the emission quantum yield of R-6 was 1.0 was used as the emission quantum yield. The measurement results are indicated in FIG. 3. FIG. 3 is a graph showing APL and relative emission quantum yield with respect to the comparative compound R-6.

It can be seen from FIG. 3 that the 13 infrared-emitting compounds of the present invention have less reduction in the relative emission quantum yield even in the luminescence in the longer wavelength range than the comparative compounds R-4 to R-6.

(2) Evaluation of Emission Wavelength and Emission Quantum Yield in Thin Film (2)-1 Evaluation of Luminescent Thin Film of the Present Invention Polystyrene (manufactured by ACROS ORGANICS Co., Ltd., weight-average molecular weight Mw=260000) as a matrix material and the comparative compound R-4 were added to toluene so as to be 99:1 in mass ratio, and these were placed in a eggplant flask and heated to 80° C. with stirring, thereby sufficiently dissolving the mixture.

The obtained solution was coated on a quartz substrate by a spin coating method under a condition of 500 rpm and 30 seconds to form a thin film, and then dried at 80° C. for 10 minutes to prepare a luminescent thin film containing the comparative compound R-4. The luminescent thin film of the present invention was produced in the same manner except that the comparative R-4 was changed to the infrared-emitting compound Da-21 of the present invention. The emission wavelength (fluorescence spectrum) and absolute PL quantum yield of these samples were measured at room temperature (300 K). The emission wavelengths were measured using a spectrofluorometer (F7000, manufactured by Hitachi High-Tech Corporation) and an absolute PL quantum yield measuring apparatus (C11347, manufactured by Hamamatsu Photonics K.K.) was used for the measurement of absolute PL quantum yield. The absolute PL quantum yields of these luminescent thin films are shown below as relative values of the luminescent quantum yields when the absolute PL quantum yield of the comparative R-4 luminescent thin films in a toluene solution is 1.00.

TABLE II

| Compound | Emission quantum yield in toluene solution (relative value) | Emission quantum yield of luminescent thin film (relative value) | Remarks |
|---|---|---|---|
| R-4 | 100 | 38 | Comparative Example |
| Da-21 | 192 | 153 | Present Example |

From Table II, it was found that the luminescent thin film using the comparative compound R-4 maintained an emission quantum yield of 0.38 from the solution state, whereas the luminescent thin film using the infrared-emitting compound Da-21 of the present invention achieved an emission quantum yield of 0.80 from the solution state, and concentration quenching was remarkably suppressed. Furthermore, the luminescent thin film of Da-21 of the present invention exhibited a longer wavelength luminescence by 20 nm or more and a higher luminescence quantum yield than the luminescent thin film of the comparative compound R-4.

(2)-2 Evaluation of the Luminescent Thin Film of the Present Invention

A luminescent thin film containing the comparative compound R-7 was prepared in the same manner as in the luminescent thin film of the comparison described in (2)-1, except that the comparative compound R-4 was changed to the comparative compound R-7. Further, luminescent thin films of the present invention were prepared in the same manner except that the comparative compound R-7 was changed to the infrared-emitting compounds Da-50 and Da-51 of the present invention, respectively. The luminescence wavelength (fluorescence spectrum) and the luminescence quantum yield of these samples were measured in the same manner as (2)-1. The relative values of the emission quantum yields of these luminescent thin films are shown below when the emission quantum yield of each luminescent thin film in toluene solution is set to 1.00.

TABLE III

| Compound | Emission quantum yield in toluene solution (relative value) | Emission quantum yield of luminescent thin film (relative value) | Remarks |
|---|---|---|---|
| R-7 | 1.00 | 0.46 | Comparative Example |
| Da-50 | 1.00 | 0.76 | Present Example |
| Da-51 | 1.00 | 0.81 | Present Example |
| R-8 | 1.00 | 0.14 | Comparative Example |
| Db-14 | 1.00 | 0.56 | Present Example |
| R-9 | 1.00 | 0.10 | Comparative Example |
| Db-7 | 1.00 | 0.59 | Present Example |
| R-10 | 1.00 | 0.32 | Comparative Example |
| Df-1 | 1.00 | 0.60 | Present Example |
| Df-13 | 1.00 | 0.63 | Present Example |
| Df-14 | 1.00 | 0.57 | Present Example |
| Df-17 | 1.00 | 0.61 | Present Example |
| Df-22 | 1.00 | 0.69 | Present Example |
| Df-36 | 1.00 | 0.67 | Present Example |
| Df-40 | 1.00 | 0.64 | Present Example |
| Df-46 | 1.00 | 0.59 | Present Example |
| Da-66 | 1.00 | 0.70 | Present Example |
| Da-69 | 1.00 | 0.65 | Present Example |

From Table III, it was found that the luminescent thin filmi using the comparative compound 1R-7 maintained a quantum yield of 0.46 compared to the solution state, whereas the luminescent thin film using the infrared luminescent compound of the present invention achieved a high emission quantum yield of 0.76 compared to the solution state of Da-50, and 0.81 compared to the solution state of Da-5 I, respectively, and the concentration quenching was remarkably suppressed. Furthermore, the luminescent thin film of the present invention exhibited longer wavelength luminescent and higher luminescence quantum yield than the comparative luminescent thin film. Similar results were obtained in comparison of the comparative compounds R-8 to R-10 with the luminescent thin films using infrared-emitting compounds of the present invention.

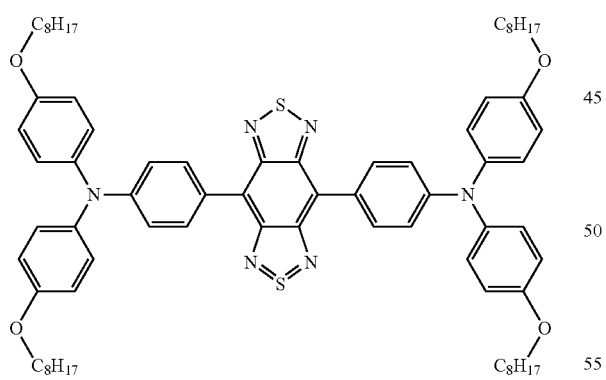

R-8

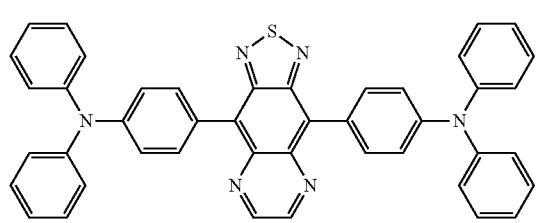

R-9

R-10

Note that the comparative compounds R-8, R-9 and R-10 each are a compound described in the following literature.
R-8: Chem. Mater., vol. 20, 2008, 6208
R-9: J. Phys. Chem. C, 2009, 113, 1589
R-10: Chem. Eur. J., 2009, 15, 4857

Example 2

<Luminescent Particles>

The luminescence quantum yield in the luminescent particles was measured for the infrared-emitting compound of the present invention and the comparative compound.

(1) Preparation of Luminescent Particles

To 96 μL of a polystyrene (PS) particle dispersion (solid content: 5.2% by mass, volume average particle diameter of polystyrene particles: 0.12 μm, dispersion medium: water) were added 100 μL of water, 50 μL of a 2% aqueous solution of a nonionic surfactant (Kolliphor P407, manufactured by Sigma-Aldrich Co., Ltd.), and 100 μL of a 0.01 mmol/L THF solution of each compound shown in Table IV to prepare a mixed liquid of polystyrene particles and each compound. Polystyrene particles were prepared by stirring the mixture at 25° C. for 2 minutes.

Using a dispersion of the obtained polystyrene particles, the particles were sedimented by a centrifugal purification method, and after removing the supernatant liquid, pure water was added to redisperse the particles. This operation (centrifugal purification and redispersion) was repeated four times to obtain luminescent particle dispersions 1 to 6 containing each compound.

(2) Evaluation of Quantum Yield

The absolute fluorescence quantum yield of the luminescent particle dispersions 1 to 6 containing polystyrene particles obtained in the preceding paragraph was measured using a fluorescence quantum yield measuring apparatus (C11347-01, manufactured by Hamamatsu Photonics K.K.). A luminescence quantum yield of each of them was evaluated as relative value when the fluorescence quantum yield of the dispersion No. 4 containing Da-21 of the present invention was set to 1.0. The obtained results are shown in Table IV.

TABLE IV

| Luminescent particle dispersion No. | Compound | Emission quantum yield (relative value) | Remarks |
|---|---|---|---|
| 1 | R-1 | 0.60 | Comparative Example |
| 2 | R-2 | 0.01 | Comparative Example |
| 3 | R-3 | 0.01 | Comparative Example |
| 4 | Da-21 | 1.00 | Present Example |
| 5 | Da-38 | 0.90 | Present Example |
| 6 | Da-18 | 1.00 | Present Example |

From Table IV, it can be seen that the compounds of the present invention exhibit high emission quantum yields in polymer particles relative to the comparative compounds.

Example 3

<Wavelength Conversion Film>
[Preparation of Wavelength Conversion Film]
(Preparation of Wavelength Conversion Film 3)

Figure 2:
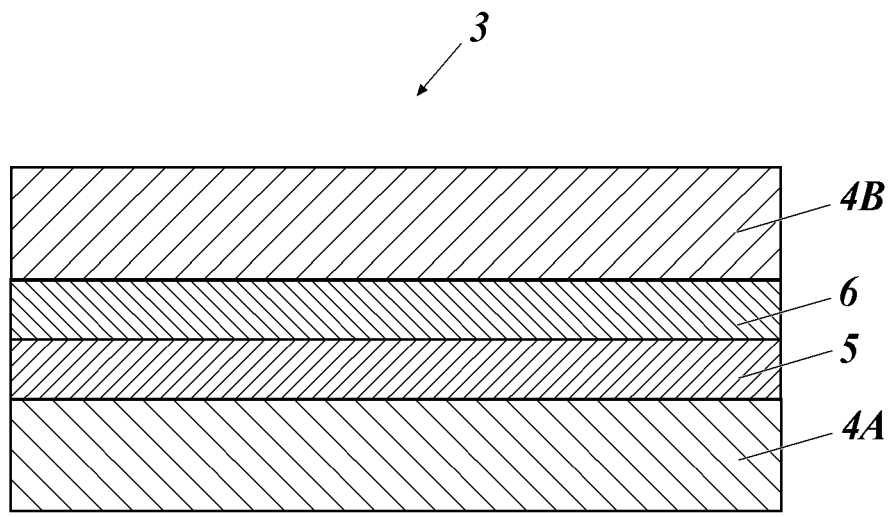
FIG. 2 is a schematic cross-sectional view showing an example of a configuration of a wavelength conversion film of the present invention having a sealing structure.

The wavelength conversion film 3 having the structure shown in FIG. 2 was produced according to the following method.

To toluene as a solvent, polystyrene (manufactured by ACROS ORGANICS Co., Ltd., weight-average molecular weight Mw=260000) as a matrix material and an infrared-emitting compound Da-53 of the present invention were added so as to have a mass ratio of 99:1, and these were placed in a eggplant flask and heated and stirred at 80° C. thereby sufficiently dissolving the mixture.

Next, on the entire surface of one side of a polyethylene naphthalate film (manufactured by Teijin DuPont Corporation, hereinafter abbreviated as PEN), the obtained mixed solution was applied using an applicator onto a gas barrier film in which an inorganic gas barrier layer made of $SiO_x$ was formed to have a thickness of 500 nm by using an atmospheric pressure plasma-discharge treatment apparatus having a configuration described in JP-A 2004-68143. After drying at mom temperature for 10 minutes, heating and drying was further performed at 80° C. for 10 minutes to forma luminescent dye layer 5. Thereafter, the adhesive layer 6 was applied and formed on the gas barrier film 4B, then, bonded with the coating surface, and it was sealed using a vacuum laminator at 90° C. heating conditions. Thereafter, the adhesive was cured by performing a heat treatment at 110° C. for 30 minutes to prepare a wavelength conversion film 3.

(Preparation of an Infrared-Emitting Surface Light Source)

An infrared-emitting surface light source 1 having the configuration shown in FIG. 1 was produced by bringing the light emitting surface of the organic EL element, which is a surface light source emitting red light (R), into close contact with the wavelength conversion film 3.

It was confirmed that the red light of the surface light source that emits red light (R) is converted into near-infrared light by emitting the surface light source that emits red light (R).

INDUSTRIAL APPLICABILITY

The infrared-emitting compound of the present invention enables to achieve long wavelength emission and high emission quantum yield. Therefore, the present invention can be preferably applied to a luminescent thin film containing an infrared-emitting compound, luminescent particles, a wavelength conversion film, and an infrared-emitting surface light source provided with the wavelength conversion film.

DESCRIPTION OF SYMBOLS

1: Infrared-emitting surface light source
2: Surface light source that emits visible light
3: Wavelength conversion film
4A, 4B: Gas barrier film
5: Luminescent dye layer
6: Adhesive layer
IR: Near-infrared light
R: Red light emission

What is claimed is:

1. An infrared-emitting compound having a structure represented by the following Formula (2b):

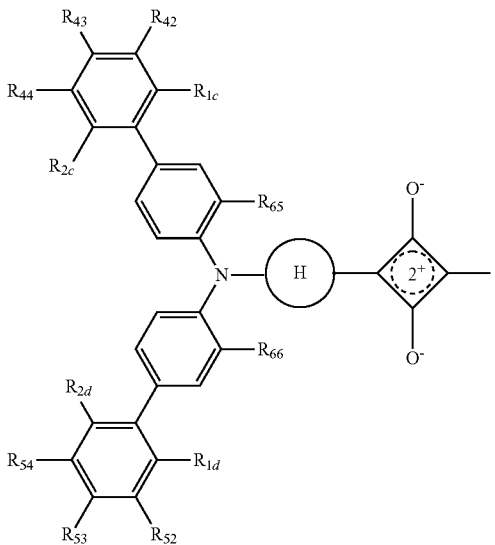

Formula (2b)

-continued

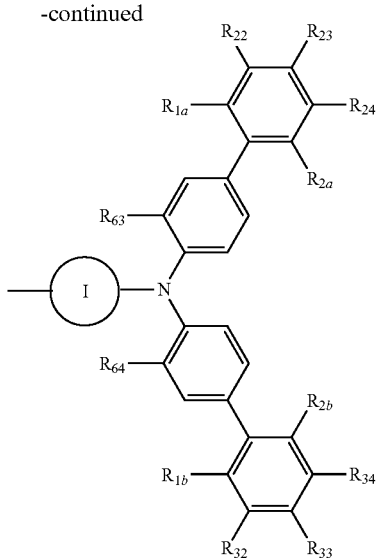

in Formula (2b), $R_{1a}$ to $R_{1d}$, $R_{2a}$ to $R_{2d}$, $R_{22}$ to $R_{24}$, $R_{32}$ to $R_{34}$, $R_{42}$ to $R_{44}$, $R_{52}$ to $R_{54}$, and $R_{63}$ to $R_{66}$ each independently represent a hydrogen atom, an alkyl group, an alkoxy group, a phenoxy group, an amino group, an aryl group, or a heteroaryl group, but at least one of the combinations of $R_{1a}$ and $R_{2a}$, $R_{1b}$ and $R_{2b}$, $R_{1c}$ and $R_2c$, and $R_{1d}$ and $R_2d$ does not both represent a hydrogen atom; $R_{1a}$ and $R_{22}$, $R_2a$ and $R_{24}$, $R_{1b}$ and $R_{32}$, $R_2b$ and $R_{34}$, $R_{1c}$ and $R_{42}$, $R_{2c}$ and $R_{44}$, $R_{1d}$ and $R_{52}$, and $R_{2d}$ and $R_{54}$ may be bonded respectively to form a ring structure; and ring H and ring I each independently represent an aryl group which may be substituted with a hydroxy group, an alkoxy group, an NHCORa group, in which Ra represents a hydrocarbon group, an $NHSO_2Rb$ group, in which Rb represents a hydrocarbon group, or an NHPO(ORf) (ORg) group, in which Rf and Rg each independently represent a hydrocarbon group.

2. The infrared-emitting compound described in claim 1, wherein, in the Formula (2b), $R_{1a}$ to $R_{1d}$ and $R_{2a}$ to $R_{2d}$ are the same and represent an alkyl group, an alkoxy group, a phenoxy group, an amino group, an aryl group or a heteroaryl group.

3. The infrared-emitting compound described in claim 1, wherein, in the Formula (2b), ring H and ring I are the same and represent an aryl group having a hydroxyl group, $R_{23}$, $R_{33}$, $R_{43}$ and $R_{53}$ are the same as $R_{1a}$ to $R_{1d}$ and $R_{2a}$ to $R_{2d}$, respectively, or represent a hydrogen atom, but at least one of the combinations of $R_{1a}$ and Rea, $R_{1b}$ and $R_{2b}$, $R_{1c}$ and $R_{2c}$, and $R_{1d}$ and $R_2d$ does not both represent a hydrogen atom, and $R_{22}$, $R_{24}$, $R_{32}$, $R_{34}$, $R_{42}$, $R_{44}$, $R_{52}$ and $R_{54}$ represent a hydrogen atom.

4. The infrared-emitting compound described in claim 1, wherein, in the Formula (2b), ring H and ring I are the same and represent an aryl group having a hydroxy group; $R_{1a}$ is bonded to $R_{22}$, $R_{2a}$ is bonded to $R_{24}$, $R_{1b}$ is bonded to $R_{32}$, $R_2b$ is bonded to $R_{34}$, $R_{1c}$ is bonded to $R_{42}$, $R_2c$ is bonded to $R_{44}$, $R_{1d}$ is bonded to $R_{52}$, and $R_2d$ is bonded to $R_{54}$ respectively to form a 5-membered ring or a 6-membered ring with a carbon chain.

5. A luminescent thin film containing the infrared-emitting compound described in claim 1.

6. A luminescent particle containing the infrared-emitting compound described in claim 1.

7. A wavelength conversion film containing the infrared-emitting compound described in claim 1.

8. An infrared-emitting surface light source comprising the wavelength conversion film described in claim 7.

* * * * *